US009573952B2

(12) United States Patent
Allen et al.

(10) Patent No.: US 9,573,952 B2
(45) Date of Patent: Feb. 21, 2017

(54) METHODS OF PREPARING TOLL-LIKE RECEPTOR MODULATORS

(71) Applicant: Gilead Sciences, Inc., Foster City, CA (US)

(72) Inventors: Darin Allen, Pacifica, CA (US); Brandon Heath Brown, Burlingame, CA (US); Jessica Jade Chao, San Jose, CA (US); Randall L. Halcomb, Foster City, CA (US); Paul Hrvatin, Sacramento, CA (US); Ryan McFadden, Foster City, CA (US); Paul Roethle, Berkeley, CA (US); Erwina Rudio, Tracy, CA (US); Hong Yang, Fremont, CA (US); Richard Hung Chiu Yu, San Francisco, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 14/853,883

(22) Filed: Sep. 14, 2015

(65) Prior Publication Data

US 2016/0075707 A1 Mar. 17, 2016

Related U.S. Application Data

(60) Provisional application No. 62/051,044, filed on Sep. 16, 2014.

(51) Int. Cl.
*C07D 247/02* (2006.01)
*C07D 475/06* (2006.01)
*C07D 207/09* (2006.01)
*C07D 239/47* (2006.01)
*C07D 239/46* (2006.01)
*C07D 239/48* (2006.01)
*C07D 239/545* (2006.01)
*C07D 487/04* (2006.01)
*C07D 207/06* (2006.01)

(52) U.S. Cl.
CPC .......... *C07D 475/06* (2013.01); *C07D 207/06* (2013.01); *C07D 207/09* (2013.01); *C07D 239/46* (2013.01); *C07D 239/47* (2013.01); *C07D 239/48* (2013.01); *C07D 239/545* (2013.01); *C07D 487/04* (2013.01)

(58) Field of Classification Search
CPC .......................... C07D 247/02; C07D 475/06
See application file for complete search history.

(56) References Cited

U.S. PATENT DOCUMENTS

| 5,057,540 | A | 10/1991 | Kensil et al. |
| 5,424,311 | A | 6/1995 | Billhardt-Troughton et al. |
| 5,620,978 | A | 4/1997 | Cai et al. |
| 5,693,641 | A | 12/1997 | Buckman et al. |
| 6,299,884 | B1 | 10/2001 | Van Nest et al. |
| 6,452,325 | B1 | 9/2002 | Dupont |
| 8,809,527 | B2 | 8/2014 | Desai et al. |
| 2004/0029885 | A1 | 2/2004 | Bauer et al. |
| 2009/0263470 | A1 | 10/2009 | Coller et al. |
| 2010/0143301 | A1* | 6/2010 | Desai .................. C07D 475/06 424/85.7 |

FOREIGN PATENT DOCUMENTS

| EP | 1939201 A1 | 7/2008 |
| EP | 2143724 A1 | 1/2010 |
| EP | 2364314 A1 | 9/2011 |
| JP | 2886570 B2 | 4/1999 |
| WO | WO-9014837 A1 | 12/1990 |
| WO | WO-9744038 A1 | 11/1997 |
| WO | WO-9805661 A1 | 2/1998 |
| WO | WO-0000478 A1 | 1/2000 |
| WO | WO-0119825 A1 | 3/2001 |
| WO | WO-02076954 A1 | 10/2002 |
| WO | WO-03020722 A1 | 3/2003 |
| WO | WO-2004076454 A1 | 9/2004 |
| WO | WO-2005123736 A1 | 12/2005 |
| WO | WO-2006117670 A1 | 11/2006 |
| WO | WO-2007014838 A1 | 2/2007 |
| WO | WO-2007108968 A2 | 9/2007 |
| WO | WO-2007148064 A1 | 12/2007 |
| WO | WO-2008051493 A2 | 5/2008 |
| WO | WO-2008101867 A1 | 8/2008 |
| WO | WO-2008113711 A1 | 9/2008 |
| WO | WO-2009022185 A2 | 2/2009 |
| WO | WO-2009023269 A2 | 2/2009 |
| WO | WO-2009067547 A1 | 5/2009 |
| WO | WO-2010077613 A1 | 7/2010 |
| WO | WO-2012087596 A1 | 6/2012 |

OTHER PUBLICATIONS

Barr, Ig., et al., (1998), "ISCOMs and other saponin based adjuvants", *Advanced Drug Delivery Reviews*, 32:247-71.
Boyer, N., et al., (2000), "Pathogenesis, diagnosis and management of hepatitis C", *J. Of Hepatology*, 32 (Supp. 1) 98-112.
Boyle, P., et al., (1991), "Synthesis of a 2,4-Diaminodihydrohomopteridine, 6-Acetyl-2, 4-Diamino-7,8-Dihydro-9H-Pyrimido[4,5-b][1,4]Diazepine, Using a Furazano[3,4-d]Pyrimidine Precursor", *Tetrahedron*, 47(28):5259-68.
Breault, G., et al., (2008), "Exploring 8-benzyl pteridine-6, 7-diones as Inhibitors of glutamate racernase (MurI) in Gram-positive bacteria", *Bioorganic & Medicinal Chemistry Letters*, 18(23):6100-03.
Calisher, C.H., et al., (1989), "Antigenic Relationships between Flaviviruses as Determined by Cross-neutralization Tests with Polyclonal Antisera", *J. gen Virol.*, 70:37-43.
Di Bisceglie, A., et al., (1999), "The Unmet Challenges of Hepatitis C", *Scientific American, Inc.*, 80-5.
Dustin, L., (2007), "Flying Under the Radar: The Immunobiology of Hepatitis C", *Annu. Rev. Immunol.*, 25:71-99.
Dymock, B., et al., (2000), "Novel approaches to the treatment of hepatitis C virus infection", *Antiviral Chemistry & Chemotherapy*, 11:79-96.
Dzierba, C., et al., (2007), "Dihydropyridopyrazinones and Dihydropteridinones as Corticotropin-Releasing Factor-1 Receptor Antagonists: Structure—Activity Relationships and Computational Modeling", *J Med Chem*, 50:2269-72.
Gluck, R., et al., (2002), "New technology platforms in the development of vaccines for the future", *Vaccine*, 5:B10-6.

(Continued)

*Primary Examiner* — Bruck Kifle
(74) *Attorney, Agent, or Firm* — Timothy A. Marquart

(57) ABSTRACT

The present invention provides methods of preparing 4-amino-2-butoxy-8-(3-(pyrrolidin-1-ylmethyl)benzyl)-7,8-dihydropteridin-6(5H)-one and related compounds.

49 Claims, 4 Drawing Sheets

(56) References Cited

OTHER PUBLICATIONS

Goodchild, A., et al., (2009), "Primary Leukocyte Screens for Innate Immune Agonists", *Journal of Biomolecular Screening*, 14:723-30.
Gordon, CP, et al., (2005), "Control of Hepatitis C: A Medicinal Chemistry Perspective", *Journal of Medicinal Chemistry*, 48:1-20.
Horsmans, Y., et al., (2005), "Isatoribine, an Agonist of TLR7, Reduces Plasma Virus Concentration in Chronic Hepatitis C Infection", *Hepatology*, 42:724-31.
Illan-Cabeza, I., et al., (2013), "Antiproliferative effects of palladium(II) complexes of 5-nitrosopyrimidines and interactions with the proteolytic regulatory enzymes of the renin-angiotensin system in tumoral brain cells", *J Inorg Biochem*, 126:118-27.
International Search Report and Written Opinion for PCT/US2009/067002.
International Search Report and Written Opinion for PCT/US2015/050039.
Jin, G., et al., (2006), "Synthesis and immunostimulatory activity of 8-substituted amino 9-benzyladenines as potent Toll-like receptor 7 agonists", *Bioorg Med Chem Lett*, 16:4559-63.
Korba, Be, et al., (2000), "Treatment of Chronic Woodchuck Hepatitis Virus Infection in the Eastern Woodchuck (Marrnota monax) with Nucleoside Analogues is Predictive of Therapy for Chronic Hepatitis B Virus Infection in Humans", *Hepatology*, 31:1165-75.
Lee, J., et al., (2006), "Activation of anti-hepatitis C virus responses via Toll-like receptor 7", *Proc. Natl. Acad. Sci.*, 103:1828-33.
Menne, S., et al., (2007), "The woodchuck as an animal model for pathogenesis and therapy of chronic hepatitis B virus infection", *World J. Gastroenterol.*, 13:104-24.
Moennig, V., et al., (1992), "The Pestiviruses", *Advances in Virus Research*, 41:53-98.
Moradpour, D., et al., (2007), "Replication of hepatitis C virus", *Nature Reviews, Microbiology*, 5:453-63.
Moye, C.J., et al., (1964), "The synthesis of 4,6-Dihydroxy-2-methoxypyrimidine and derived pyrimidine intermediates", *Aust. J. Chem.*, 17:1309-10.
Nagashima, T., et al., (2004), "Solution—Phase Parallel Synthesis of an N-Alkylated Dihydropteridinone Library from Fluorous Amino Acids", *J. Comb Chem.*, 6:942-9.
Roethle, P., et al., (2013), "Identification and optimization of pteridinone Toll-like receptor 7 (TLR7) agonists for the oral treatment of viral hepatitis", *J Med Chem.*, 56:7324-33.
Scott, L., et al., (2002) "Interferon-alpha-2b plus ribavirin: a review of its use in the management of chronic hepatitis C", *Drugs*, 62:507-56.
Sun, P., et al., (2009), "Functional characterization of ex vivo blood myeloid and plasmacytoid dendritic cells after infection with dengue virus", *Virology*, 383:207-15.
Susvilo, I., et al., (2006) "Study on the Reaction of Methyl N-Methyl-N-(6-substituted-5- nitropyrimidine-4-yl) glycinates with Sodium Alkoxides", *J. Heterocyclic Chem.*, 43, 267-76.
Tennant, B., (1999), "Animal Models of Hepatitis B Virus Infection", *Clinics in Liver Disease*, 3:241-66.
Thomas, A., et al., (2007), "Investigating Toll-Like Receptor Agonists for Potential to Treat Hepatitis C Virus Infection", *Antimicrobial Agents and Chemotherapy*, 51:2969-78.

\* cited by examiner

METHODS OF PREPARING TOLL-LIKE RECEPTOR MODULATORS

CROSS-REFERENCES TO RELATED APPLICATIONS

This application claims priority to U.S. Provisional Application No. 62/051,044, filed Sep. 16, 2014, which is incorporated in its entirety herein for all purposes.

BACKGROUND

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR-7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines. Agonists of TLR-7 are immunostimulants and induce the production of endogenous interferon-α in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections such as HBV, Flaviviridae viruses, HCV, HPV, RSV, SARS, HIV, or influenza.

The treatment of Flaviviridae virus infections with TLR agonists is particularly promising. Viruses of the Flaviviridae family comprise at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV), Japanese encephalitis virus (JEV), tick-borne encephalitis virus, Junjin virus, Murray Valley encephalitis, St Louis encephalitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000). There are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit.

HCV is recognized by innate virus-sensing mechanisms that induce a rapid IFN response (Dustin, et al., *Annu. Rev. Immunol.* 2007, 25, 71-99). It is likely that the sources of the IFN are, at least, the infected hepatocytes and particularly the plasmacytoid dendritic cells (pDC) that highly express TLR-7 receptors and secrete high amounts of IFN. Horsmans, et al. (*Hepatology,* 2005, 42, 724-731), demonstrated that a once daily 7-day treatment with the TLR-7 agonist isatoribine reduces plasma virus concentrations in HCV infected patients. Lee, et al. (*Proc. Natl. Acad. Sci. USA,* 2006, 103, 1828-1833), demonstrated that TLR-7 stimulation can induce HCV immunity by both an IFN and IFN-independent mechanisms. These workers also revealed that TLR-7 is expressed in normal as well as HCV infected hepatocytes. These combined results support the conclusion that stimulation of TLR-7 receptors, such as through the administration of a TLR-7 agonist, is a viable mechanism for effectively treating natural HCV infections. Given the need for more effective treatments for HCV infections, there is a need to develop safe and therapeutically effective TLR-7 agonists.

Similarly, despite the existence of efficient vaccines, hepatitis B virus (HBV) infection remains a major public health problem worldwide with 400 million chronic carriers. These infected patients are exposed to a risk of developing liver cirrhosis and hepatocellular carcinoma (Lee, W. M. 1997, N. Eng. J. Med., 337, 1733-1745). Currently, there are believed to be approximately 1.25 million chronic hepatitis B carriers just in the United States, with 200,000 people newly infected each year by contact with blood or body fluids.

Hepatitis B virus is second to tobacco as a cause of human cancer. The mechanism by which HBV induces cancer is unknown, although it is postulated that may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes.

HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of HIV, which accounts for why HBV infection is common among patients with AIDS or HIV-associated infections. However, HBV is more contagious than HIV. To ameliorate suffering and to prolong the lives of infected hosts new compounds and methods of treating AIDS and attacking the HIV virus continue to be sought.

BRIEF SUMMARY OF THE INVENTION

In some embodiments, the present invention provides a method of making a compound of Formula Ia:

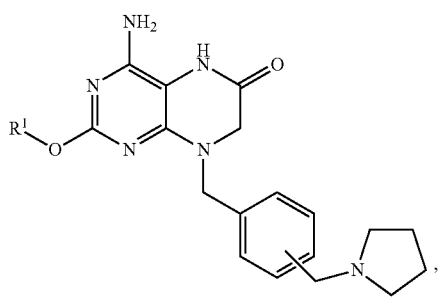
(Ia)

including the step of forming a first reaction mixture of a compound of Formula IIa:

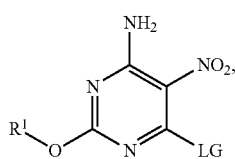
(IIa)

a non-nucleophilic base, a first solvent, and a compound of Formula IIIa:

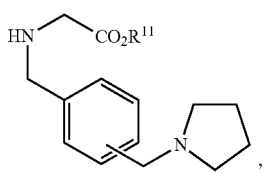
(IIIa)

under conditions suitable to form a compound of Formula IVa:

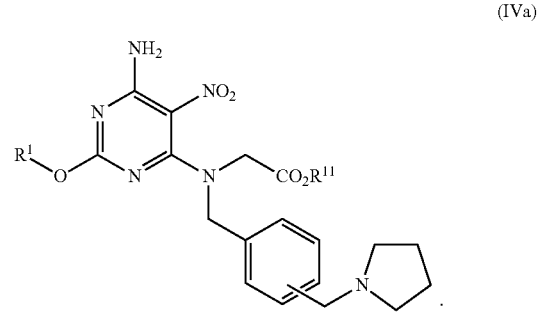
(IVa)

The method also includes the step of forming a second reaction mixture of the compound of Formula IVa, a second solvent and a reducing agent under conditions suitable to prepare the compound of Formula Ia. Groups $R^1$ and $R^{11}$ can each independently be $C_1$-$C_6$ alkyl; and LG can be halogen, —OH, or —OSO$_2$R$^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or NO$_2$.

In some embodiments, the present invention provides a method of preparing a compound of Formula IIIa:

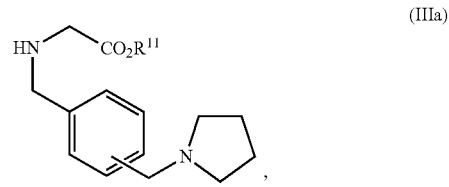
(IIIa)

including the step of forming a first reaction mixture of Br—CH$_2$—CO$_2$R$^{11}$, a non-nucleophilic base, and a compound of Formula Va, under conditions suitable to form the compound of Formula IIIa, wherein the compound of Formula IIIa can be present at the kilogram scale. Group $R^{11}$ of Formula IIIa and Br—CH$_2$—CO$_2$R$^{11}$ can be $C_1$-$C_6$ alkyl.

In some embodiments, the present invention provides a method of preparing a compound of Formula IIIa:

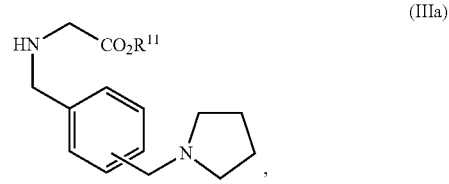
(IIIa)

including the step of forming a first reaction mixture of OHC—CO$_2$R$^{11}$, a reducing agent, and a compound of Formula Va:

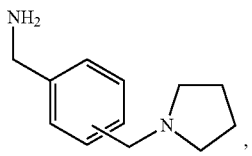
(Va)

under conditions suitable to form the compound of Formula IIIa, wherein group $R^{11}$ can be $C_1$-$C_6$ alkyl.

In some embodiments, the present invention provides a method of preparing a compound of Formula IIIa:

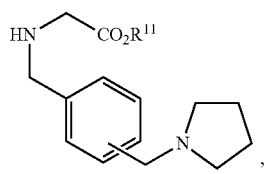
(IIIa)

including the step of forming a first reaction mixture of $H_2N$—$CH_2$—$CO_2R^{11}$, a non-nucleophilic base, and a compound of Formula VIa:

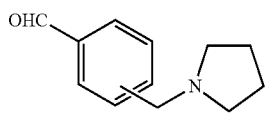
(VIa)

under conditions suitable to form an intermediate compound. The method also includes the step of forming a second reaction mixture of the intermediate compound and a reducing agent, under conditions suitable to form the compound of Formula IIIa, wherein $R^{11}$ can be $C_1$-$C_6$ alkyl.

In some embodiments, the present invention provides a compound having the structure:

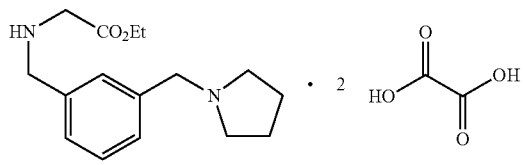 [SMILES: CCOC(=O)CNCc1cccc(CN2CCCC2)c1 ; O=C(O)C(=O)O]

In some embodiments, the present invention provides a method of preparing a compound having the structure:

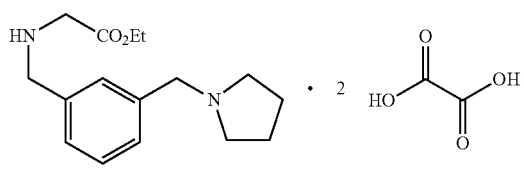 [SMILES: CCOC(=O)CNCc1cccc(CN2CCCC2)c1 ; O=C(O)C(=O)O]

including forming a reaction mixture of oxalic acid and a compound having the structure:

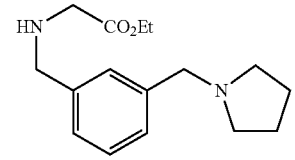 [SMILES: CCOC(=O)CNCc1cccc(CN2CCCC2)c1]

under conditions suitable to prepare the salt.

In some embodiments, the present invention provides a method of preparing a compound of Formula IIa:

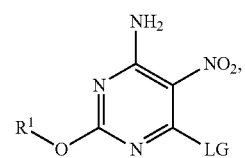
(IIa)

including forming a first reaction mixture of ammonia, a non-nucleophilic base, and a compound of Formula IIb having the structure:

under conditions suitable to form the compound of Formula IIa, wherein $R^1$ can be $C_1$-$C_6$ alkyl, and LG is a leaving group selected from halogen, —OH, or —$OSO_2R^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or $NO_2$.

In some embodiments, the present invention provides a compound of Formula IIe:

(IIe)

wherein $R^1$ of Formula IIe can be $C_1$-$C_6$ alkyl, LG is a leaving group selected from halogen, —OH, or —$OSO_2R^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or $NO_2$, $R^{12}$ can be halogen, —OH or —$NH_2$, subscript x can be 1 or 2, such that when $R^{12}$ is —$NH_2$ and subscript x is 2, then LG is a halogen.

DETAILED DESCRIPTION OF THE INVENTION

I. General

Figure 1:
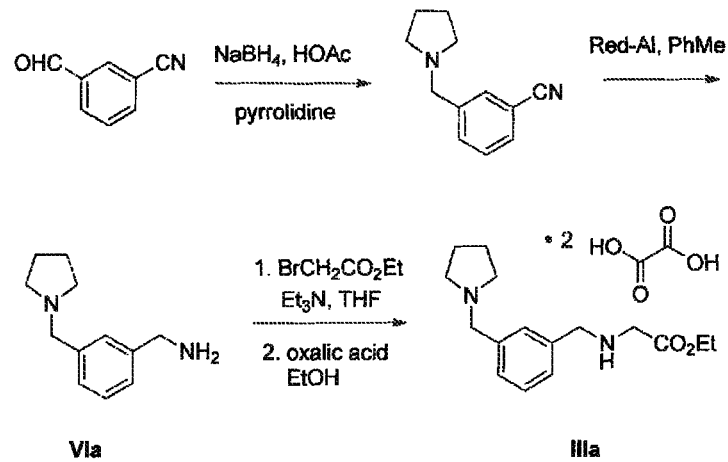
FIG. 1 shows the preparation of the compound of Formula IIIa via alkylation of the compound of Formula Va.
Figure 2:
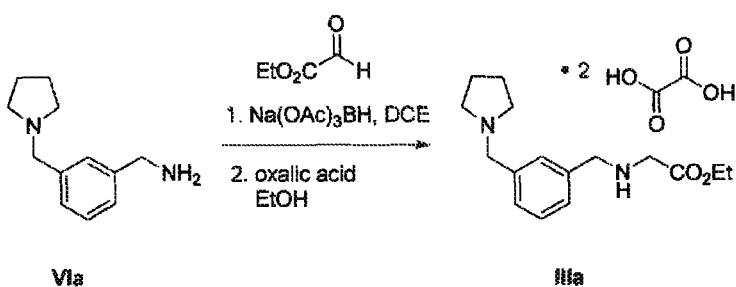
FIG. 2 shows the preparation of the compound of Formula IIIa via reductive amination with the compound of Formula Va.
Figure 3:
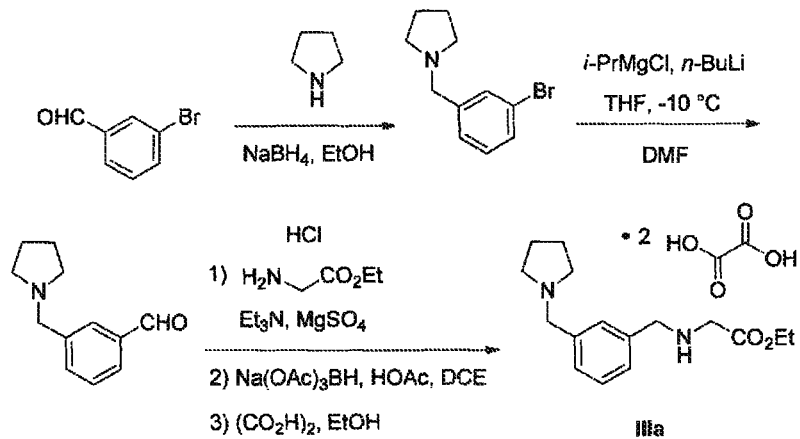
FIG. 3 shows the preparation of the compound of Formula IIIa via reductive amination with the compound of Formula VIa, wherein the compound of Formula VIa is prepared from 3-bromo-benzaldehyde reductive amination using pyrrolidine, followed by Grignard reaction with dimethylformamide to install the aldehyde.
Figure 4:
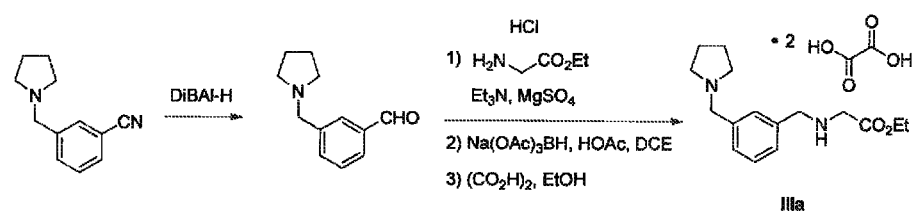
FIG. 4 shows the preparation of the compound of Formula IIIa via reductive amination with the compound of Formula VIa, where the compound of Formula VIa is prepared by reduction of the cyano precursor.
Figure 5:
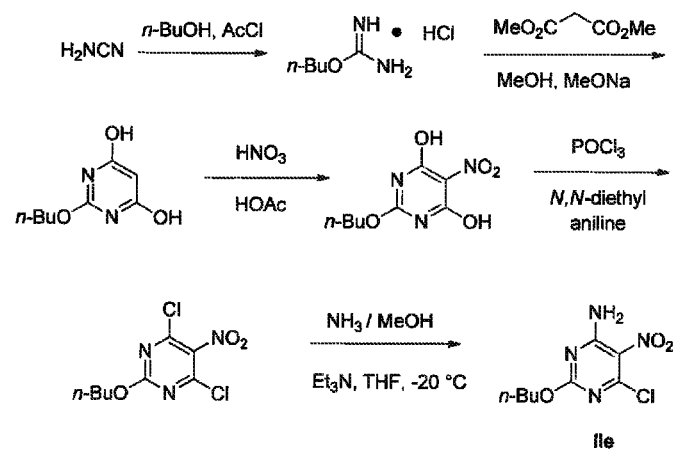
FIG. 5 shows the preparation of the compound of Formula IIe from the dihydroxy derivative by first nitrating the 5-position of the pyrimdine ring, conversion of the 4,6-hydroxy groups to chloro groups, and then conversion of one chloro group to an amine.
Figure 6:
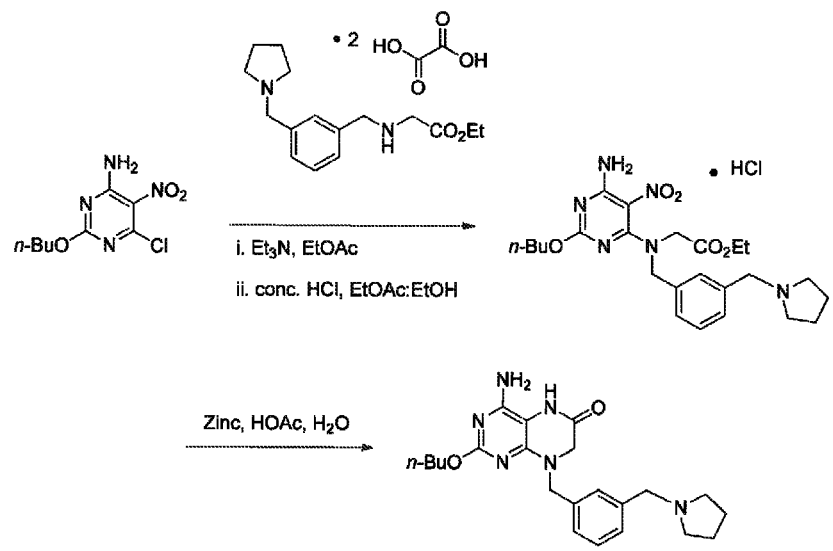
FIG. 6 shows the preparation of the compound of Formula I by coupling the compound of Formula II having a chloro leaving group, with the bis-oxalate salt of the compound of Formula III, followed by ring closure using Zn/HOAc.
Figure 7:
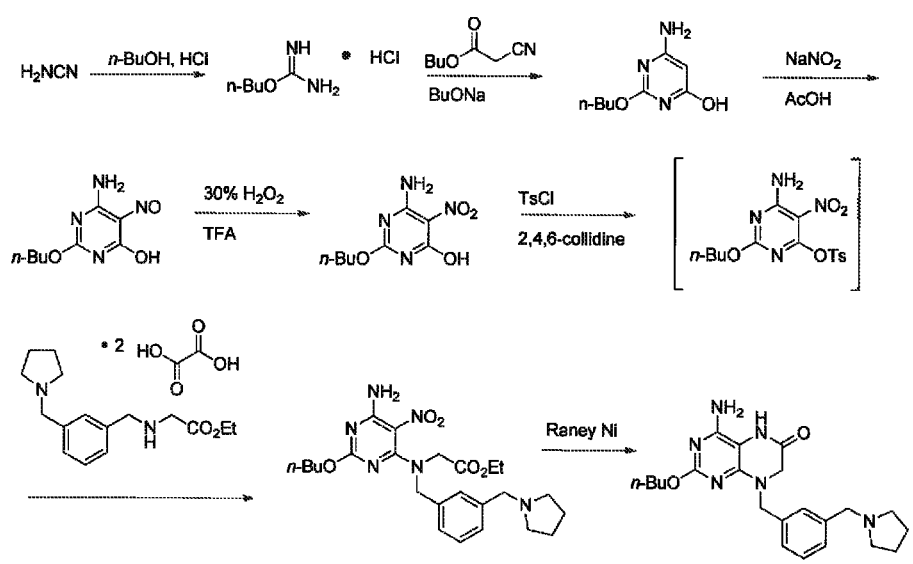
FIG. 7 shows the preparation of the compound of Formula I by coupling the compound of Formula II having an —O-tosyl leaving group formed in situ with tosyl-chloride and 2,4,6-collidine, with the bis-oxalate salt of the compound of Formula III, followed by ring closure using Raney/Ni. Preparation of the compound of Formula II is also shown.

The present invention provides a method of making compounds of Formula I, such as 4-amino-2-butoxy-8-(3-(pyrrolidin-1-ylmethyl)benzyl)-7,8-dihydropteridin-6(5H)-one. Several different methods can be used. For example, compounds of Formula II, such as 2-n-butoxy-6-chloro-5-nitropyrimidin-4-amine, can be combined with compounds of Formula III, such as, ethyl N-(3-pyrrolidin-1-ylmethyl) benzyl glycinate bis-oxalate, to form intermediates of Formula IV, which are then modified to form the compounds of Formula I. The present invention also provides methods for preparing the compounds of Formula II, Formula III and Formula IV.

II. Definitions

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Non-nucleophilic base" refers to an electron donor, a Lewis base, such as nitrogen bases including triethylamine, diisopropylethyl amine, N,N-diethylaniline, pyridine, 2,6-lutidine, 2,4,6-collidine, 4-dimethylaminopyridine, and quinuclidine.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, acetonitrile and dimethyl sulfoxide. Representative non-polar solvents include alkanes (pentanes, hexanes, etc.), cycloalkanes (cyclopentane, cyclohexane, etc.), benzene, toluene, and 1,4-dioxane. Other solvents are useful in the present invention.

"Reducing agent" refers to an agent capable of reducing an atom from a higher oxidation state to a lower oxidation state. Reducing agents can include, but are not limited to, zinc, iron, Raney nickel, sodium sulfide, sodium dithionite, ammonium sulfide, palladium on carbon, and hydrogen donors such as lithium aluminum hydride, sodium borohydride and sodiumtriacetoxyborohydride.

"Leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, mesylate, tosylate, triflate, 4-nitrobenzenesulfonate, 4-chlorobenzenesulfonate, etc. One of skill in the art will recognize other leaving groups useful in the present invention.

"Nitration agent" refers to a reagent capable of adding a nitro group, —$NO_2$, to a compound. Representative nitration agents include, but are not limited to, nitric acid.

"Chlorination agent" refers to a reagent capable of adding a chloro group, —Cl, to a compound. Representative chlorination agents include, but are not limited to, phosphorous oxychloride, thionyl chloride, oxalyl chloride and sulfuryl chloride.

"Alkyl" refers to a straight or branched acyclic hydrocarbon containing normal, secondary, or tertiary carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (s-Pn, s-Pentyl, —$CH(CH_3)CH_2CH_2CH_3$), 3-pentyl (—$CH(CH_2CH_3)_2$), 2-methyl-2-butyl (t-Pn, t-Pentyl, —$C(CH_3)_2CH_2CH_3$), 3-methyl-2-butyl (neo-Pn, neo-Pentyl, —$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkenyl" refers to a hydrocarbon containing normal, secondary, or tertiary carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethenyl, vinyl (—CH=$CH_2$), allyl (—$CH_2$CH=$CH_2$), and 5-hexenyl (—$CH_2CH_2CH_2CH_2$CH=$CH_2$).

"Alkynyl" refers to a hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain hydrocarbon group having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene groups include, but are not limited to, methylene (—$CH_2$—), 1,1-ethylene (—CH($CH_3$)—), 1,2-ethylene (—$CH_2CH_2$—), 1,1-propylene (—CH($CH_2CH_3$)—), 1,2-propylene (—$CH_2$CH($CH_3$)—), 1,3-propylene (—$CH_2CH_2CH_2$—), 1,4-butylene (—$CH_2CH_2CH_2C_2$—), and the like.

"Alkenylene" refers to an unsaturated, branched or straight chain hydrocarbon group having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene groups include, but are not limited to, 1,2-ethylene (—CH=CH—).

"Alkynylene" refers to an unsaturated, branched or straight chain hydrocarbon group having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene groups include, but are not limited to, acetylene (—C≡C—), propargylene (—$CH_2$C≡C—), and 4-pentynylene (—$CH_2CH_2CH_2$C≡C—).

"Alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—C($CH_3$)$_3$or —OtBu), and the like.

"Halogen" refers to F, Cl, Br, or I.

"Haloalkyl" refers to an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Haloalkoxy" refers to a group —$OR^a$, where $R^a$ is a haloalkyl group as herein defined. As non-limiting examples, haloalkoxy groups include —$OCH_2$F, —$OCHF_2$, and —$OCF_3$.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —N($CH_3$)$_2$, and the like), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2$N($CH_3$)$_2$, and the like), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heteroalkylene" refers to a heteroalkyl group having two monovalent radical centers derived by the removal of two hydrogen atoms from the same or two different atoms of a parent heteroalkane. For example, a heteroalkylene group can have 1 to 20 carbon atoms, 1 to 10 carbon atoms, or 1 to 6 carbon atoms.

"Carbocycle" or "carbocyclyl" or "cycloalkyl" refers to a saturated, partially unsaturated, non-aromatic ring having from 3 to 20 ring atoms. For example, the carbocycle can have 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Carbocycles includes non-aromatic mono-, bi-, and poly-cyclic rings, whether fused, bridged, or spiro. Carbocycle can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$ $C_{3-11}$, and $C_{3-12}$. Saturated monocyclic carbocycle rings include, for example, cyclopropyl, cyclobutyl, cyclopentyl, cyclohexyl, and cyclooctyl. Saturated bicyclic and polycyclic carbocycle rings include, for example, norbornane, [2.2.2] bicyclooctane, decahydronaphthalene and adamantane. Carbocycle groups can also be partially unsaturated, having one or more double or triple bonds in the ring. Representative carbocycle groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When carbocycle is a saturated monocyclic $C_{3-8}$ carbocycle, exemplary groups include, but are not limited to cyclopropyl, cyclobutyl, cyclopentyl, cyclohexyl, cycloheptyl and cyclooctyl. When carbocycle is a saturated monocyclic $C_{3-6}$ carbocycle, exemplary groups include, but are not limited to cyclopropyl, cyclobutyl, cyclopentyl, and cyclohexyl. Carbocycle groups can be substituted or unsubstituted.

"Carbocyclylene" refers to a carbocyclyl or carbocycle as defined above having two monovalent radical centers derived by the removal of two hydrogen atoms from the same or two different carbon atoms of a parent carbocyclyl.

"Carbocyclylalkyl" refers to an acyclic alkyl group in which one of the hydrogen atoms bonded to a carbon atom, typically a terminal or sp3 carbon atom, is replaced with a carbocyclyl group as defined above. Typical carbocyclylalkyl groups include, but are not limited to the cycloalkylalkyl groups such as cyclopropylmethyl, cyclobutylethyl, cyclohexylmethyl and the like. The cycloalkylalkyl group can comprise 4 to 20 carbon atoms, e.g., the alkyl moiety is 1 to 6 carbon atoms and the cycloalkyl group is 3 to 14 carbon atoms.

"Carbocyclylheteroalkyl" refers to a heteroalkyl as defined herein, in which a hydrogen atom, which may be attached either to a carbon atom or a heteroatom, has been replaced with a carbocyclyl group as defined herein. The carbocyclyl groups can be bonded to a carbon atom of the heteroalkyl group, or to a heteroatom of the heteroalkyl group, provided that the resulting carbocyclylheteroalkyl group provides a chemically stable moiety.

"Heterocycle" or "heterocyclyl" or "heterocycloalkyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, P or S). The terms "heterocycle" or "heterocyclyl" includes saturated rings, and partially unsaturated rings. Heterocycles includes non-aromatic mono-, bi-, and polycyclic rings, whether fused, bridged, or spiro.

Heterocycle groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Other suitable sizes of heterocycle groups include 3 to 20 ring atoms, 3 to 18, or 3 to 15 ring atoms. Any suitable number of heteroatoms can be included in the heterocycle groups, such as 1, 2, 3, or 4, or 1 to 2, 1 to 3, 1 to 4, 2 to 3, 2 to 4, or 3 to 4. The heterocycle group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycle groups can also be fused to aromatic or non-aromatic ring systems to form members including, but not limited to, indoline. Heterocycle groups can be unsubstituted or substituted. For example, heterocycle groups can be substituted with $C_{1-6}$ alkyl or oxo (=O), among many others.

When heterocycle includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycle can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocyclylene" refers to a heterocyclyl or heterocycle as defined above having two monovalent radical centers derived by the removal of two hydrogen atoms from the same or two different atoms of a parent heterocyclyl.

"Heterocyclylalkyl" refers to an acyclic alkyl group in which one of the hydrogen atoms bonded to a carbon atom, typically a terminal or sp3 carbon atom, is replaced with a heterocyclyl group (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Thus, the heterocyclylalkyl group can have from 4 to 20 carbon and heteroatoms. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 6-membered sulfur, oxygen, and/or nitrogen containing heterocycles such as piperidinylmethyl, piperazinylmethyl, morpholinylmethyl, and the like.

"Heterocyclylheteroalkyl" refers to an acyclic heteroalkyl group defined above in which one of the hydrogen atoms bonded to a carbon or heteroatom, is replace with a heterocyclyl group. The heterocyclylheteroalkyl group can comprise 6 to 20 atoms, e.g., the heteroalkyl moiety is 2 to 6 atoms and the heterocyclyl moiety is 5 to 12 atoms.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Arylene" refers to an aryl as defined above having two monovalent radical centers derived by the removal of two hydrogen atoms from the same or two different carbon atoms of a parent aryl. Typical arylene groups include, but are not limited to, phenylene.

"Arylalkyl" refers to an acyclic alkyl group in which one of the hydrogen atoms bonded to a carbon atom, typically a terminal or sp3 carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylheteroalkyl" refers to a heteroalkyl as defined herein, in which a hydrogen atom, which may be attached either to a carbon atom or a heteroatom, has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, and the like. In addition, any of the alkylene moieties in the general formulae above can be further substituted with any of the substituents defined or exemplified herein.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl also includes monovalent aromatic heterocyclyl comprising an aryl moiety and a heteroaryl group. Non limiting examples of these heteroaryls are:

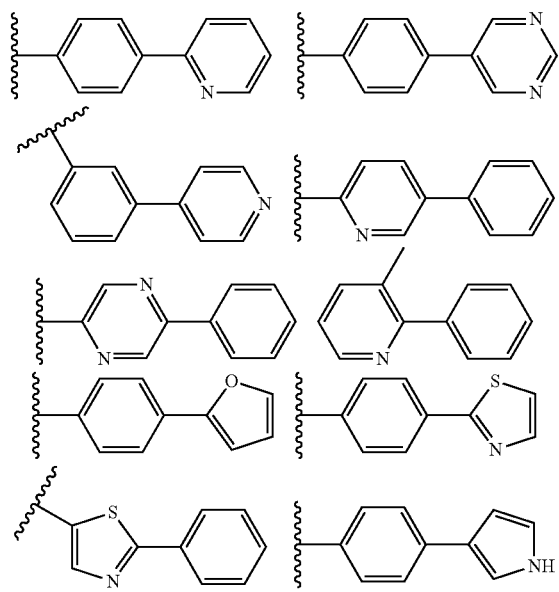

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH)-pyridazyl, —CH(CH$_3$)-pyrimidyl, —CH(CH$_3$)-pyrazyl, and the like.

"Heteroarylheteroalkyl" refers to a heteroalkyl group, as defined herein, in which a hydrogen atom has been replaced with a heteroaryl group as defined herein. The heteroarylheteroalkyl group can comprise 6 to 20 atoms, e.g., the heteroalkyl moiety is 2 to 6 atoms and the heteroaryl moiety is 5 to 12 atoms.

"Amino" refers to an —NR'R" group, where R' and R" can be any suitable substituent, such as hydrogen or alkyl.

"Ammonia" refers to NH$_3$.

"Azido" refers to —N=N$^+$=N$^-$ or —N$_3$.

"Cyano" refers to —CN.

"Hydroxyl" refers to —OH.

"Nitro" refers to —NO$_2$.

"Aldehyde" refers to —CHO or —C(O)H, and can be written in reverse for chemical structures: "OHC—" or "H(O)C—".

"Ketone" refers to —COR or —C(O)R, and can be written in reverse for chemical structures: "ROC—" or "R(O)C—".

"Ester" refers to —CO$_2$R or —C(O)OR, and can be written in reverse for chemical structures: "RO$_2$C—" or "RO(O)C—".

"Kilogram scale" refers to a reaction performed where at least one of the reagents used is in an amount of at least 1 kilogram.

III. Compounds

The methods of the present invention can be used to prepare compounds of Formula I:

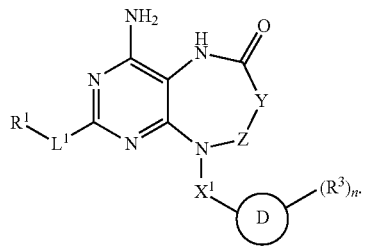

In some embodiments, groups Z—Y of Formula I can be —$CR^4R^5$—, —$CR^4R^5$—$CR^4R^5$—, —$C(O)CR^4R^5$—, —$CR^4R^5C(O)$—, —$NR^8C(O)$—, —$C(O)NR^8$—, —$CR^4R^5S(O)_2$—, or —$CR^5=CR^5$—. In some embodiments, groups Z—Y of Formula I can be —$CR^4R^5$— or —$CR^4R^5$—$CR^4R^5$—. In some embodiments, groups Z—Y of Formula I can be —$CR^4R^5$—. In some embodiments, groups Z—Y of Formula I can be —$CH_2$—, —$CH(CH_3)$— or —$CH_2CH_2$—. In some embodiments, groups Z—Y of Formula I can be —$CH_2$—.

In some embodiments, group $L^1$ of Formula I can be —$NR^8$—, —O—, —S—, —$S(O)_2$—, —$S(O)$—, or a covalent bond. In some embodiments, group $L^1$ of Formula I can be —$NR^8$—, —O—, or a covalent bond. In some embodiments, group $L^1$ of Formula I can be —$NR^8$—, or —O—. In some embodiments, group $L^1$ of Formula I can be —NH— or —O—. In some embodiments, group $L^1$ of Formula I can be —O—.

In some embodiments, group $R^1$ of Formula I can be alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclyl heteroalkyl, substituted heterocyclylheteroalkyl, arylheteroalkyl, substituted arylheteroalkyl, heteroarylheteroalkyl, or substituted heteroarylheteroalkyl. In some embodiments, group $R^1$ of Formula I can be $C_1$-$C_6$ alkyl, substituted $C_1$-$C_6$ alkyl, $C_1$-$C_6$ haloalkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ heteroalkyl, substituted $C_1$-$C_6$ heteroalkyl, $C_3$-$C_{20}$ carbocyclyl, substituted $C_3$-$C_{20}$ carbocyclyl, $C_4$-$C_{20}$ carbocyclylalkyl, substituted $C_4$-$C_{20}$ carbocyclylalkyl, $C_3$-$C_{20}$ heterocyclyl, substituted $C_3$-$C_{20}$ heterocyclyl, $C_4$-$C_{20}$ heterocyclylalkyl, or substituted $C_4$-$C_{20}$ heterocyclylalkyl, $C_6$-$C_{20}$ arylalkyl, substituted $C_6$-$C_{20}$ arylalkyl, $C_6$-$C_{20}$ heteroarylalkyl, substituted $C_6$-$C_{20}$ heteroarylalkyl, $C_4$-$C_{20}$ carbocyclylheteroalkyl, substituted $C_4$-$C_{20}$ carbocyclylheteroalkyl, $C_4$-$C_{20}$ heterocyclyl heteroalkyl, substituted $C_4$-$C_{20}$ heterocyclyl heteroalkyl, $C_6$-$C_{20}$ arylheteroalkyl, substituted $C_6$-$C_{20}$ arylheteroalkyl, $C_6$-$C_{20}$ heteroarylheteroalkyl, or substituted $C_6$-$C_{20}$ heteroarylheteroalkyl.

In some embodiments, group $R^1$ of Formula I can be alkyl, substituted alkyl, haloalkyl, alkenyl, substituted alkenyl, alkynyl, substituted alkynyl, substituted or unsubstituted $C_1$-$C_6$ heteroalkyl containing one or more heteroatoms (selected from N, O, or S), cyclopropyl, substituted cyclopropyl, cyclobutyl, substituted cyclobutyl, cyclopentyl, substituted cyclopentyl, cyclohexyl, substituted cyclohexyl, bicyclo[3.1.0]cyclohexyl, tetrahydropyranyl, substituted tetrahydropyranyl, furanyl, substituted furanyl, pyrrolidinyl, or substituted pyrrolidinyl. In some embodiments, the group $R^1$ of Formula I can be alkyl, substituted alkyl, $C_1$-$C_6$ substituted or unsubstituted heteroalkyl containing one or more heteroatoms (selected from N, O and S), cyclopropyl, substituted cyclopropyl, cyclobutyl, substituted cyclobutyl, cyclopentyl, substituted cyclopentyl, cyclohexyl, substituted cyclohexyl, bicyclo[3.1.0]cyclohexyl, tetrahydropyranyl, substituted tetrahydropyranyl, furanyl, substituted furanyl, pyrrolidinyl, or substituted pyrrolidinyl. In some embodiments, group $R^1$ of Formula I can be alkyl, substituted alkyl, haloalkyl, alkenyl, substituted alkenyl, alkynyl, substituted alkynyl, $C_1$-$C_6$ substituted or unsubstituted heteroalkyl containing one or more heteroatoms (selected from N, O, or S), cyclopropyl, substituted cyclopropyl, cyclobutyl, substituted cyclobutyl, cyclopentyl, substituted cyclopentyl, cyclohexyl, substituted cyclohexyl, bicyclo[3.1.0]cyclohexyl, tetrahydropyranyl, substituted tetrahydropyranyl, furanyl, substituted furanyl, pyrrolidinyl, or substituted pyrrolidinyl.

In some embodiments, group $R^1$ of Formula I can be alkyl. In some embodiments, group $R^1$ of Formula I can be $C_1$-$C_6$ alkyl. In some embodiments, group $R^1$ of Formula I can be methyl, ethyl, n-propyl, iso-propyl, n-butyl, iso-butyl, sec-butyl, t-butyl, n-pentyl, tert-pentyl, neopentyl, iso-pentyl, sec-pentyl, 3-pentyl, hexyl, and 2-ethyl-butyl. In some embodiments, group $R^1$ of Formula I can be butyl. In some embodiments, group $R^1$ of Formula I can be n-butyl.

In some embodiments, group $X^1$ of Formula I can be $C_1$-$C_6$ alkylene, substituted $C_1$-$C_6$ alkylene, $C_1$-$C_6$ heteroalkylene, substituted $C_1$-$C_6$ heteroalkylene, $C_2$-$C_6$ alkenylene, substituted $C_2$-$C_6$ alkenylene, $C_2$-$C_6$ alkynylene, substituted $C_2$-$C_6$ alkynylene, $C_3$-$C_{20}$ carbocyclylene, substituted $C_3$-$C_{20}$ carbocyclylene, $C_3$-$C_{20}$ heterocyclylene, substituted $C_3$-$C_{20}$ heterocyclylene, —$NR^8$—, —O—, —C(O)—, —S(O)—, $S(O)_2$—, or a bond. In some embodiments, group $X^1$ of Formula I can be alkylene, substituted alkylene, heteroalkylene, substituted heteroalkylene, or a bond. In some embodiments, group $X^1$ of Formula I can be $C_1$-$C_6$ alkylene, substituted $C_1$-$C_6$ alkylene, $C_1$-$C_6$ heteroalkylene, substituted $C_1$-$C_6$ heteroalkylene, or a bond. In some embodiments, group $X^1$ of Formula I can be alkylene. In some embodiments, group $X^1$ of Formula I can be $C_1$-$C_6$ alkylene. In some embodiments, group $X^1$ of Formula I can be $C_1$-$C_6$ alkylene, $C_1$-$C_6$ heteroalkylene or $C_1$-$C_6$ substituted heteroalkylene. In some embodiments, group $X^1$ of Formula I can be $C_1$-$C_6$ alkylene. In some embodiments, group $X^1$ of Formula I can be —$CH_2$— or —$CH(CH_3)$—. In some embodiments, group $X^1$ of Formula I can be methylene.

In some embodiments, group D of Formula I can be carbocyclyl, substituted carbocyclyl, heterocyclyl or substituted heterocyclyl wherein the carbocyclyl, substituted carbocyclyl, heterocyclyl or substituted heterocyclyl can be substituted with one or two -$L^2$-$NR^6R^7$, or D can be a heterocyclyl, substituted heterocyclyl, heteroaryl or substituted heteroaryl wherein the heterocyclyl, substituted heterocyclyl, heteroaryl or substituted heteroaryl comprises one to four nitrogen atoms. In some embodiments, group D of Formula I can be $C_3$-$C_{20}$ carbocyclyl, substituted $C_3$-$C_{20}$ carbocyclyl, $C_3$-$C_{20}$ heterocyclyl or substituted $C_3$-$C_{20}$ heterocyclyl wherein the carbocyclyl, substituted carbocyclyl, heterocyclyl or substituted heterocyclyl can be substituted with one or two -$L^2$-$NR^6R^7$, or D can be a $C_3$-$C_{20}$ heterocyclyl, substituted $C_3$-$C_{20}$ heterocyclyl, $C_5$-$C_{20}$ heteroaryl or substituted $C_5$-$C_{20}$ heteroaryl wherein the heterocyclyl, substituted heterocyclyl, heteroaryl or substituted heteroaryl comprises one to four nitrogen atoms. In some embodiments, group D of Formula I can be carbocyclyl, substituted carbocyclyl, heterocyclyl or substituted heterocyclyl wherein the carbocyclyl, substituted carbocyclyl, heterocyclyl or substituted heterocyclyl can be substituted with one or two -$L^2$-$NR^6R^7$ groups. In some embodiments, group D of Formula I can be phenyl, biphenyl, or pyridinyl, wherein the phenyl, biphenyl, or pyridinyl can be substituted with one or two -$L^2$-$NR^6R^7$. In some embodiments, group D of Formula I can be phenyl, biphenyl or pyridinyl, wherein the phenyl, biphenyl or pyridinyl can be substituted with -$L^2$-$NR^6R^7$; or D can be pyridinyl, piperidinyl, piperazinyl or 1,2,3,4-tetrahydroisoquinolinyl, wherein the pyridinyl, piperidinyl, piperazinyl or 1,2,3,4-tetrahydroisoquinolinyl can be substituted with one or two -$L^2$-$NR^6R^7$; or group D can be pyridinyl, piperidinyl, piperazinyl or 1,2,3,4-tetrahydroisoquinolinyl. In some embodiments, group D of Formula I can be phenyl or biphenyl, wherein the phenyl or biphenyl can be substituted with -$L^2$-$NR^6R^7$. In some embodiments, group D of Formula I can be phenyl, wherein the phenyl can be substituted with -$L^2$-$NR^6R^7$.

In some embodiments, each group $L^2$ of Formula I can independently be alkylene, substituted alkylene, heteroalkylene, substituted heteroalkylene, or a covalent bond. In some embodiments, each group $L^2$ of Formula I can independently be $C_1$-$C_6$ alkylene, substituted $C_1$-$C_6$ alkylene, $C_1$-$C_6$ heteroalkylene, substituted $C_1$-$C_6$ heteroalkylene, or a covalent bond.

In some embodiments, group $L^2$ of Formula I can be $C_1$-$C_6$ alkylene or a covalent bond. In some embodiments, group $L^2$ of Formula I can be alkylene. In some embodiments, group $L^2$ of Formula I can be $C_1$-$C_6$ alkylene. In some embodiments, group $L^2$ of Formula I can be —$CH_2$— or —$CH(CH_3)$—. In some embodiments, group $L^2$ of Formula I can be methylene.

In some embodiments, each group $R^3$ of Formula I can independently be halogen, cyano, azido, nitro, alkyl, substituted alkyl, hydroxyl, amino, heteroalkyl, substituted heteroalkyl, alkoxy, haloalkyl, haloalkoxy, —CHO, —C(O)$OR^8$, —S(O)$R^8$, —S(O)$_2R^8$, —C(O)$NR^9R^{10}$, —N($R^9$)C(O)$R^8$, carbocyclyl, substituted carbocyclyl, carbocyclylalkyl, substituted carbocyclylalkyl, alkenyl, substituted alkenyl, alkynyl, substituted alkynyl, —S(O)$_2NR^9R^{10}$, —N($R^9$)S(O)$_2$ $R^8$, —N($R^9$)S(O)$_2OR^{10}$, —OS(O)$_2NR^9R^{10}$. In some embodiments, each group $R^3$ of Formula I can independently be halogen, cyano, azido, nitro, $C_1$-$C_6$ alkyl, substituted $C_1$-$C_6$ alkyl, hydroxyl, amino, $C_1$-$C_6$ heteroalkyl, substituted $C_1$-$C_6$ heteroalkyl, $C_1$-$C_6$ alkoxy, $C_1$-$C_6$ haloalkyl, $C_1$-$C_6$ haloalkoxy, —CHO, —C(O)$OR^8$, —S(O)$R^8$, —S(O)$_2$ $R^8$, —C(O)$NR^9R^{10}$, —N($R^9$)C(O)$R^8$, carbocyclyl, substituted $C_3$-$C_{20}$ carbocyclyl, $C_4$-$C_{20}$ carbocyclylalkyl, substituted $C_4$-$C_{20}$ carbocyclylalkyl, $C_2$-$C_6$ alkenyl, substituted $C_2$-$C_6$ alkenyl, $C_2$-$C_6$ alkynyl, substituted $C_2$-$C_6$ alkynyl, —S(O)$_2NR^9R^{10}$, —N($R^9$)S(O)$_2R^8$, —N($R^9$)S(O)$_2OR^{10}$, —OS(O)$_2NR^9R^{10}$. In some embodiments, group $R^3$ of Formula I can be cyano or —CHO.

In some embodiments, group n of Formula I can be 0, 1, 2, 3, 4 or 5. In some embodiments, group n of Formula I can be 0 or 1. In some embodiments, group n of Formula I can be 0.

In some embodiments, each recitation of groups $R^4$ and $R^5$ of Formula I can each independently be H, alkyl, substituted alkyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, cyano, azido, $OR^8$, —C(O)H, —C(O)$R^8$, —S(O)$R^8$, —S(O)$_2R^8$, —C(O)$OR^8$, or —C(O)$NR^9R^{10}$; or $R^4$ and $R^5$, taken together with the carbon to which they are both attached, can form a carbocycle, substituted carbocycle, heterocycle or substituted heterocycle; or $R^4$ and $R^5$, when on the same carbon atom, can be taken together with the carbon to which they are attached to form —C(O)— or —C($NR^8$)—; or two $R^4$ or two $R^5$ groups on adjacent carbon atoms when taken together with the carbons to which they are attached can form a 3 to 6 membered carbocycle, substituted carbocycle, heterocycle or substituted heterocycle. In some embodiments, each recitation of groups $R^4$ and $R^5$ of Formula I can each independently be H, $C_1$-$C_6$ alkyl, substituted $C_1$-$C_6$ alkyl, $C_1$-$C_6$ haloalkyl, $C_1$-$C_6$ heteroalkyl, substituted $C_1$-$C_6$ heteroalkyl, $C_3$-$C_{20}$ carbocyclyl, substituted $C_3$-$C_{20}$ carbocyclyl, $C_4$-$C_{20}$ carbocyclylalkyl, substituted $C_4$-$C_{20}$ carbocyclylalkyl, $C_3$-$C_{20}$ heterocyclyl, substituted $C_3$-$C_{20}$ heterocyclyl, $C_4$-$C_{20}$ heterocyclylalkyl, substituted $C_4$-$C_{20}$ heterocyclylalkyl, $C_6$-$C_{20}$ arylalkyl, substituted $C_6$-$C_{20}$ arylalkyl, $C_6$-$C_{20}$ heteroarylalkyl, substituted $C_6$-$C_{20}$ heteroarylalkyl, $C_4$-$C_{20}$ carbocyclylheteroalkyl, substituted $C_4$-$C_{20}$ carbocyclylheteroalkyl, $C_4$-$C_{20}$ heterocyclylheteroalkyl, substituted $C_4$-$C_{20}$ heterocyclylheteroalkyl, $C_6$-$C_{20}$ arylheteroalkyl, substituted $C_6$-$C_{20}$ arylheteroalkyl, $C_6$-$C_{20}$ heteroarylheteroalkyl, or substituted $C_6$-$C_{20}$ heteroarylheteroalkyl, cyano, azido, $OR^8$, —C(O)H, —C(O)$R^8$, —S(O)$R^8$, —S(O)$_2R^8$, —C(O)$OR^8$, or —C(O)$NR^9R^{10}$; or $R^4$ and $R^5$, taken together with the carbon to which they are both attached, can form a $C_3$-$C_{20}$ carbocycle, substituted $C_3$-$C_{20}$ carbocycle, $C_3$-$C_{20}$ heterocycle or substituted $C_3$-$C_{20}$ heterocycle; or $R^4$ and $R^5$, when on the same carbon atom, can be taken together with the carbon to which they are attached to form —C(O)— or —C($NR^8$)—; or two $R^4$ or two $R^5$ groups on adjacent carbon atoms when taken together with the carbons to which they are attached can form a 3 to 6 membered carbocycle, substituted carbocycle, heterocycle or substituted heterocycle.

In some embodiments, each recitation of groups $R^4$ and $R^5$ of Formula I can each independently be H, alkyl, substituted alkyl, haloalkyl, $C_1$-$C_6$ substituted or unsubstituted heteroalkyl containing one or more heteroatoms (selected from N, O, or S), cyano, azido, $OR^8$, —C(O)H, —C(O)$R^8$, —S(O)$R^8$, —S(O)$_2R^8$, —C(O)$OR^8$, or —C(O)$NR^9R^{10}$. In some embodiments, each recitation of groups $R^4$ and $R^5$ of Formula I can each independently be H or $C_1$-$C_6$ alkyl, or can be taken together with the carbon to which they are attached to form —C(O)— or a carbocycle. In some embodiments, each recitation of groups $R^4$ and $R^5$ of Formula I can each independently be H or $C_1$-$C_6$ alkyl, or can be taken together with the carbon to which they are attached to form a carbocycle. In some embodiments, each recitation of groups $R^4$ and $R^5$ of Formula I can each independently be H or $C_1$-$C_6$ alkyl. In some embodiments, each recitation of groups $R^4$ and $R^5$ of Formula I can each independently be H or methyl, or can be taken together with the carbon to which they are attached to form cyclopropane. In some embodiments, each recitation of groups $R^4$ and $R^5$ of Formula I can each independently be H or methyl. In some embodiments, each recitation of groups $R^4$ and $R^5$ of Formula I can each independently be H, or taken together with the carbon to which they are attached can be —C(O)— or cyclopropane. In some embodiments, groups $R^4$ and $R^5$ of Formula I can each independently be H.

In some embodiments, each recitation of groups $R^6$ and $R^7$ of Formula I can each independently be H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, —C(O)H, —C(O)$R^8$, —S(O)$R^8$, —S(O)$_2R^8$, —C(O)O$R^8$, or —C(O)N$R^9R^{10}$, S(O)$_2$N$R^9R^{10}$; or $R^6$ and $R^7$, taken together with the nitrogen to which they are both attached, can form a substituted or unsubstituted heterocycle, which can contain one or more additional heteroatoms selected from N, O, P, or S; or $R^7$ taken together with $L^2$, and the N to which they are both attached, can form a substituted or unsubstituted 3 to 8 membered heterocycle which can contain one or more additional heteroatoms selected from N, O, S, and P. In some embodiments, each recitation of groups $R^6$ and $R^7$ of Formula I can each independently be H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ haloalkyl, $C_1$-$C_6$ heteroalkyl, substituted $C_1$-$C_6$ heteroalkyl, $C_3$-$C_{20}$ carbocyclyl, substituted $C_3$-$C_{20}$ carbocyclyl, $C_4$-$C_{20}$ carbocyclylalkyl, substituted $C_4$-$C_{20}$ carbocyclylalkyl, $C_3$-$C_{20}$ heterocyclyl, substituted $C_3$-$C_{20}$ heterocyclyl, $C_4$-$C_{20}$ heterocyclylalkyl, substituted $C_4$-$C_{20}$ heterocyclylalkyl, $C_6$-$C_{20}$ arylalkyl, substituted $C_6$-$C_{20}$ arylalkyl, $C_6$-$C_{20}$ heteroarylalkyl, substituted $C_6$-$C_{20}$ heteroarylalkyl, $C_4$-$C_{20}$ carbocyclylheteroalkyl, substituted $C_4$-$C_{20}$ carbocyclylheteroalkyl, $C_4$-$C_{20}$ heterocyclylheteroalkyl, substituted $C_4$-$C_{20}$ heterocyclylheteroalkyl, $C_6$-$C_{20}$ arylheteroalkyl, substituted $C_6$-$C_{20}$ arylheteroalkyl, $C_6$-$C_{20}$ heteroarylheteroalkyl, or substituted $C_6$-$C_{20}$ heteroarylheteroalkyl, —C(O)H, —C(O)$R^8$, —S(O)$R^8$, —S(O)$_2R^8$, —C(O)O$R^8$, or —C(O)N$R^9R^{10}$, S(O)$_2$N$R^9R^{10}$; or $R^6$ and $R^7$, taken together with the nitrogen to which they are both attached, can form a substituted or unsubstituted $C_3$-$C_{20}$ heterocycle, which can contain one or more additional heteroatoms selected from N, O, P, or S; or $R^7$ taken together with $L^2$, and the N to which they are both attached, can form a substituted or unsubstituted 3 to 8 membered heterocycle which can contain one or more additional heteroatoms selected from N, O, S, and P.

In some embodiments, each recitation of groups $R^6$ and $R^7$ of Formula I can each independently be H or alkyl; or $R^6$ and $R^7$ taken together with the nitrogen to which they are attached can form a substituted or unsubstituted 4-6 membered heterocycle comprising 0 to 2 additional heteroatoms selected from N, O and S. In some embodiments, groups $R^6$ and $R^7$ of Formula I can be taken together with the nitrogen to which they are attached form an unsubstituted 4-6 membered heterocycle comprising 0 to 2 additional heteroatoms selected from N, O and S. In some embodiments, groups $R^6$ and $R^7$ of Formula I can be taken together with the nitrogen to which they are attached to form an unsubstituted 4-6 membered heterocycle comprising 0 to 2 additional N heteroatoms. In some embodiments, groups $R^6$ and $R^7$ of Formula I can be taken together with the nitrogen to which they are attached to form a heterocycle that can be pyrrolidine, piperidine, or piperazine. In some embodiments, groups $R^6$ and $R^7$ of Formula I can be taken together with the nitrogen to which they are attached to form a heterocycle that can be pyrrolidine or piperidine. In some embodiments, groups $R^6$ and $R^7$ of Formula I can be taken together with the nitrogen to which they are attached to form a heterocycle that can be pyrrolidine.

In some embodiments, each recitation of group $R^8$ of Formula I can be H, alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl. In some embodiments, each recitation of group $R^8$ of Formula I can be H, $C_1$-$C_6$ alkyl, substituted $C_1$-$C_6$ alkyl, $C_1$-$C_6$ haloalkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ heteroalkyl, substituted $C_1$-$C_6$ heteroalkyl, $C_3$-$C_{20}$ carbocyclyl, substituted $C_3$-$C_{20}$ carbocyclyl, $C_4$-$C_{20}$ carbocyclylalkyl, substituted $C_4$-$C_{20}$ carbocyclylalkyl, $C_3$-$C_{20}$ heterocyclyl, substituted $C_3$-$C_{20}$ heterocyclyl, $C_4$-$C_{20}$ heterocyclylalkyl, substituted $C_4$-$C_{20}$ heterocyclylalkyl, $C_6$-$C_{20}$ arylalkyl, substituted $C_6$-$C_{20}$ arylalkyl, $C_6$-$C_{20}$ heteroarylalkyl, substituted $C_6$-$C_{20}$ heteroarylalkyl, $C_4$-$C_{20}$ carbocyclylheteroalkyl, substituted $C_4$-$C_{20}$ carbocyclylheteroalkyl, $C_4$-$C_{20}$ heterocyclylheteroalkyl, substituted $C_4$-$C_{20}$ heterocyclylheteroalkyl, $C_6$-$C_2$ arylheteroalkyl, substituted $C_6$-$C_{20}$ arylheteroalkyl, $C_6$-$C_{20}$ heteroarylheteroalkyl, or substituted $C_6$-$C_{20}$ heteroarylheteroalkyl. In some embodiments, group $R^8$ of Formula I can be H, alkyl, substituted alkyl, haloalkyl, alkenyl, substituted alkenyl, alkynyl, substituted alkynyl, or $C_1$-$C_6$ substituted or unsubstituted heteroalkyl containing one or more heteroatoms (selected from N, O, or S). In some embodiments, group $R^8$ of Formula I can be H, $C_1$-$C_6$ alkyl, substituted $C_1$-$C_6$ alkyl, $C_1$-$C_6$ haloalkyl, $C_2$-$C_6$ alkenyl, substituted $C_2$-$C_6$ alkenyl, $C_2$-$C_6$ alkynyl, substituted $C_2$-$C_6$ alkynyl, or $C_1$-$C_6$ substituted or unsubstituted heteroalkyl containing one or more heteroatoms (selected from N, O, or S).

In some embodiments, each recitation of groups $R^9$ and $R^{10}$ of Formula I can each independently be H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; or $R^9$ and $R^{10}$, taken together with the nitrogen to which they are both bonded, can form a substituted or unsubstituted heterocycle. In some embodiments, each recitation of groups $R^9$ and $R^{10}$ of Formula I can each independently be H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ haloalkyl, $C_1$-$C_6$ heteroalkyl, substituted $C_1$-$C_6$ heteroalkyl, $C_3$-$C_{20}$ carbocyclyl, substituted $C_3$-$C_{20}$ carbocyclyl, $C_4$-$C_{20}$ carbocyclylalkyl, substituted $C_4$-$C_{20}$ carbocyclylalkyl, $C_3$-$C_{20}$ heterocyclyl, substituted $C_3$-$C_{20}$ heterocyclyl, $C_4$-$C_{20}$ heterocyclylalkyl, substituted $C_4$-$C_{20}$ heterocyclylalkyl, $C_6$-$C_{20}$ arylalkyl, substituted C₆-C₂₀ arylalkyl, C₆-C₂₀ heteroarylalkyl, substituted C₆-C₂₀ heteroarylalkyl, C₄-C₂₀ carbocyclylheteroalkyl, substituted C₄-C₂₀ carbocyclylheteroalkyl, C₄-C₂₀ heterocyclylheteroalkyl, substituted C₄-C₂₀ heterocyclylheteroalkyl, C₆-C₂₀ arylheteroalkyl, substituted C₆-C₂₀ arylheteroalkyl, C₆-C₂₀ heteroarylheteroalkyl, or substituted C₆-C₂₀ heteroarylheteroalkyl; or R⁹ and R¹⁰, taken together with the nitrogen to which they are both bonded, can form a substituted or unsubstituted C₃-C₂₀ heterocycle. In some embodiments, each recitation of groups R⁹ and R¹⁰ of Formula I can each independently be H, alkyl, substituted alkyl, alkenyl, substituted alkenyl, alkynyl, substituted alkynyl, haloalkyl, C₁-C₆ substituted or unsubstituted heteroalkyl containing one or more heteroatoms (selected from N, O, or S). In some embodiments, each recitation of groups R⁹ and R¹⁰ of Formula I can each independently be H, C₁-C₆ alkyl, substituted C₁-C₆ alkyl, C₂-C₆ alkenyl, substituted C₂-C₆ alkenyl, C₂-C₆ alkynyl, substituted C₂-C₆ alkynyl, C₁-C₆ haloalkyl, C₁-C₆ substituted or unsubstituted heteroalkyl containing one or more heteroatoms (selected from N, O, or S).

In groups Z—Y, R¹, R³, R⁴, R⁵, R⁶, R⁷, R⁸, R⁹, R¹⁰, L², X¹, X², and D of Formula I, each substituted alkyl, substituted alkenyl, substituted alkynyl, substituted heteroalkyl, substituted carbocyclyl, substituted carbocyclylalkyl, substituted heterocyclyl, substituted heterocyclylalkyl, substituted arylalkyl, substituted heteroarylalkyl, substituted carbocyclylheteroalkyl, substituted heterocyclylheteroalkyl, substituted arylheteroalkyl, substituted heteroarylheteroalkyl, substituted alkylene, substituted heteroalkylene, substituted alkenylene, substituted alkynylene, substituted carbocyclylene, or substituted heterocyclylene can independently be substituted with one to four substituents selected from -halogen, —R, —O—, =O, —OR, —SR, —S—, —NR₂, —N(+)R₃, =NR, —C(halogen)₃, —CR(halogen)₂, —CR₂(halogen), —CN, —OCN, —SCN, —N=C=O, —NCS, —NO, —NO₂, =N₂, —N₃, —NRC(=O)R, —NRC(=O)OR, —NRC(=O)NRR, —C(=O)NRR, —C(=O)OR, —OC(=O)NRR, —OC(=O)OR, —C(=O)R, —S(=O)₂OR, —S(=O)₂R, —OS(=O)₂OR, —S(=O)₂NR, —S(=O)R, —NRS(=O)₂R, —NRS(=O)₂NRR, —NRS(=O)₂OR, —OP(=O)(OR)₂, —P(=O)(OR)₂, —P(O)(OR)(O)R, —C(=O)R, —C(=S)R, —C(=O)OR, —C(=S)OR, —C(=O)SR, —C(=S)SR, —C(=O)NRR, —C(=S)NRR, —C(=NR)NRR, and —NRC(=NR)NRR; wherein each R can independently be H, alkyl, cycloalkyl, aryl, arylalkyl, or heterocyclyl.

In some embodiments, the compound of Formula I can be a compound of Formula Ia:

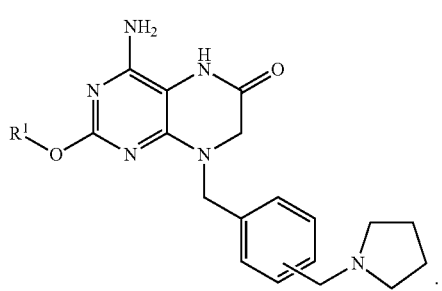

(Ia)

In some embodiments, the compound of Formula I can be a compound of Formula Ib:

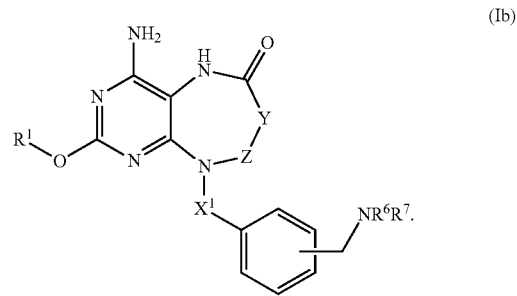

(Ib)

Groups Z—Y, R¹, R⁶, R⁷, and X¹ of Formulas Ia and Ib are as defined above for Formula I.

In some embodiments, the compound of Formula I, Formula Ia or Formula Ib can have the structure:

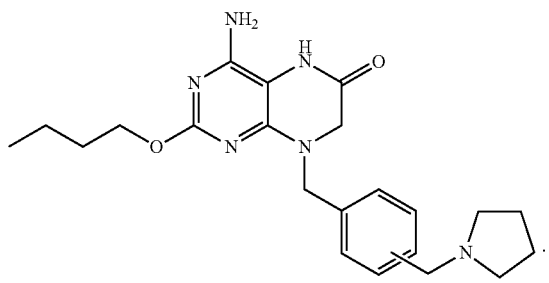

In some embodiments, the compound of Formula I, Formula Ia or Formula Ib can have the structure:

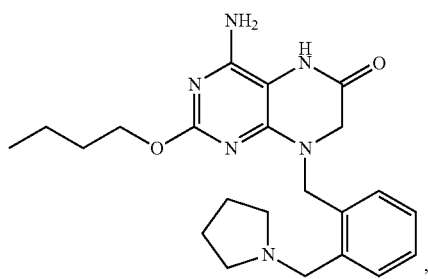

,

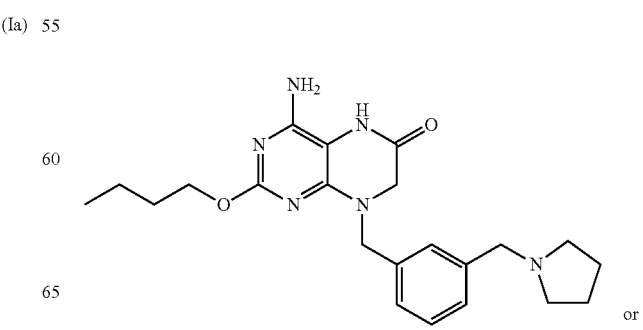

or

-continued

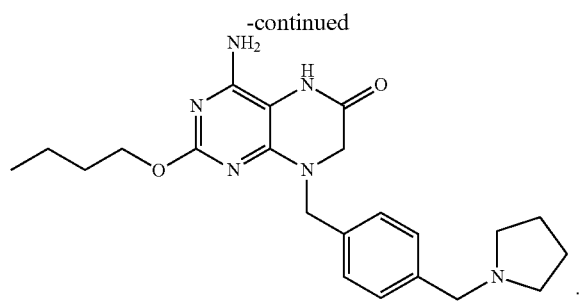

In some embodiments, the compound of Formula I, Formula Ia or Formula Ib can have the structure:

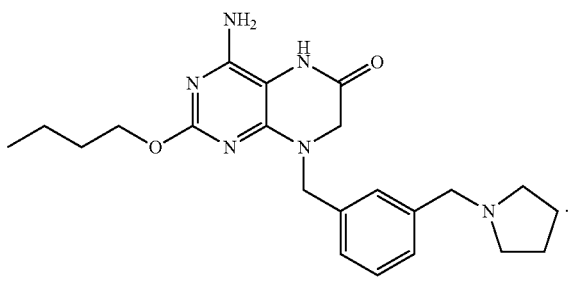 [SMILES: CCCCOc1nc(N)c2c(n1)N(Cc1cccc(CN3CCCC3)c1)CC(=O)N2]

In some embodiments, the compound of Formula I, Formula Ia or Formula Ib can have the structure:

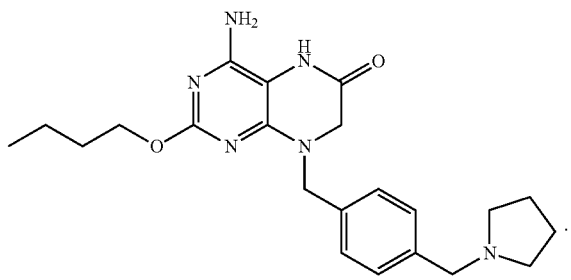 [SMILES: CCCCOc1nc(N)c2c(n1)N(Cc1ccc(CN3CCCC3)cc1)CC(=O)N2]

In some embodiments, the compound of Formula I can be a compound of Formula Ia, wherein group $R^1$ can be alkyl. In some embodiments, group $R^1$ of Formula Ia can be $C_1$-$C_6$ alkyl. In some embodiments, group $R^1$ of Formula Ia can be methyl, ethyl, n-propyl, iso-propyl, n-butyl, iso-butyl, sec-butyl, t-butyl, n-pentyl, tert-pentyl, neopentyl, iso-pentyl, sec-pentyl, 3-pentyl, hexyl, and 2-ethyl-butyl. In some embodiments, group $R^1$ of Formula Ia can be butyl. In some embodiments, group $R^1$ of Formula Ia can be n-butyl.

In some embodiments, the compound of Formula I can be a compound of Formula Ib, wherein group $R^1$ can be alkyl, groups Z—Y can be —$CR^4R^5$— or —$CR^4R^5$—$CR^4R^5$—, group $X^1$ can be alkylene, and groups $R^6$ and $R^7$ can be taken together with the nitrogen to which they are attached form an unsubstituted 4-6 membered heterocycle comprising 0 to 2 additional N heteroatoms. In some embodiments, the compound of Formula I can be a compound of Formula Ib, wherein group $R^1$ can be $C_1$-$C_6$ alkyl, groups Z—Y can be —$CH_2$—, —$CH(CH_3)$— or —$CH_2CH_2$—, group $X^1$ can be $C_1$-$C_6$ alkylene, and groups $R^6$ and $R^7$ can be taken together with the nitrogen to which they are attached to form a heterocycle that can be pyrrolidine or piperidine.

In some embodiments, groups Z—Y of Formula Ib can be —$CR^4R^5$— or —$CR^4R^5$—$CR^4R^5$—. In some embodiments, groups Z—Y of Formula Ib can be —$CR^4R^5$—. In some embodiments, groups Z—Y of Formula Ib can be —$CH_2$—, —$CH(CH_3)$— or —$CH_2CH_2$—. In some embodiments, groups Z—Y of Formula Ib can be —$CH_2$—.

In some embodiments, group $R^1$ of Formula Ib can be alkyl. In some embodiments, group $R^1$ of Formula Ib can be $C_1$-$C_6$ alkyl. In some embodiments, group $R^1$ of Formula Ib can be methyl, ethyl, n-propyl, iso-propyl, n-butyl, iso-butyl, sec-butyl, t-butyl, n-pentyl, tert-pentyl, neopentyl, iso-pentyl, sec-pentyl, 3-pentyl, hexyl, and 2-ethyl-butyl. In some embodiments, group $R^1$ of Formula Ib can be butyl. In some embodiments, group $R^1$ of Formula Ib can be n-butyl.

In some embodiments, group $X^1$ of Formula Ib can be alkylene. In some embodiments, group $X^1$ of Formula Ib can be $C_1$-$C_6$ alkylene. In some embodiments, group $X^1$ of Formula Ib can be —$CH_2$— or —$CH(CH_3)$—. In some embodiments, group $X^1$ of Formula Ib can be methylene.

In some embodiments, groups $R^6$ and $R^7$ of Formula Ib can be taken together with the nitrogen to which they are attached to form an unsubstituted 4-6 membered heterocycle comprising 0 to 2 additional N heteroatoms. In some embodiments, groups $R^6$ and $R^7$ of Formula Ib can be taken together with the nitrogen to which they are attached to form a heterocycle that can be pyrrolidine, piperidine, or piperazine. In some embodiments, groups $R^6$ and $R^7$ of Formula Ib can be taken together with the nitrogen to which they are attached to form a heterocycle that can be pyrrolidine or piperidine. In some embodiments, groups $R^6$ and $R^7$ of Formula Ib can be taken together with the nitrogen to which they are attached to form a heterocycle that can be pyrrolidine.

IV. Method of Preparing Pteridinones of Formula I

The compounds of Formula I can be prepared by a variety of means. For example, the compounds of Formula I can be prepared as described below, via N-arylation of a compound of Formula II with the compound of Formula III, namely ethyl N-[3-pyrrolidin-1-ylmethyl)benzyl]glycinate. The intermediate, Formula IV, can be converted to the compound of Formula I under reducing conditions to close the ring and form the desired compound. The aryl ring of Formula II can include a leaving group such as a chloro or —O-tosyl group. Moreover, the ring closure of Formula IV can be performed with a variety of reducing agents such as Raney nickel or Zn/HOAc.

In some embodiments, the present invention provides a method of making a compound of Formula I:

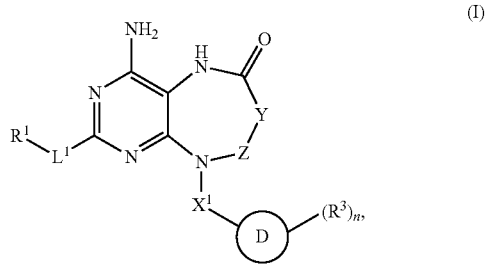

(I)

by forming a first reaction mixture of a compound of Formula II:

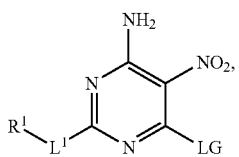

(II)

a non-nucleophilic base, a first solvent, and a compound of Formula III:

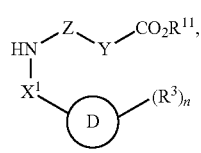

(III)

under conditions suitable to form a compound of Formula IV:

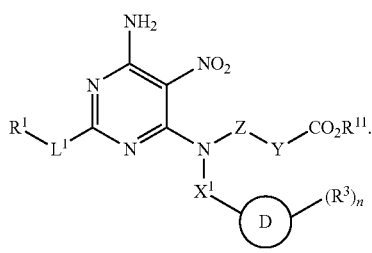

(IV)

The method also includes forming a second reaction mixture of the compound of Formula IV, a second solvent and a reducing agent under conditions suitable to prepare the compound of Formula I.

Groups Z—Y, $R^1$, $R^3$, $L^1$, $X^1$, D, and subscript n, of Formulas I, II, III and IV, are as defined above for the compounds of Formula I. In some embodiments, group $R^{11}$ of Formulas III and IV can be alkyl or alkyl-aryl. In some embodiments, group $R^{11}$ of Formulas III and IV can be $C_1$-$C_6$ alkyl or $C_1$-$C_6$ alkyl-aryl. In some embodiments, group $R^{11}$ of Formulas III and IV can be $C_1$-$C_6$ alkyl. In some embodiments, group $R^{11}$ of Formulas III and IV can be methyl, ethyl, n-propyl, iso-propyl, n-butyl, iso-butyl, sec-butyl, t-butyl, n-pentyl, tert-pentyl, neopentyl, iso-pentyl, sec-pentyl, 3-pentyl, hexyl, and 2-ethyl-butyl. In some embodiments, group $R^{11}$ of Formulas III and IV can be methyl, ethyl or propyl. In some embodiments, group $R^{11}$ of Formulas III and IV can be ethyl. In some embodiments, group $R^{11}$ of Formulas III and IV can be benzyl.

In some embodiments, group LG of Formula II can be any suitable leaving group. In some embodiments, group LG of Formula II can be chloro, bromo, methanesulfonate (—OMs), trifluoromethanesulfonate (—OTf), toluenesulfonate (—OTs or —O-tosyl), 4-nitrobenzenesulfonate, and 4-chlorobenzenesulfonate. In some embodiments, group LG of Formula II can be halogen, —OH, or —$OSO_2R^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or $NO_2$. In some embodiments, group LG of Formula II can be chloro, —OH, or —$OSO_2R^{13}$, wherein $R^{13}$ can be methyl, trifluoromethyl or phenyl, wherein the phenyl can be substituted with 1 $R^{13a}$ group that can be methyl, fluoro, chloro, bromo or $NO_2$. In some embodiments, group LG of Formula II can be chloro, bromo, hydroxy, methanesulfonate, trifluoromethanesulfonate, toluenesulfonate, 4-nitrobenzenesulfonate, and 4-chlorobenzenesulfonate. In some embodiments, group LG of Formula II can be halogen, —OH, or —O-tosyl. In some embodiments, group LG of Formula II can be halogen. In some embodiments, group LG of Formula II can be chloro or bromo. In some embodiments, group LG of Formula II can be chloro. In some embodiments, group LG of Formula II can be chloro, —OH, or —O-tosyl. In some embodiments, group LG of Formula II can be chloro or —OH.

In some embodiments, the compound of Formula II can be a compound of Formula IIa:

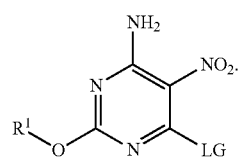

(IIa)

In some embodiments, the compound of Formula II or Formula IIa can have the structure:

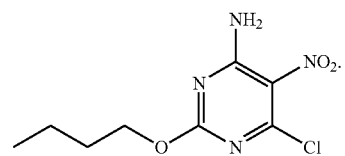

In some embodiments, the compound of Formula II or Formula IIa can have the structure:

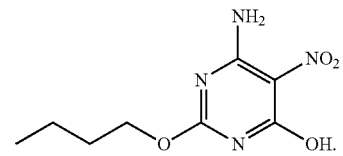 [SMILES: CCCCOc1nc(N)c([N+](=O)[O-])c(O)n1]

In some embodiments, the compound of Formula II or Formula IIa can have the structure:

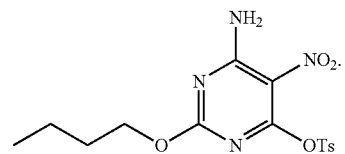

Groups $R^1$ and LG of Formula IIa are as described above for Formula II.

In some embodiments, the compound of Formula III can be a compound of Formula IIIa:

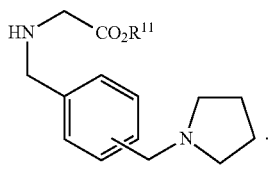
(IIIa)

In some embodiments, the compound of Formula III can be a compound of Formula IIIb:

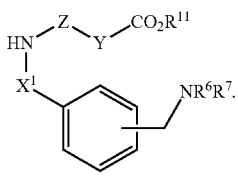
(IIIb)

Groups Z—Y, $R^6$, $R^7$, $R^{11}$, and $X^1$ of Formula IIIa and Formula IIIb are as described above for Formula III.

In some embodiments, the compound of Formula III, Formula IIIa or Formula IIIb can have the structure:

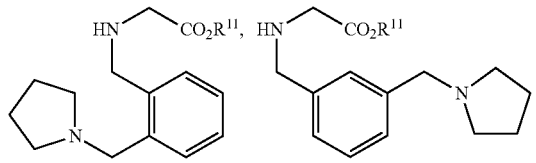 or

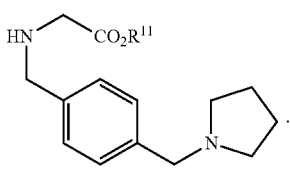

In some embodiments, the compound of Formula III, Formula IIIa or Formula IIIb can have the structure:

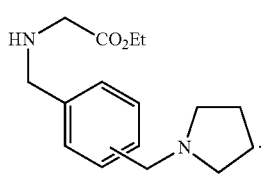

In some embodiments, the compound of Formula III, Formula IIIa or Formula IIIb can have the structure:

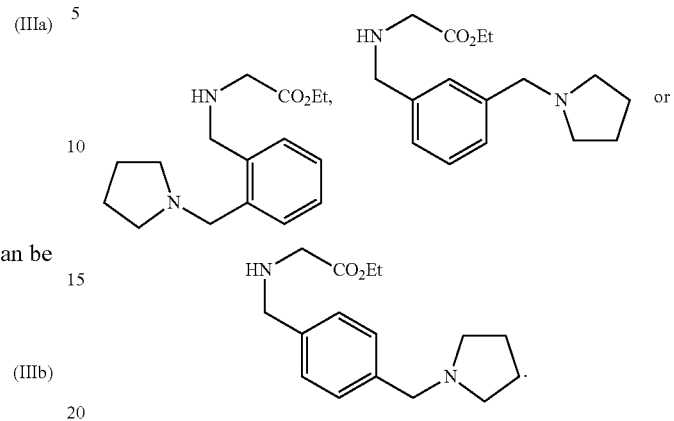 or

In some embodiments, the compound of Formula III, Formula IIIa or Formula IIIb can have the structure:

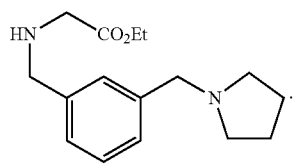 [SMILES: CCOC(=O)CNCc1cccc(CN2CCCC2)c1]

In some embodiments, the compound of Formula III, Formula IIIa or Formula IIIb can have the structure:

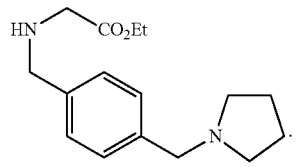

The compound of Formula III, Formula IIIa or Formula IIIb can be in any suitable form. For example, the compound of Formula III, Formula IIIa or Formula IIIb can be in a neutral form or a salt form. Suitable salt forms of the compound of Formula II, Formula IIIa or Formula IIIb include, but are not limited to, inorganic acid addition salts such as chloride, bromide, sulfate, phosphate, and nitrate; organic acid addition salts such as acetate, oxalate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate. In some embodiments, the compound of Formula III, Formula IIIa or Formula IIIb can be a salt. In some embodiments, the compound of Formula III, IIIa or IIIb can be the bis-oxalate salt. In some embodiments, the compound of Formula III, IIIa or IIIb can be the bis-oxalate salt:

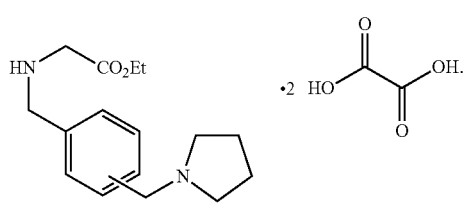

In some embodiments, the compound of Formula III, Formula IIIa or Formula IIIb can be the bis-oxalate salt:

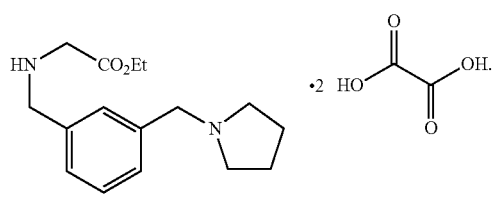 [SMILES: CCOC(=O)CNCc1cccc(CN2CCCC2)c1 ; O=C(O)C(=O)O]

In some embodiments, the compound of Formula IV can be a compound of Formula IVa:

(IVa)

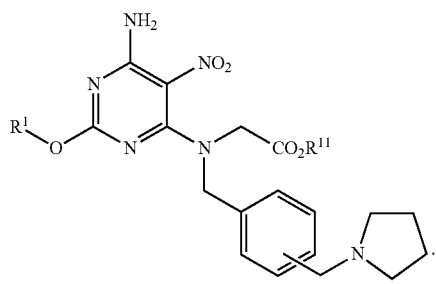

In some embodiments, the compound of Formula IV can be a compound of Formula IVb:

(IVb)

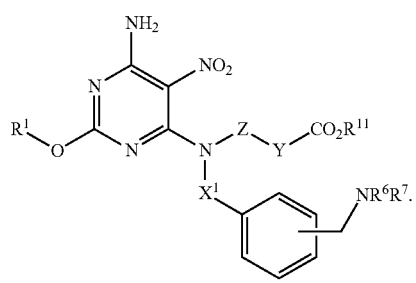

Groups Z—Y, $R^1$, $R^6$, $R^7$, $R^{11}$, and $X^1$ of Formula IVa and Formula IVb are as described above for Formula IV.

In some embodiments, the compound of Formula IV, Formula IVa or Formula IVb can have the structure:

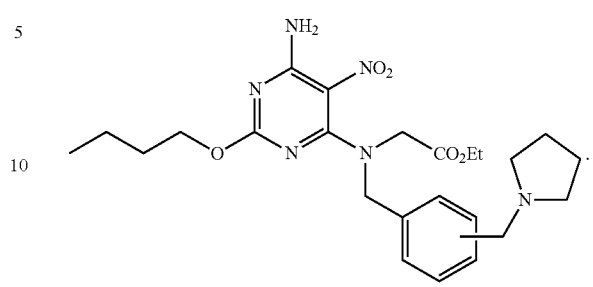

In some embodiments, the compound of Formula IV, Formula IVa or Formula IVb can have the structure:

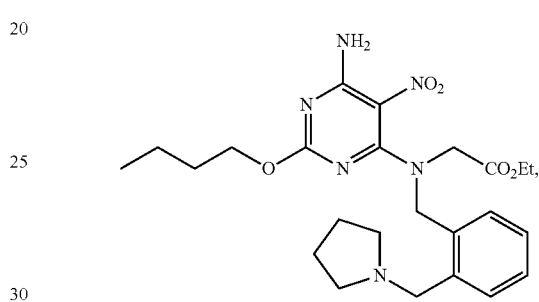

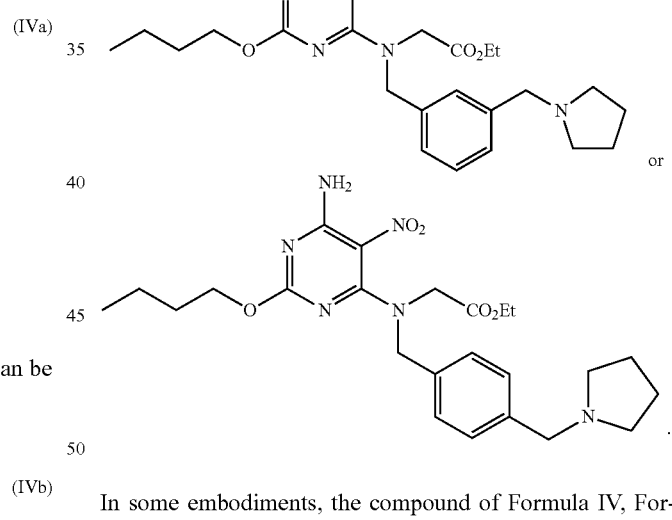

or

In some embodiments, the compound of Formula IV, Formula IVa or Formula IVb can have the structure:

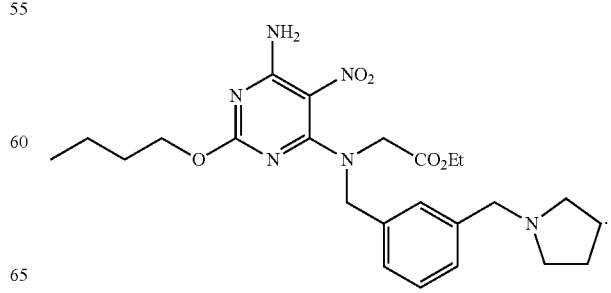

In some embodiments, the compound of Formula IV, Formula IVa or Formula IVb can have the structure:

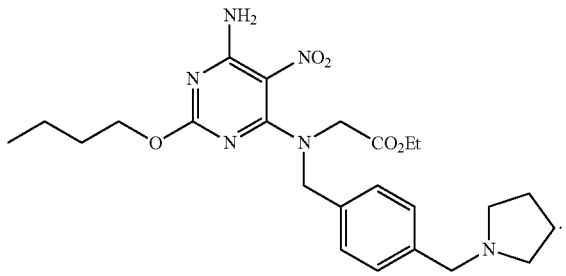 [SMILES: CCCCOc1nc(N)c([N+](=O)[O-])c(N(CC(=O)OCC)Cc2ccc(CN3CCCC3)cc2)n1]

In some embodiments, the present invention provides a method of making a compound of Formula Ia, including the step of forming a first reaction mixture of a compound of Formula IIa, a non-nucleophilic base, a first solvent, and a compound of Formula IIIa, under conditions suitable to form a compound of Formula IVa. The method also includes the step of forming a second reaction mixture of the compound of Formula IVa, a second solvent and a reducing agent under conditions suitable to prepare the compound of Formula Ia. Group $R^1$ of Formulas Ia, IIa and IVa, and $R^{11}$ of Formulas IIIa and IVa can each independently be $C_1$-$C_6$ alkyl; and LG of Formula IIa can be selected from halogen, —OH, and —$OSO_2R^{13}$, wherein $R^{13}$ is selected from the group consisting of $C_1$-$C_6$ alkyl, $C_1$-$C_6$ haloalkyl and aryl, wherein the aryl group is substituted with 1 to 3 $R^{13a}$ groups each independently selected from the group consisting of $C_1$-$C_6$ alkyl, halogen, and $NO_2$.

In some embodiments, the present invention provides a method of making a compound of Formula Ia, including the step of forming a first reaction mixture of a compound of Formula IIa, a non-nucleophilic base, a first solvent, and a compound of Formula IIIa, under conditions suitable to form a compound of Formula IVa. The method also includes the step of forming a second reaction mixture of the compound of Formula IVa, a second solvent and a reducing agent under conditions suitable to prepare the compound of Formula Ia. Group $R^1$ of Formulas Ia, IIa and IVa, and $R^{11}$ of Formulas IIIa and IVa can each independently be $C_1$-$C_6$ alkyl; and LG of Formula IIa can be selected from halogen, —OH, and —O-tosyl. In some embodiments, groups $R^1$ and LG can be as described above.

In some embodiments, the present invention provides a method of making a compound of Formula Ib:

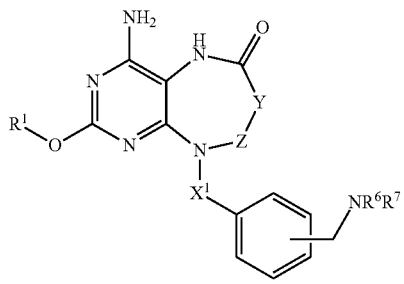

including the step of forming a first reaction mixture of a compound of Formula IIa:

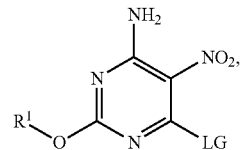

a non-nucleophilic base, a first solvent, and a compound of Formula IIIb:

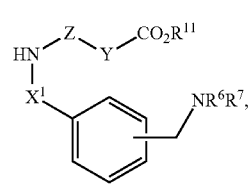

under conditions suitable to form a compound of Formula IVb:

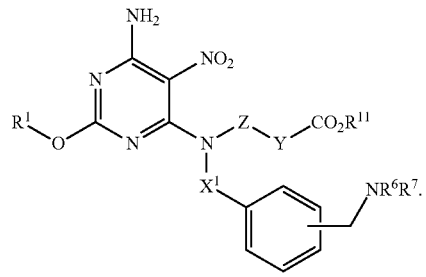

The method also includes the step of forming a second reaction mixture of the compound of Formula IVb, a second solvent and a reducing agent under conditions suitable to prepare the compound of Formula Ib. In some embodiments, groups Z—Y can be —$CR^4R^5$— or —$CR^4R^5$—$CR^4R^5$—, group $R^1$ can be alkyl, group $X^1$ can be alkylene, groups $R^6$ and $R^7$ can be taken together with the nitrogen to which they are attached form an unsubstituted 4-6 membered heterocycle comprising 0 to 2 additional N heteroatoms, group $R^{11}$ can be alkyl, and group LG can be halogen, —OH, or —$OSO_2R^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or $NO_2$. In some embodiments, group $R^1$ can be $C_1$-$C_6$ alkyl, groups Z—Y can be —$CH_2$—, —$CH(CH_3)$— or —$CH_2CH_2$—, group $X^1$ can be $C_1$-$C_6$ alkylene, groups $R^6$ and $R^7$ can be taken together with the nitrogen to which they are attached to form a heterocycle that can be pyrrolidine or piperidine, group $R^{11}$ can be $C_1$-$C_6$ alkyl, and group LG can be selected from chloro, —OH, and —O-tosyl. In some embodiments, groups Z—Y, $R^1$, $R^4$, $R^5$, $R^6$, $R^7$, $R^{11}$, $R^{13}$, $X^1$ and LG can be as described above.

Any suitable non-nucleophilic base can be used in the method of the present invention. In some embodiments, the non-nucleophilic base can be selected from triethylamine, diisopropylethyl amine, N,N-diethylaniline, pyridine, 2,6-lutidine, 2,4,6-collidine, 4-dimethylaminopyridine, and quinuclidine. In some embodiments, the non-nucleophilic base can be selected from triethylamine, diisopropylethyl amine, pyridine, 2,6-lutidine, and 4-dimethylaminopyridine. In some embodiments, the non-nucleophilic base can be triethylamine. In some embodiments, the non-nucleophilic base can be selected from pyridine, 2,6-lutidine, and 2,4,6-collidine. In some embodiments, the non-nucleophilic base can be 2,4,6-collidine.

The first solvent can be any suitable solvent, such as ethyl acetate, isopropyl acetate, tetrahydrofuran, acetonitrile, dimethylformamide, dimethylacetamide, dimethylsulfoxide, or combinations thereof. In some embodiments, the first solvent can be ethyl acetate, isopropyl acetate, tetrahydrofuran, acetonitrile, or combinations thereof. In some embodiments, the first solvent can be ethyl acetate, isopropyl acetate or tetrahydrofuran. In some embodiments, the first solvent can be ethyl acetate. In some embodiments, the first solvent can be ethyl acetate or isopropyl acetate. In some embodiments, the first solvent can be isopropyl acetate. In some embodiments, the first solvent can be tetrahydrofuran, acetonitrile, dimethylformamide, dimethylacetamide or dimethylsulfoxide. In some embodiments, the first solvent can be acetonitrile.

The compound of Formula III, IIIa or IIIb can be any suitable form. In some embodiments, the compound of Formula III, IIIa or IIIb can be the bis-oxalate salt of Formula III, IIIa or IIIb. In some embodiments, the compound of Formula IIIa can be the bis-oxalate salt of Formula IIIa.

The N-arylation step of forming the compound of Formula IV, IVa or IVb can be performed under any suitable reaction conditions. For example, the first reaction mixture can be at any suitable temperature, such as, but not limited to, below room temperature, at room temperature, or above room temperature. In some embodiments, the temperature of the first reaction mixture can be from about −20° C. to about 100° C., or from about 0° C. to about 50° C., or from about 10° C. to about 40° C., or from about 10° C. to about 30° C. In some embodiments, the temperature of the first reaction mixture can be at about 20° C. In some embodiments, the temperature of the first reaction mixture can be from about 0° C. to about 100° C., or from about 25° C. to about 100° C., or from about 50° C. to about 75° C. In some embodiments, the temperature of the first reaction mixture can be at about 60° C.

The N-arylation step of forming the compound of Formula IV, IVa or IVb can be performed for any suitable reaction time. For example, the time reaction can be for minutes, hours or days. In some embodiments, the reaction time can be several hours, such as overnight. The first reaction mixture can also be at any suitable pressure. For example, the first reaction mixture can be below atmospheric pressure, at about atmospheric pressure, or above atmospheric pressure. In some embodiments, the first reaction mixture can be at about atmospheric pressure.

The N-arylation step can prepare the compound of Formula IV, IVa or IVb in any suitable yield. For example, the yield of the compound of Formula IV, IVa or IVb can be at least about 10% from the compound of Formula II or IIa, or at least about 15%, 20, 25, 30, 35, 40, 45, 50, 55, 60, 65, 70, or at least about 75% from the compound of Formula II or IIa. In some embodiments, the yield of Formula IV, IVa or IVb can be at least 25% from the compound of Formula II or IIa. In some embodiments, the yield of Formula IV, IVa or IVb can be at least 35% from the compound of Formula II or IIa. In some embodiments, the yield of Formula IV, IVa or IVb can be at least 50% from the compound of Formula II or IIa. In some embodiments, the yield of Formula IV, IVa or IVb can be at least 75% from the compound of Formula II or IIa.

The compound of Formula IV, IVa or IVb prepared in the N-arylation step can be in any suitable form. For example, the compound of Formula IV, IVa or IVb can be in a neutral form or a salt form. Any salt form of the compound of Formula IV, IVa or IVb can be prepared in the N-arylation step. Suitable salt forms of the compound of Formula IV, IVa or IVb include, but are not limited to, inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate. The salts can be in some cases hydrates or ethanol solvates. In some embodiments, the compound of Formula IV, IVa or IVb can be a salt. In some embodiments, the compound of Formula IV, IVa or IVb can be the hydrochloric salt.

When the compound of Formula IV, IVa or IVb is a salt, the method of the present invention can include an optional step of forming the salt form of the compound of Formula IV. For example, the compound of Formula IV, IVa or IVb can be combined in a reaction mixture with an acid, thereby preparing the salt form of the compound of Formula IV, IVa or IVb. In some embodiments, the method can include forming a reaction mixture of the compound of Formula IV, IVa or IVb and hydrochloric acid to form a monohydrogenchloride form of the compound of Formula IV, IVa or IVb. In some embodiments, the method can include forming a reaction mixture of the compound of Formula IV, IVa or IVb and hydrochloric acid to form the monohydrogenchloride salt of the compound of Formula IV, IVa or IVb. Any suitable solvent can be used in the preparation of the salt form of the compound of Formula IV, IVa or IVb. For example, the solvent can be the same solvent as the first solvent used to prepare the compound of Formula IV, IVa or IVb. In some embodiments, the solvent can be ethyl acetate, isopropyl acetate or tetrahydrofuran, or combinations thereof. In some embodiments, the solvent can be ethyl acetate. In some embodiments, the solvent can be ethyl acetate or isopropyl acetate. In some embodiments, the solvent can be isopropyl acetate.

The second step for preparing the compound of Formula I, Ia or Ib includes a reductive ring closure. The reducing agent of the second step can include any suitable reducing agent capable of reducing the nitro compound and allowing the ring closure to form the compound of Formula I, Ia or Ib. Representative reducing agents include, but are not limited to, zinc, iron, Raney nickel, sodium sulfide, sodium dithionite, ammonium sulfide, palladium on carbon, lithium aluminum hydride, and sodium borohydride. In some embodiments, the reducing agent can be zinc or Raney nickel. In some embodiments, the reducing agent can be zinc. In some embodiments, the reducing agent can be Raney nickel.

The second reaction mixture can include any suitable solvent. For example, the second solvent can be acetic acid, water, methanol, ethanol, isopropanol, tetrahydrofuran, or combinations thereof. In some embodiments, the second solvent can include acetic acid. In some embodiments, the second solvent can include acetic acid and water.

The reducing step of forming the compound of Formula I, Ia or Ib can be performed under any suitable reaction conditions. For example, the second reaction mixture can be at any suitable temperature, such as, but not limited to, below room temperature, at room temperature, or above room temperature. In some embodiments, the temperature of the second reaction mixture can be from about −20° C. to about 100° C., or from about 0° C. to about 50° C., or from about 10° C. to about 30° C. In some embodiments, the temperature of the second reaction mixture can be of from about 10° C. to about 30° C. In some embodiments, the temperature of the second reaction mixture can be at about 20° C.

The reducing step of forming the compound of Formula I, Ia or Ib can be performed for any suitable reaction time. For example, the reaction time can be for minutes, hours or days. In some embodiments, the reaction time can be several hours, such as overnight. The second reaction mixture can also be at any suitable pressure. For example, the second reaction mixture can be below atmospheric pressure, at about atmospheric pressure, or above atmospheric pressure. In some embodiments, the second reaction mixture can be at about atmospheric pressure.

The reducing step can prepare the compound of Formula I, Ia or Ib in any suitable yield. For example, the yield of the compound of Formula I, Ia or Ib can be at least about 10% from the compound of Formula IV, IVa or IVb, or at least about 15%, 20, 25, 30, 35, 40, 45, 50, 55, 60, 65, 70, or at least about 75% from the compound of Formula IV, IVa or IVb. In some embodiments, the yield of Formula I, Ia or Ib can be at least 25% from the compound of Formula IV, IVa or IVb. In some embodiments, the yield of Formula I, Ia or Ib can be at least 50% from the compound of Formula IV, IVa or IVb. In some embodiments, the yield of Formula I, Ia or Ib can be at least 65% from the compound of Formula IV, IVa or IVb.

In some embodiments, the method of preparing the compound of Formula Ia having the structure:

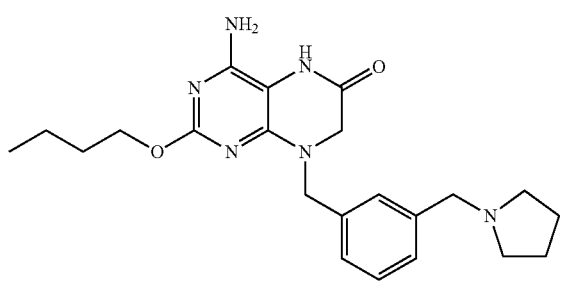 [SMILES: CCCCOc1nc(N)c2c(n1)N(Cc1cccc(CN3CCCC3)c1)CC(=O)N2]

includes the step of forming the first reaction mixture of the compound of Formula IIa having the structure:

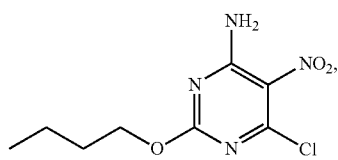 [SMILES: CCCCOc1nc(N)c([N+](=O)[O-])c(Cl)n1]

triethylamine, ethyl acetate, and the bisoxalate salt of the compound of Formula IIIa having the structure:

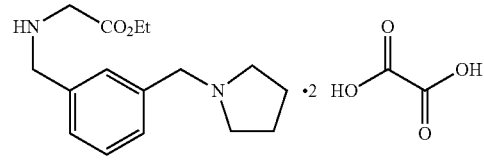 [SMILES: CCOC(=O)CNCc1cccc(CN2CCCC2)c1 ; O=C(O)C(=O)O]

under conditions suitable to form the compound of Formula IVa having the structure:

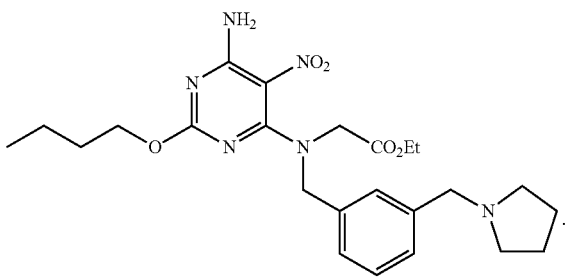 [SMILES: CCCCOc1nc(N)c([N+](=O)[O-])c(N(CC(=O)OCC)Cc2cccc(CN3CCCC3)c2)n1]

The method also includes the step of forming a reaction mixture of the compound of Formula IVa and hydrochloric acid to form a monohydrochloride form of the compound of Formula IVa. The method also includes the step of forming the second reaction mixture of the monohydrochloride salt of the compound of Formula IVa, zinc, and acetic acid, under conditions suitable to prepare the compound of Formula Ia.

In some embodiments, the method of preparing the compound of Formula Ia having the structure:

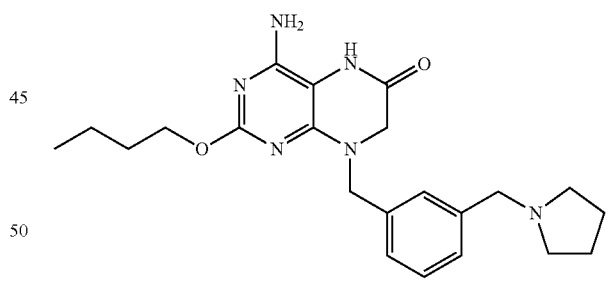

includes the step of forming the first reaction mixture of the compound of Formula IIa having the structure:

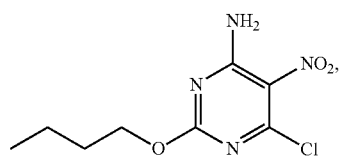 [SMILES: CCCCOc1nc(N)c([N+](=O)[O-])c(Cl)n1]

triethylamine, isopropyl acetate, and the bisoxalate salt of the compound of Formula IIIa having the structure:

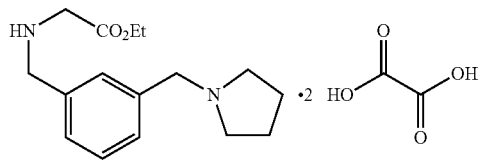

under conditions suitable to form the compound of Formula IVa having the structure:

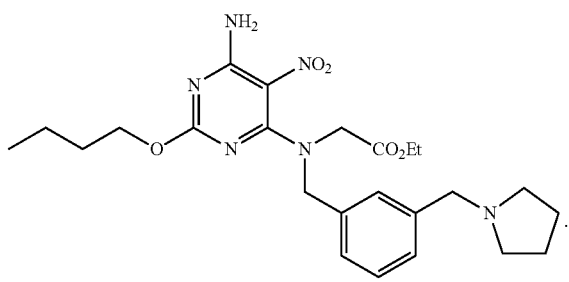 [SMILES: CCCCOc1nc(N)c([N+](=O)[O-])c(N(CC(=O)OCC)Cc2cccc(CN3CCCC3)c2)n1]

The method also includes the step of forming a reaction mixture of the compound of Formula IVa and hydrochloric acid to form a monohydrochloride form of the compound of Formula IVa. The method also includes the step of forming the second reaction mixture of the monohydrochloride salt of the compound of Formula IVa, zinc, and acetic acid, under conditions suitable to prepare the compound of Formula Ia.

In some embodiments, the method of preparing the compound of Formula Ia having the structure:

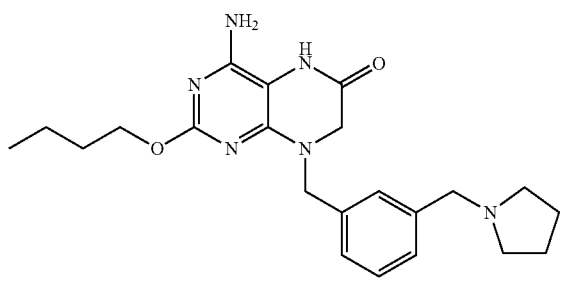 [SMILES: CCCCOc1nc(N)c2c(n1)N(Cc1cccc(CN3CCCC3)c1)CC(=O)N2]

includes the step of forming the first reaction mixture of the compound of Formula IIa having the structure:

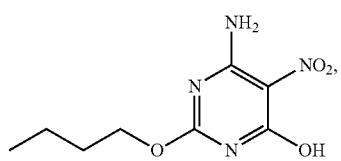

2,4,6-collidine, acetonitrile, and tosyl-Cl, under conditions suitable to form the compound of Formula IIa having the structure:

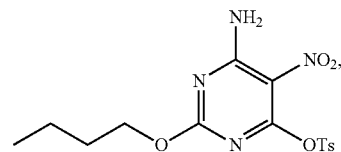 [SMILES: CCCCOc1nc(N)c([N+](=O)[O-])c(OS(=O)(=O)c2ccc(C)cc2)n1]

and adding to the reaction mixture the bisoxalate salt of the compound of Formula IIIa having the structure:

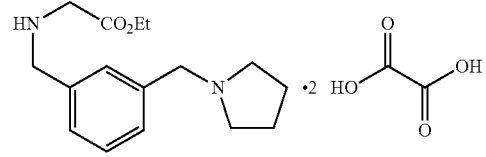 [SMILES: CCOC(=O)CNCc1cccc(CN2CCCC2)c1 ; O=C(O)C(=O)O]

under conditions suitable to form the compound of Formula IVa having the structure:

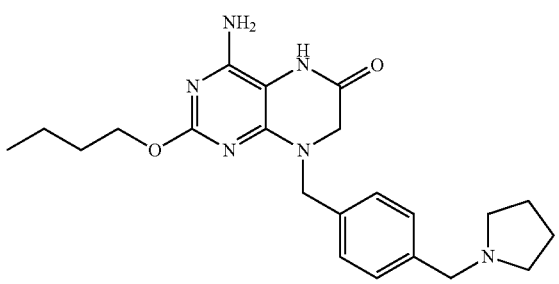 [SMILES: CCCCOc1nc(N)c2c(n1)N(Cc1ccc(CN3CCCC3)cc1)CC(=O)N2]

where the compound of Formula IVa is formed. The method also includes the step of forming the second reaction mixture of the compound of Formula IVa, Raney nickel, hydrogen and methanol, under conditions suitable to prepare the compound of Formula Ia.

In some embodiments, the method of preparing the compound of Formula Ia having the structure:

includes forming the first reaction mixture having the compound of Formula IIa having the structure:

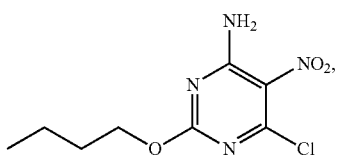 [SMILES: CCCCOc1nc(N)c([N+](=O)[O-])c(Cl)n1]

triethylamine, tetrahydrofuran, and the compound of Formula IIIa having the structure:

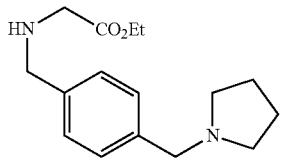 [SMILES: CCOC(=O)CNCc1ccc(CN2CCCC2)cc1]

under conditions suitable to form the compound of Formula IVa having the structure:

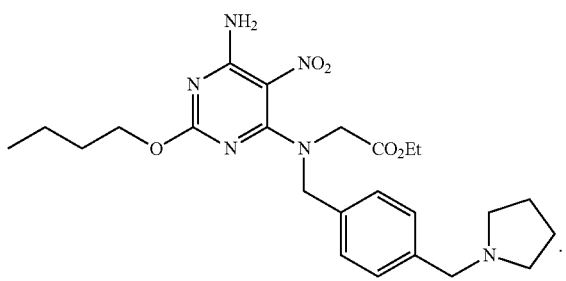 [SMILES: CCCCOc1nc(N)c([N+](=O)[O-])c(N(CC(=O)OCC)Cc2ccc(CN3CCCC3)cc2)n1]

The method also includes the step of forming the second reaction mixture having the compound of Formula IVa, Raney nickel, hydrogen and ethanol, under conditions suitable to prepare the compound of Formula Ia.

V. Method of Making Compounds of Formula III

The present invention also provides a method of preparing a compound of Formula III by a variety of methods. For example, the compound of Formula III can be prepared by alkylation of a primary amine, reductive amination, and other methods.

A. Alkylation of Formula V

In some embodiments, the present invention provides a method of preparing a compound of Formula III, including forming a first reaction mixture of Br—Z—Y—CO$_2$R$^{11}$, a non-nucleophilic base, and a compound of Formula V:

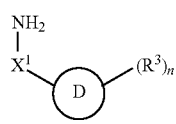

(V)

under conditions suitable to form a compound of Formula III, wherein the compound of Formula III is present at the kilogram scale, thereby preparing the compound of Formula III. Groups Z—Y, R$^3$, R$^{11}$, X$^1$, D and subscript n of Formulas III and V and of Br—Z—Y—CO$_2$R$^{11}$ are as described above.

In some embodiments, the compound of Formula III can be a compound of Formula IIIa or a compound of Formula IIIb. In some embodiments, the compound of Formula III, Formula IIIa or Formula IIIb can have the structure:

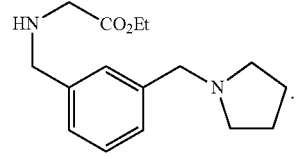 [SMILES: CCOC(=O)CNCc1cccc(CN2CCCC2)c1]

In some embodiments, the compound of Formula V can be Formula Va:

(Va)

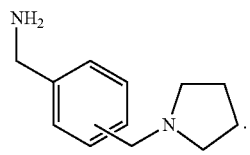

In some embodiments, the compound of Formula V can be Formula Vb:

(Vb)

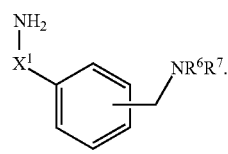

Groups R$^6$, R$^7$ and X$^1$ of Formula Vb are as described above.

In some embodiments, the compound of Formulas V, Va or Vb can have the structure:

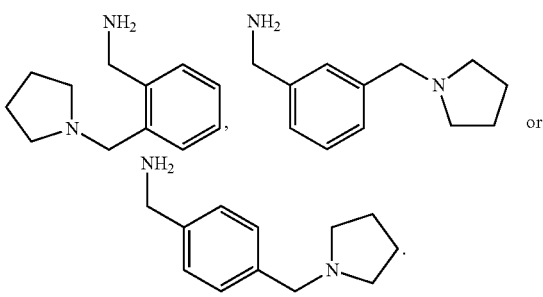

In some embodiments, the compound of Formulas V, Va or Vb can have the structure:

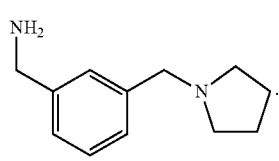

In some embodiments, the compound of Formulas V, Va or Vb can have the structure:

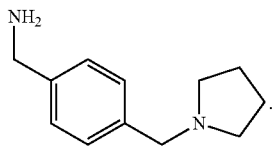 [SMILES: NCc1ccc(CN2CCCC2)cc1]

In some embodiments, the reagent Br—Z—Y—CO$_2$R$^{11}$ can be Br—CH$_2$—CO$_2$R$^{11}$. In some embodiments, the reagent Br—Z—Y—CO$_2$R$^{11}$ can be Br—CH$_2$—CO$_2$Et.

In some embodiments, the present invention provides a method of preparing a compound of Formula IIIa, including the step of forming a first reaction mixture of Br—CH$_2$—CO$_2$R$^{11}$, a non-nucleophilic base, and a compound of Formula Va, under conditions suitable to form the compound of Formula IIIa, wherein the compound of Formula IIIa is present at the kilogram scale. Group R$^{11}$ of Formula IIIa and Br—CH$_2$—CO$_2$R$^{11}$ can be C$_1$-C$_6$ alkyl.

In some embodiments, the present invention provides a method of preparing a compound of Formula IIIb, including the step of forming the first reaction mixture of Br—Z—Y—CO$_2$R$^{11}$, a non-nucleophilic base, and a compound of Formula Vb, under conditions suitable to form the compound of Formula IIIb, wherein Z—Y can be —CR$^4$R$^5$— or —CR$^4$R$^5$—CR$^4$R$^5$—, X$^1$ can be alkylene, each recitation of R$^4$ and R$^5$ can each independently be H or C$_1$-C$_6$ alkyl, or can be taken together with the carbon to which they are attached to form a carbocycle, R$^6$ and R$^7$, taken together with the nitrogen to which they are both attached, can form a substituted or unsubstituted heterocycle, which can contain one or more additional heteroatoms selected from N, O, P, or S, and R$^{11}$ can be alkyl. In some embodiments, groups Z—Y can be —CH$_2$—, —CH(CH$_3$)— or —CH$_2$CH$_2$—, X$^1$ can be C$_1$-C$_6$ alkylene, groups R$^6$ and R$^7$, taken together with the nitrogen to which they are both attached, can form a heterocycle that can be pyrrolidine or piperidine, and R$^{11}$ can be C$_1$-C$_6$ alkyl. In some embodiments, groups Z—Y, R$^4$, R$^5$, R$^6$, R$^7$, R$^{11}$ and X$^1$ can be as described above.

Any suitable non-nucleophilic base can be used in the method of the present invention for preparing the compound of Formula III, IIIa or IIIb. In some embodiments, the non-nucleophilic base can be selected from triethylamine, diisopropylethyl amine, N,N-diethylaniline, pyridine, 2,6-lutidine, 2,4,6-collidine, 4-dimethylaminopyridine, and quinuclidine. In some embodiments, the non-nucleophilic base can be triethylamine.

In some embodiments, the method of making the compound of Formula IIIa includes forming the first reaction mixture of Br—CH$_2$—CO$_2$Et, NEt$_3$, and the compound of Formula Va having the structure:

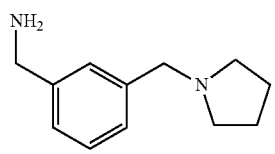 [SMILES: NCc1cccc(CN2CCCC2)c1]

under conditions suitable to form the compound of Formula IIIa having the structure:

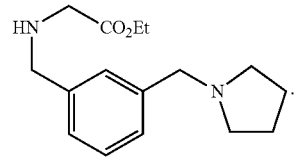 [SMILES: CCOC(=O)CNCc1cccc(CN2CCCC2)c1]

B. Reductive Amination from Formula V

The compound of Formula III can also be prepared under reductive amination conditions. In some embodiments, the present invention provides a method of preparing the compound of Formula III includes forming a first reaction mixture of R$^{14}$—C(O)—CO$_2$R$^{11}$, a reducing agent, and a compound of Formula V, under conditions suitable to form the compound of Formula III wherein groups Z—Y are —CH(R$^{14}$)—, and R$^{14}$ can be H or C$_1$-C$_6$ alkyl. Groups R$^3$, R$^{11}$, X$^1$, D and subscript n of Formulas III, V and R$^{14}$—C(O)—CO$_2$R$^{11}$ are as described above.

In some embodiments, the present invention provides a method of preparing a compound of Formula III, including forming a first reaction mixture of OHC—CO$_2$R$^{11}$, a reducing agent, and a compound of Formula V, under conditions suitable to form the compound of Formula III wherein groups Z—Y are —CH$_2$—. Groups R$^3$, R$^{11}$, X$^1$, D and subscript n of Formulas III, V and OHC—CO$_2$R$^{11}$ are as described above.

In some embodiments, the compound of Formula III can be a compound of Formula IIIa or a compound of Formula IIIb as described above. In some embodiments, the compound of Formula III, Formula IIIa or Formula IIIb can have the structure:

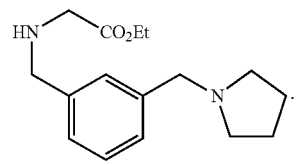 [SMILES: CCOC(=O)CNCc1cccc(CN2CCCC2)c1]

In some embodiments, the compound of Formula III and Formula IIIb can have the structure:

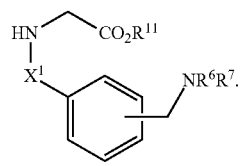

In some embodiments, the compound of Formula V can be a compound of Formula Va or a compound Formula Vb as described above. In some embodiments, the compound of Formulas V, Va or Vb can have the structure:

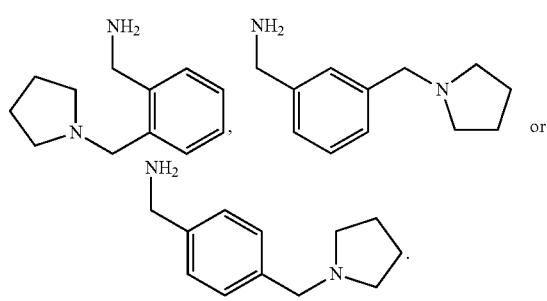

In some embodiments, the compound of Formulas V, Va or Vb can have the structure:

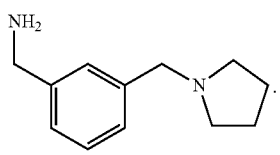

In some embodiments, the compound of Formulas V, Va or Vb can have the structure:

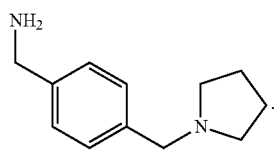

In some embodiments, the reagent OHC—$CO_2R^{11}$ can be OHC—$CO_2Et$.

In some embodiments, the present invention provides a method of preparing a compound of Formula IIIa, including the step of forming a first reaction mixture of OHC—$CO_2R^{11}$, a reducing agent, and a compound of Formula Va, under conditions suitable to form the compound of Formula IIIa, wherein group $R^{11}$ is $C_1$-$C_6$ alkyl. In some embodiments, group $R^{11}$ can be as defined above.

In some embodiments, the present invention provides a method of preparing a compound of Formula IIIb having the structure:

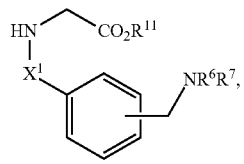

including the step of forming the first reaction mixture of OHC—$CO_2R^{11}$, a reducing agent, and a compound of Formula Vb, under conditions suitable to form a compound of Formula IIIb, wherein $X^1$ can be alkylene, $R^6$ and $R^7$, taken together with the nitrogen to which they are both attached, can form a substituted or unsubstituted heterocycle, which can contain one or more additional heteroatoms selected from N, O, P, or S, and $R^{11}$ can be alkyl. In some embodiments, $X^1$ can be $C_1$-$C_6$ alkylene, groups $R^6$ and $R^7$ can be taken together with the nitrogen to which they are attached to form a heterocycle that can be pyrrolidine or piperidine, and $R^{11}$ can be $C_1$-$C_6$ alkyl. In some embodiments, groups $R^6$, $R^7$, $R^{11}$ and $X^1$ can be as described above.

The reducing agent of the reductive amination methods can include any suitable reducing agents such as sodium triacetoxyborohydride (Na(OAc)$_3$BH), sodium borohydride (NaBH$_4$), sodium cyanoborohydride (NaBH$_3$CN), lithium borohydride, potassium borohydride, sodium bis(2-methoxyethoxy)aluminum hydride, lithium tri-tert-butoxyaluminum hydride, sodium tri-methoxyborohydride, sodium tri-(2-ethylhexanoyloxy)borohydride, zinc/hydrochloric acid, BH$_3$-pyridine, or palladium on carbon with a hydrogen atmosphere. In some embodiments, the reducing agent can be Na(OAc)$_3$BH, NaBH$_3$CN, NaBH$_4$, Zn/HCl, or BH$_3$-pyridine. In some embodiments, the reducing agent can be Na(OAc)$_3$BH.

In some embodiments, the method of preparing the compound of Formula IIIa includes forming the first reaction mixture comprising OHC—$CO_2Et$, Na(OAc)$_3$BH, and the compound of Formula Va having the structure:

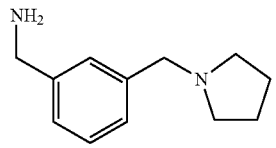 [SMILES: NCc1cccc(CN2CCCC2)c1]

under conditions suitable to form the compound of Formula IIIa having the structure:

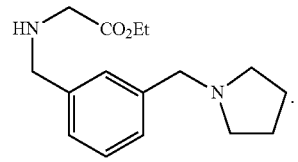

C. Reductive Amination from Formula VI

The compound of Formula III can be prepared under other reductive amination conditions. In some embodiments, the present invention provides a method of preparing a compound of Formula III, including the step of forming a reaction mixture of H$_2$N—Z—Y—$CO_2R^{11}$, a reducing agent, and a compound of Formula VI:

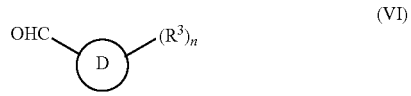

(VI)

under conditions suitable to form a compound of Formula III wherein $X^1$ is —CH$_2$—. Groups Z—Y, $R^3$, $R^{11}$, D and subscript n of Formulas III, VI and H$_2$N—Z—Y—$CO_2R^{11}$ are as described above.

The reductive amination from Formula VI can also proceed via an intermediate compound. In some embodiments, the present invention provides a method of preparing a compound of Formula III, including the step of forming a first reaction mixture of H$_2$N—Z—Y—$CO_2R^{11}$, a non-nucleophilic base, and a compound of Formula VI:

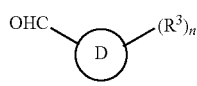
(VI)

under conditions suitable to form an intermediate compound. The method also includes the step of forming a second reaction mixture of the intermediate compound and a reducing agent, under conditions suitable to form a compound of Formula III wherein $X^1$ is —$CH_2$—. Groups Z—Y, $R^3$, $R^{11}$, D and subscript n of Formulas III, VI and $H_2N$—Z—Y—$CO_2R^{11}$ are as described above.

In some embodiments, the compound of Formula III and Formula IIIb can have the structure:

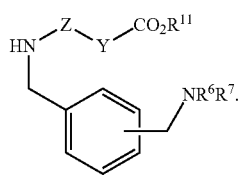

In some embodiments, the compound of Formula VI can be a compound of Formula VIa:

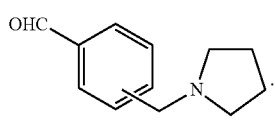
(VIa)

In some embodiments, the compound of Formula VI can be a compound of Formula VIb:

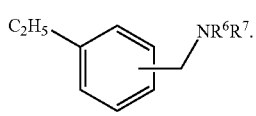
(VIb)

Groups $R^6$ and $R^7$ of Formula VIb are as described above.

In some embodiments, the compound of Formula VI can be a compound of Formula VIc:

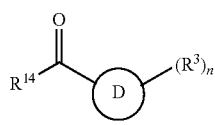
(VIc)

wherein $R^{14}$ can be H or $C_1$-$C_6$ alkyl. In some embodiments, the present invention provides a method of preparing a compound of Formula III, including the step of forming a reaction mixture of $H_2N$—Z—Y—$CO_2R^{11}$, a reducing agent, and a compound of Formula VIc, under conditions suitable to form a compound of Formula III wherein $X^1$ is —$CH(R^{14})$—. Groups Z—Y, $R^3$, $R^{11}$, D and subscript n of Formulas III, VIc and $H_2N$—Z—Y—$CO_2R^{11}$ are as described above.

In some embodiments, the compound of Formulas VI and VIa can have the structure:

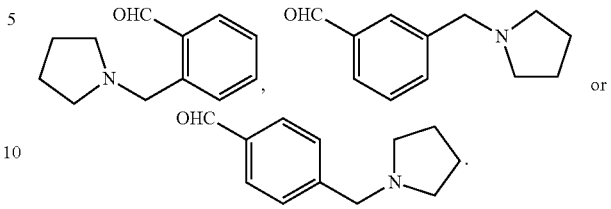

In some embodiments, the compound of Formulas VI and VIa can have the structure:

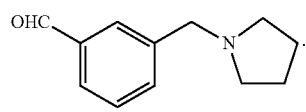 [SMILES: O=Cc1cccc(CN2CCCC2)c1]

In some embodiments, the compound of Formulas VI and VIa can have the structure:

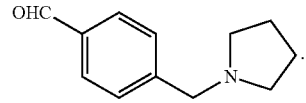 [SMILES: O=Cc1ccc(CN2CCCC2)cc1]

In some embodiments, the reagent $H_2N$—Z—Y—$CO_2R^{11}$ can be $H_2N$—$CH_2$—$CO_2R^{11}$. In some embodiments, the reagent $H_2N$—Z—Y—$CO_2R^{11}$ can be $H_2N$—$CH_2$—$CO_2Et$.

In some embodiments, the present invention provides a method of preparing a compound of Formula IIIa, including the step of forming a reaction mixture of $H_2N$—$CH_2$—$CO_2R^{11}$, a reducing agent, and a compound of Formula VIa, under conditions suitable to form the compound of Formula IIIa, wherein $R^{11}$ is $C_1$-$C_6$ alkyl. In some embodiments, the reaction mixture also includes an acid.

In some embodiments, the present invention provides a method of preparing a compound of Formula IIIb having the structure:

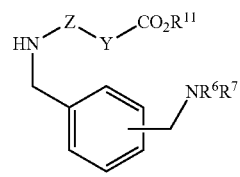

including the step of forming a reaction mixture of $H_2N$—Z—Y—$CO_2R^{11}$, a reducing agent, and a compound of Formula VIb, under conditions suitable to form the compound of Formula IIIb. In some embodiments, the reaction mixture also includes an acid.

In some embodiments, the present invention provides a method of preparing a compound of Formula IIIa, including the step of forming a first reaction mixture of $H_2N$—$CH_2$—$CO_2R^{11}$, a non-nucleophilic base, and a compound of Formula VIa, under conditions suitable to form an intermediate compound. The method also includes the step of forming a second reaction mixture of the intermediate compound and a reducing agent, under conditions suitable to form the compound of Formula IIIa, wherein $R^{11}$ is $C_1$-$C_6$ alkyl.

In some embodiments, the present invention provides a method of preparing a compound of Formula IIIb having the structure:

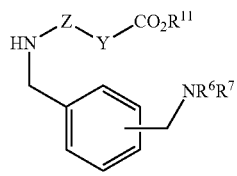

including the step of forming a first reaction mixture of $H_2N$—Z—Y—$CO_2R^{11}$, a non-nucleophilic base, and a compound of Formula VIb, under conditions suitable to form an intermediate compound. The method also includes the step of forming a second reaction mixture of the intermediate compound and a reducing agent, under conditions suitable to form the compound of Formula IIIb, wherein Z—Y can be —$CR^4R^5$— or —$CR^4R^5$—$CR^4R^5$—, each recitation of $R^4$ and $R^5$ can each independently be H or $C_1$-$C_6$ alkyl, or can be taken together with the carbon to which they are attached to form a carbocycle, $R^6$ and $R^7$, taken together with the nitrogen to which they are both attached, form a substituted or unsubstituted heterocycle, which may contain one or more additional heteroatoms selected from N, O, P, or S, and $R^{11}$ can be alkyl. In some embodiments, groups Z—Y can be —$CH_2$—, —$CH(CH_3)$— or —$CH_2CH_2$—, groups $R^6$ and $R^7$ can be taken together with the nitrogen to which they are attached to form a heterocycle that can be pyrrolidine or piperidine, and $R^{11}$ can be $C_1$-$C_6$ alkyl. In some embodiments, groups Z—Y, $R^4$, $R^5$, $R^6$, $R^7$, and $R^{11}$ can be as described above.

Any suitable non-nucleophilic base can be used in the method of preparing the compound of Formula III, IIIa or IIIb from the compound of Formula VI, VIa or VIb, as described above. In some embodiments, the non-nucleophilic base can be triethylamine.

Any suitable reducing agent can be used in the method of preparing the compound of Formula III, IIIa or IIIb from the compound of Formula VI, VIa or VIb, as described above. In some embodiments, the reducing agent can be $Na(OAc)_3BH$.

Any suitable combination of non-nucleophilic base and reducing agent, as described above, can be used in the method of preparing the compound of Formula III, IIIa or IIIb from the compound of Formula VI, VIa or VIb. In some embodiments, the non-nucleophilic base can be selected from triethylamine, diisopropylethyl amine, N,N-diethylaniline, pyridine, 2,6-lutidine, 2,4,6-collidine, 4-dimethylaminopyridine, and quinuclidine; and the reducing agent can be selected from $Na(OAc)_3BH$, $NaBH_3CN$, $NaBH_4$, Zn/HCl, and $BH_3$-pyridine. In some embodiments, the non-nucleophilic base can be triethylamine; and the reducing agent can be $Na(OAc)_3BH$.

Any suitable acid can be used in the method of preparing the compound of Formula III, IIIa or IIIb from the compound of Formula VI, VIa or VIb. For example, the acid can be, but is not limited to, formic acid, acetic acid, and others. In some embodiments, the acid can be acetic acid.

The method of preparing the compound of Formula III, IIIa or IIIb from the compound of Formula VI, VIa or VIb can also include additional reagents. For example, a sulfate salt such as sodium sulfate or magnesium sulfate, can be added to the first reaction mixture. In some embodiments, the first reaction mixture can also include a sulfate salt selected from sodium sulfate and magnesium sulfate.

In some embodiments, the method of preparing the compound of Formula IIIa from the compound of Formula VIa includes the step of forming the first reaction mixture of $H_2N$—$CH_2$—$CO_2Et$, $NEt_3$, $MgSO_4$, and the compound of Formula VIa having the structure:

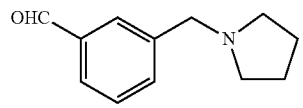 [SMILES: O=Cc1cccc(CN2CCCC2)c1]

under conditions suitable to form the intermediate compound. The method of preparing the compound of Formula IIIa from the compound of Formula VIa can also include forming the second reaction mixture of the intermediate compound, $Na(OAc)_3BH$, and acetic acid, under conditions suitable to form the compound of Formula IIIa having the structure:

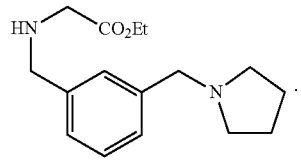 [SMILES: CCOC(=O)CNCc1cccc(CN2CCCC2)c1]

In some embodiments, the method of preparing the compound of Formula IIIa from the compound of Formula VIa includes the step of forming the reaction mixture of $H_2N$—$CH_2$—$CO_2Et$, $Na(OAc)_4BH$, acetic acid and the compound of Formula VIa having the structure:

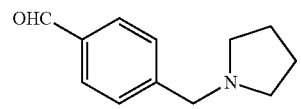 [SMILES: O=Cc1ccc(CN2CCCC2)cc1]

under conditions suitable to form the compound of Formula IIIa having the structure:

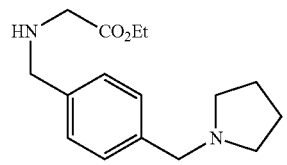

D. Additional Reagents and Reaction Conditions for Methods of Preparing the Compound of Formula III The methods of making the compound of Formula III, IIIa or IIIb can be performed using any suitable solvent, such as isopropanol, ethanol, methanol, dichloromethane, dichloroethane, diethyl ether, tetrahydrofuran, 2-methyltetrahydrofuran, methyl-tert-butylether, acetonitrile, toluene, dimethyl acetamide, or combinations thereof. In some embodiments, the solvent can be tetrahydrofuran, diethyl ether, 2-methyltetrahydrofuran, dichloromethane, or combinations thereof.

In some embodiments, the solvent can be tetrahydrofuran. In some embodiments, the solvent can be isopropanol, ethanol, methanol, dichloromethane, tetrahydrofuran, 2-methyltetrahydrofuran, methyl-tert-butylether, acetonitrile, toluene, dimethyl acetamide, or combinations thereof. In some embodiments, the solvent can be dichloromethane.

The methods of making the compound of Formula III, IIIa or IIIb can be performed under any suitable reaction conditions. For example, the first reaction mixture can be at any suitable temperature, such as, but not limited to, below room temperature, at room temperature, or above room temperature. In some embodiments, the temperature of the first reaction mixture can be from about −20° C. to about 100° C., or from about 0° C. to about 50° C., or from about 10° C. to about 30° C. In some embodiments, the temperature of the first reaction mixture can be at about 20° C. In some embodiments, the temperature of the first reaction mixture can be from about 0° C. to about 100° C., or from about 25° C. to about 100° C., or from about 50° C. to about 75° C. In some embodiments, the temperature of the first reaction mixture can be at about 60° C.

The methods of making the compound of Formula III, IIIa or IIIb can be performed for any suitable reaction time. For example, the reaction time can be for minutes, hours or days. In some embodiments, the reaction time can be several hours, such as overnight. The first reaction mixture can also be at any suitable pressure. For example, the first reaction mixture can be below atmospheric pressure, at about atmospheric pressure, or above atmospheric pressure. In some embodiments, the first reaction mixture can be at about atmospheric pressure.

The methods of the present invention can prepare the compound of Formula III, IIIa or IIIb in any suitable yield. For example, the yield of the compound of Formula III, IIIa or IIIb can be at least about 10% from the compound of Formula V, Va or Vb, or at least about 15%, 20, 25, 30, 35, 40, 45, 50, 55, 60, 65, 70, or at least about 75% from the compound of Formula V, Va or Vb. In some embodiments, the yield of Formula II, IIIa or IIIb can be at least 25% from the compound of Formula V, Va or Vb. In some embodiments, the yield of Formula III, IIIa or IIIb can be at least 50% from the compound of Formula V, Va or Vb. In some embodiments, the yield of Formula III, IIIa or IIIb can be at least 75% from the compound of Formula V, Va or Vb.

The methods of the present invention can prepare the compound of Formula III, IIIa or IIIb in any suitable yield. For example, the yield of the compound of Formula III, IIIa or IIIb can be at least about 10% from the compound of Formula VI, VIa or VIb, or at least about 15%, 20, 25, 30, 35, 40, 45, 50, 55, 60, 65, 70, or at least about 75% from the compound of Formula VI, VIa or VIb. In some embodiments, the yield of Formula III, IIIa or IIIb can be at least 25% from the compound of Formula VI, VIa or Vb. In some embodiments, the yield of Formula III, IIIa or IIIb can be at least 50% from the compound of Formula VI, VIa or VIb. In some embodiments, the yield of Formula III, IIIa or IIIb can be at least 75% from the compound of Formula VI, VIa or VIb.

VI. Oxalate Salt Forms of Formula III and Methods of Preparing

The compound of Formula III, IIIa or IIIb can be in any suitable form. For example, the compound of Formula III, IIIa or IIIb can be in a neutral form or a salt form. Suitable salt forms of the compound of Formula III, IIIa or IIIb include, but are not limited to, inorganic acid addition salts such as chloride, bromide, sulfate, phosphate, and nitrate; organic acid addition salts such as acetate, oxalate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate. The salts can be in some cases hydrates or ethanol solvates.

In some embodiments, the compound of Formula III, IIIa or IIIb can be a salt. In some embodiments, the compound of Formula III, IIIa or IIIb can be the bis-oxalate salt:

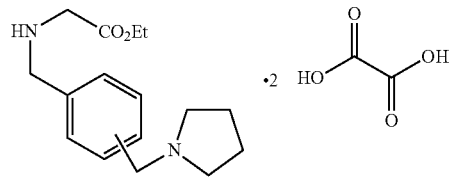

In some embodiments, the compound of Formula III, Formula IIIa or Formula IIIb can be the bis-oxalate salt:

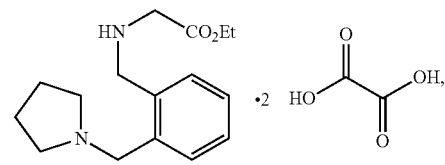

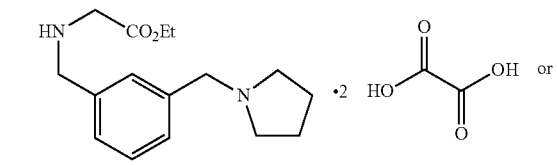

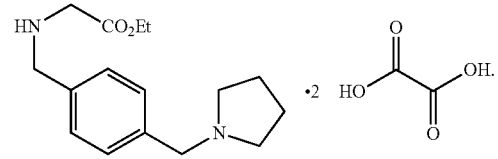

In some embodiments, the compound of Formula III, Formula IIIa or Formula IIIb can be the bis-oxalate salt:

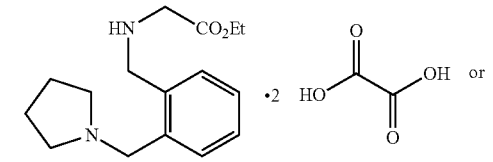

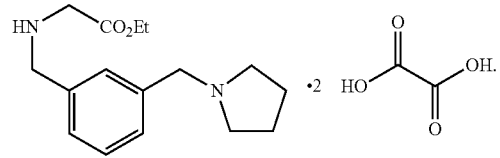

In some embodiments, the present invention provides a compound having the structure:

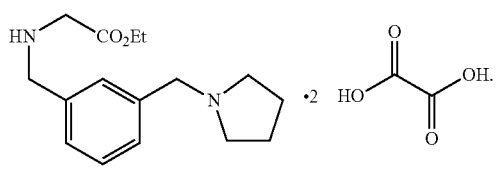

The salt forms of the compound of Formula II, Ia or IIIb can be prepared by any suitable methods. In some embodiments, the present invention provides a method of preparing a compound having the structure:

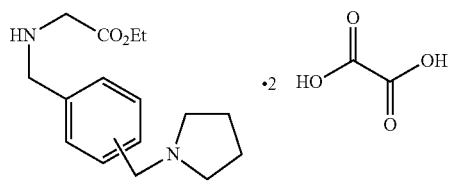

including forming a reaction mixture of oxalic acid and a compound having the structure:

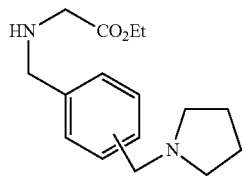

under conditions suitable to prepare the salt.

The salt forms of the compound of Formula III, IIIa or IIIb can be prepared by any suitable methods. In some embodiments, the present invention provides a method of preparing a compound having the structure:

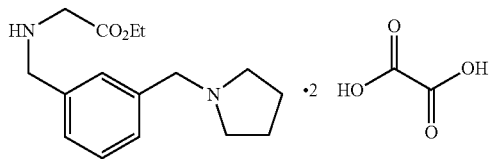 [SMILES: CCOC(=O)CNCc1cccc(CN2CCCC2)c1 ; O=C(O)C(=O)O]

including forming a reaction mixture of oxalic acid and a compound having the structure:

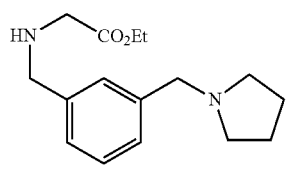 [SMILES: CCOC(=O)CNCc1cccc(CN2CCCC2)c1]

under conditions suitable to prepare the salt.

The bis-oxalate form of the compound of Formula III, IIIa or IIIb can be prepared in any suitable solvent such as methanol, ethanol, isopropanol, ethyl acetate, tetrahydrofuran, water, or combinations thereof. In some embodiments, the solvent can be ethanol and water.

VII. Method of Preparing Compounds of Formula II

The present invention also provides methods of making compounds of Formula II, 4-amino-5-nitro-2,6-substituted pyrimidines. The methods include addition of an amine to the pyrimidine, replacing a chloro group. The chloro-substituted pyrimidine can be prepared from a 4,6-dihydroxypyrimidine by substituting a nitro group at the 5-position, followed by conversion of the dihydroxy groups to chloro groups.

In some embodiments, the present invention provides a method of preparing a compound of Formula II:

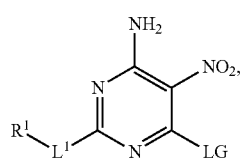

(II)

including forming a first reaction mixture of ammonia, a first non-nucleophilic base, and a compound of Formula IIb:

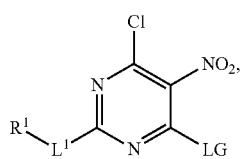

(IIb)

under conditions suitable to form the compound of Formula II. Groups $R^1$, $L^1$ and LG of Formulas II and IIb are as described above.

In some embodiments, the present invention provides a method of preparing a compound of Formula IIa, including forming a first reaction mixture of ammonia, a first non-nucleophilic base, and a compound of Formula IIb having the structure:

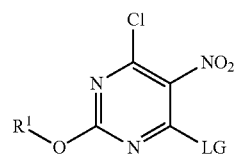

under conditions suitable to form the compound of Formula IIa, wherein $R^1$ can be $C_1$-$C_6$ alkyl, and LG is a leaving group can be halogen, —OH, or —OSO$_2$R$^{13}$, wherein $R^{13}$ can be $C_1$-$C_6$ alkyl, $C_1$-$C_6$ haloalkyl or aryl, wherein the aryl group can be substituted with 1 to 3 $R^{13a}$ groups which can each independently be $C_1$-$C_6$ alkyl, halogen, or NO$_2$.

The first non-nucleophilic base suitable for the method of preparing the compound of Formula II or IIa includes, but is not limited to, triethylamine, diisopropylethyl amine, N,N-diethylaniline, pyridine, 2,6-lutidine, 2,4,6-collidine, 4-dimethylaminopyridine, and quinuclidine. In some embodiments, the first non-nucleophilic base can be triethylamine.

The method of preparing the compound of Formula II or IIa can include additional steps to prepare the compound of Formula IIb. In some embodiments, the method of preparing the compound of Formula II or IIa can include, prior to the step of forming the first reaction mixture, the step of forming a reaction mixture of a nitration agent, and a compound of Formula IIc:

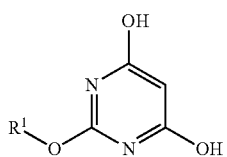
(IIc)

under conditions suitable to form the compound of Formula IId:

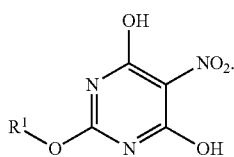
(IId)

The method can also include forming a reaction mixture of a chlorination agent, a second non-nucleophilic base and the compound of Formula IId, under conditions suitable to form the compound of Formula IIb having the structure:

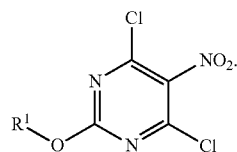

The nitration agent can include any agent suitable for nitrating the 5-position of a pyrimidine ring. Representative nitration agents include, but are not limited to, nitric acid. In some embodiments, the nitration agent can be nitric acid.

The chlorination agent can include any agent suitable to replace the hydroxy groups of Formula IIc with a chloro group. Representative chlorination agents include, but are not limited to, phosphorous oxychloride, thionyl chloride, oxalyl chloride and sulfuryl chloride. In some embodiments, the chlorination agent can be phosphorous oxychloride.

The second non-nucleophilic base can be the same or different from the non-nucleophilic base used to prepare the compound of Formula II or IIa. In some embodiments, the second non-nucleophilic base can be N,N-diethylaniline.

Any combination of the nitration agent, first non-nucleophilic base, chlorination agent and second non-nucleophilic base can be used in the method of preparing the compound of Formula II or IIa. In some embodiments, the chlorination agent can be selected from phosphorous oxychloride, thionyl chloride, oxalyl chloride and sulfuryl chloride; and the second non-nucleophilic base can be selected from triethylamine, diisopropylethyl amine, N,N-dimethylaniline, N,N-diethylaniline, pyridine, 2,6-lutidine, 2,4,6-collidine, 4-dimethylaminopyridine, and quinuclidine. In some embodiments, the first non-nucleophilic base can be triethylamine; the nitration agent can be nitric acid; the chlorination agent can be phosphorous oxychloride; and the second non-nucleophilic base can be N,N-diethylaniline.

In some embodiments, the method of preparing the compound of Formula IIa can include forming the reaction mixture of nitric acid, acetic acid, and a compound of Formula IIc:

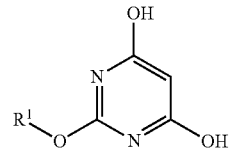
(IIc)

under conditions suitable to form the compound of Formula IId:

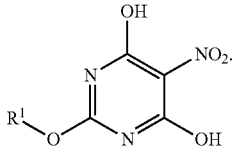
(IId)

The method can also include forming the reaction mixture of phosphorous oxychloride, N,N-dimethylaniline, and the compound of Formula IId, under conditions suitable to form the compound of Formula IIb having the structure:

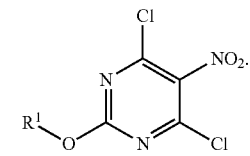

The method can also include forming the first reaction mixture comprising ammonia, triethylamine, and the compound of Formula IIb, under conditions suitable to form the compound of Formula IIa.

The method of making the compound of Formula II can be performed using any suitable solvent, such as isopropanol, ethanol, methanol, dichloromethane, dichloroethane, diethyl ether, tetrahydrofuran, 2-methyltetrahydrofuran, methyl-tert-butylether, ethyl acetate, isopropyl acetate, acetonitrile, toluene, dimethyl acetamide, water, acetic acid, or combinations thereof. In some embodiments, the solvent can be acetic acid. In some embodiments, the solvent can be methanol and tetrahydrofuran.

The method of making the compound of Formula II or IIa can be performed under any suitable reaction conditions. For example, the first reaction mixture can be at any suitable temperature, such as, but not limited to, below room temperature, at room temperature, or above room temperature. In some embodiments, the temperature of the first reaction mixture can be from about −50° C. to about 100° C., or from about −50° C. to about 50° C., or from about −50° C. to about 0° C., or from about 0° C. to about 50° C., or from about 10° C. to about 30° C. In some embodiments, the temperature of the first reaction mixture can be at about −20° C. In some embodiments, the temperature of the first reaction mixture can be at about 20° C.

The method of making the compound of Formula II or IIa can be performed for any suitable reaction time. For example, the reaction time can be for minutes, hours or days.

In some embodiments, the reaction time can be several hours, such as overnight. The first reaction mixture can also be at any suitable pressure. For example, the first reaction mixture can be below atmospheric pressure, at about atmospheric pressure, or above atmospheric pressure. In some embodiments, the first reaction mixture can be at about atmospheric pressure.

VIII. Compounds of Formula IIe

The present invention provides compounds of Formula IIe:

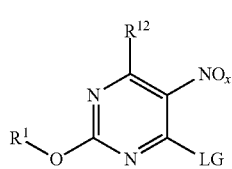

wherein $R^1$ of Formula IIe can be alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclyl heteroalkyl, substituted heterocyclylheteroalkyl, arylheteroalkyl, substituted arylheteroalkyl, heteroarylheteroalkyl, or substituted heteroarylheteroalkyl. LG of Formula IIe can be a leaving group which can be halogen, —OH, or —OSO$_2$R$^{13}$, wherein R$^{13}$ can be C$_1$-C$_6$ alkyl, C$_1$-C$_6$ haloalkyl or aryl, wherein the aryl group can be substituted with 1 to 3 R$^{13a}$ groups which can each independently be C$_1$-C$_6$ alkyl, halogen, or NO$_2$. Group R$^{12}$ of Formula IIe can be selected from halogen, —OR$^{12a}$ and —N(R$^{12a}$)$_2$, wherein each R$^{12a}$ can independently be H or C$_1$-C$_6$ alkyl. Subscript x of Formula IIe can be 1 or 2. And when R$^{12}$ is —NH$_2$ and subscript x is 2, then LG is a halogen.

In some embodiments, the present invention provides a compound of Formula IIe, wherein $R^1$ of Formula IIe can be C$_1$-C$_6$ alkyl, LG is a leaving group selected from halogen, —OH and —O-tosylate, R$^{12}$ can be halogen, —OH or —NH$_2$, and subscript x can be 1 or 2, such that when R$^{12}$ is —NH$_2$ and subscript x is 2, then LG can be a halogen.

In some embodiments, $R^1$ of Formula IIe can be alkyl. In some embodiments, $R^1$ of Formula IIe can be C$_1$-C$_6$ alkyl. In some embodiments, $R^1$ of Formula IIe can be methyl, ethyl, n-propyl, isopropyl, n-butyl, iso-butyl, sec-butyl, tert-butyl, n-pentyl, iso-pentyl or n-hexyl. In some embodiments, $R^1$ of Formula IIe can be methyl, ethyl, n-propyl, or n-butyl. In some embodiments, $R^1$ of Formula IIe can be n-butyl.

In some embodiments, R$^{13}$ can be methyl, trifluoromethyl or phenyl, wherein the phenyl can be substituted with 1 R$^{13a}$ group that can be methyl, fluoro, chloro, bromo or NO$_2$.

In some embodiments, R$^{12}$ of Formula IIe can be chloro, —OH or —NH$_2$. In some embodiments, R$^{12}$ of Formula IIe can be —NH$_2$.

In some embodiments, the leaving group LG of Formula IIe can be chloro or —OH. In some embodiments, the leaving group LG of Formula IIe can be chloro.

In some embodiments, subscript x can be 1 or 2. In some embodiments, subscript x can be 1. In some embodiments, subscript x can be 2.

In some embodiments, $R^1$ can be n-butyl, R$^{12}$ can be chloro, —OH or —NH$_2$, and LG can be chloro or —OH. In some embodiments, the compound of Formula IIe can be selected from:

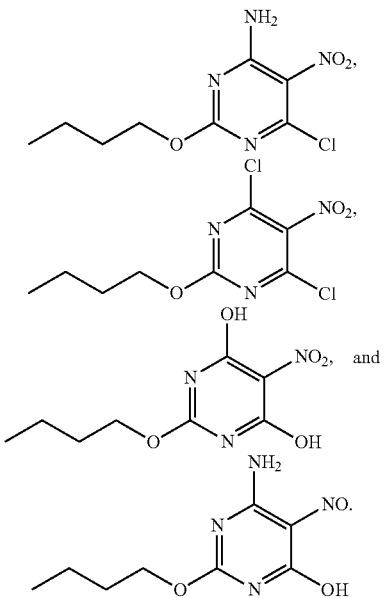

In some embodiments, the compound of Formula IIe has the structure:

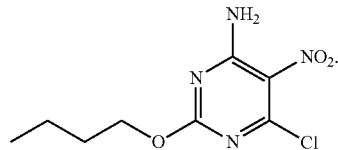

The compounds of Formula IIe include the isomers, salts, hydrates, and prodrug forms thereof.

IX. EXAMPLES

Example 1

Preparation of 2-n-butoxy-6-chloro-5-nitropyrimidin-4-amine

Preparation of 2-n-butoxy-6-chloro-5-nitropyrimidin-4-amine is described.

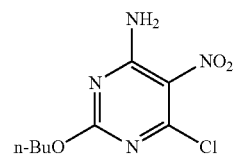

Preparation of n-butyl carbamidate hydrochloride

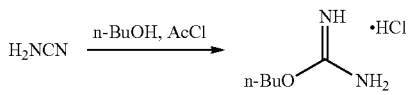

A flask was charged with n-butanol (250 mL) and acetyl chloride (20.6 g, 262 mmol, 1.1 equiv.) was slowly charged at a rate to keep the internal temperature of the solution to below about 30° C. After the addition was completed, the solution was stirred for approximately 15 minutes. To the solution was slowly charged cyanamide (10 g, 238 mmol, 1.0 equiv.) as a solution in n-butanol (250 mL) at a rate to keep the internal temperature of the slurry below about 40° C. Once addition is complete, the content temperature was adjusted to about 40° C. and maintained until reaction is complete (typical reaction time ~16 . . . 24 hours). The mixture was concentrated under reduced pressure to provide n-butyl carbamidate hydrochloride.

Preparation of 2-n-butoxypyrimidine-4,6-diol

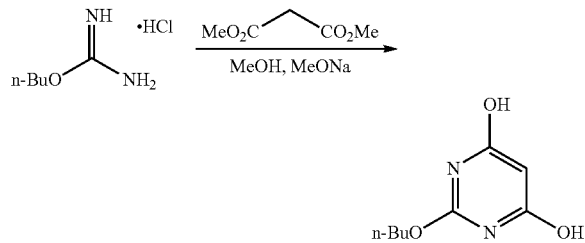

n-Butyl carbamidate hydrochloride (1.36 kg) was dissolved in methanol (7 L) and cooled to about −5° C. Sodium methoxide in methanol (1.44 kg of 98% NaOMe in 4.9 L MeOH) was slowly charged to the solution at a rate to keep the internal temperature below about 0° C. Once the sodium methoxide addition was complete, methyl malonate (1.18 kg) was added. The resulting reaction mixture was stirred at about 20° C. until the reaction was complete. Upon completion, the solution was concentrated and the pH was adjusted to pH 4 to 5. The resulting precipitate was filtered to provide 2-n-butoxypyrimidine-4,6-diol.

Preparation of 2-n-butoxy-5-nitropyrimidine-4,6-diol

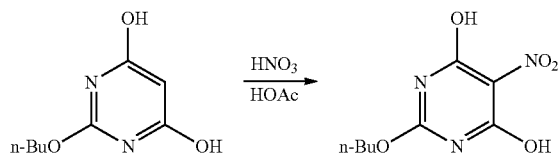

2-n-Butoxypyrimidine-4,6-diol (850 g) was added to a premixed solution of fuming $HNO_3$ (2.1 kg) and acetic acid (4 L) at about 0 to 10° C. The solution was stirred at ambient temperature overnight. The resulting mixture was added to water (4 L) which was extracted with dichloromethane (4 L). The organic phase was concentrated and co-evaporated with toluene to give of 2-n-butoxy-5-nitropyrimidine-4,6-diol. $^1$H NMR (400 MHz, DMSO-$d_6$) δ 4.08 (t, J=6.7 Hz, 2H), 1.58 (tt, J=7.1, 7.3 Hz, 2H), 1.35 (tq, J=7.5, 7.5 Hz), 0.90 (t, J=7.4 Hz, 3H).

Preparation of 2-n-butoxy-4,6-dichloro-5-nitropyrimidine

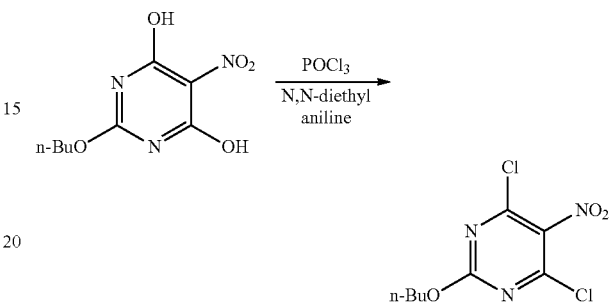

A reactor was charged with 2-n-butoxy-5-nitropyrimidine-4,6-diol (700 g) followed by $POCl_3$ (2.5 L). The mixture was heated to about 40° C. and N,N-diethylaniline (1.2 L) was slowly added. Once the addition was completed, the internal temperature was adjusted to about 60° C. for additional 3 hours. Once the reaction was deemed complete, the temperature was adjusted to about 20° C. The resulting solution was slowly added to water (10 L). The mixture was extracted with dichloromethane (5 L) and concentrated under reduced pressure. The resulting oil was passed through a pad of silica gel eluting with ethyl acetate and heptanes to provide 2-n-butoxy-4,6-dichloro-5-nitropyrimidine. A purified sample of 2-n-butoxy-4,6-dichloro-5-nitropyrimidine has the following spectrum: $^1$H NMR (400 MHz, $CDCl_3$) δ 4.46 (t, J=6.6 Hz, 2H), 1.81 (tt, J=7.1, 7.3 Hz, 2H). 1.49 (tq, J=7.5, 7.5 Hz, 2H), 0.98 (t, J=7.4 Hz, 3H).

Preparation of 2-n-butoxy-6-chloro-5-nitropyrimidin-4-amine

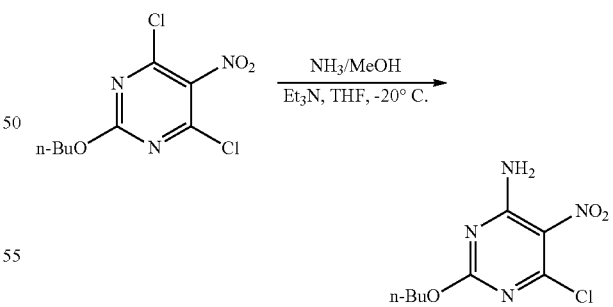

7M $NH_3$ in MeOH (180 mL) was added dropwise into a solution of 2-n-butoxy-4,6-dichloro-5-nitropyrimidine (339 g, 1.2 moles) with $Et_3N$ (240 mL) in THF (1.5 L) at about −20° C. The mixture was stirred at this temperature for about 2 hours and then an additional 20 mL of 7 M $NH_3$ in MeOH was added and stirred for about one hour. To this solution was added 500 mL water and 500 ml MTBE. Layer separation and extract of the water layer with 500 mL MTBE followed by washing with 1 N HCl and 50% $NaH_2PO_3$ gave a MTBE solution. The solution was concentrated was and then crystallized from 1.5 liter of EtOAc:petroleum ether (1:4), to give 2-n-butoxy-6-chloro-5-nitropyrimidin-4-amine. A purified sample of 2-n-butoxy-6-chloro-5-nitropyrimidin-4-amine has the following spectrum: $^1$H NMR (400 MHz, CDCl$_3$) δ 4.35 (t, J=6.6 Hz, 2H), 1.75 (tt, J=7.0, 7.2 Hz, 2H), 1.46 (tq, J=7.5, 7.5 Hz, 2H), 0.96 (t, J=7.4 Hz, 3H).

Example 2

Preparation of ethyl
N-(3-pyrrolidin-1-ylmethyl)benzyl glycinate
bis-oxalate salt Preparation of ethyl N-(3-pyrrolidin-1-ylmethyl)benzyl glycinate bis-oxalate salt is described.

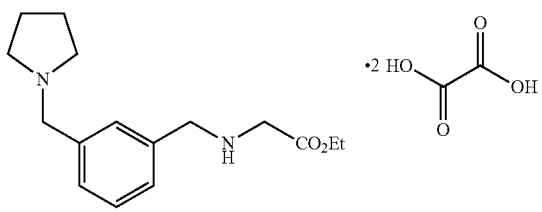 [SMILES: CCOC(=O)CNCc1cccc(CN2CCCC2)c1 ; O=C(O)C(=O)O]

Preparation of 3-(pyrrolidin-1-ylmethyl)benzonitrile

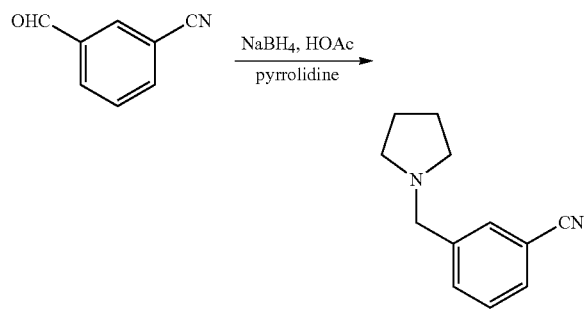

Sodium borohydride (6.2 kg) and dichloromethane (285 kg) were combined. The content temperature was adjusted to about 0° C. and acetic acid (29 kg) was slowly charged over about 2 hours. The mixture was agitated at about 0° C. for 2 hours and then warmed to about 20° C.

In a second reaction vessel was combined 3-cyanobenzaldehyde (14 kg), dichloromethane (52 kg) and pyrrolidine (7.8 kg) and the resulting mixture was agitated at about 20° C. To this mixture was slowly charged with the sodium borohydride/dichloromethane mixture over about 2 hours at about 20° C. After the addition was complete, the mixture was agitated for about 12 hours at about 20° C. Once the reaction was deemed complete, an aqueous sodium hydroxide solution (105 kg, 10% w/w) was added. The phases were separated and the aqueous phase was extracted with dichloromethane (53 kg) three times. Water (71 kg) was added to the combined organic phases and the pH was adjusted to ~2 by adding an aqueous HCl solution (71 kg, 2M). The phases were separated and the organic phase was extracted with an aqueous HCl solution (44 kg, 1M). The pH of the combined aqueous phases was adjusted to 12 by adding an aqueous sodium hydroxide solution (62 kg, 10% w/w). The aqueous phase was extracted with dichloromethane (62 kg) three times. The organic phase was washed with water (14 kg) two times, dried over sodium sulfate, and concentrated. Tetrahydrofuran (20 kg) was charged and concentrated to provide 3-(pyrrolidin-1-ylmethyl)benzonitrile. A purified sample of 3-(pyrrolidin-1-ylmethyl)benzonitrile has the following spectrum: $^1$H NMR (400 MHz, CDCl$_3$) δ 7.64-7.40 (m, 4H), 3.63 (s, 2H), 2.50 (s, 4H), 1.80 (s, 4H).

Preparation of
(3-(pyrrolidin-1-ylmethyl)phenyl)methanamine

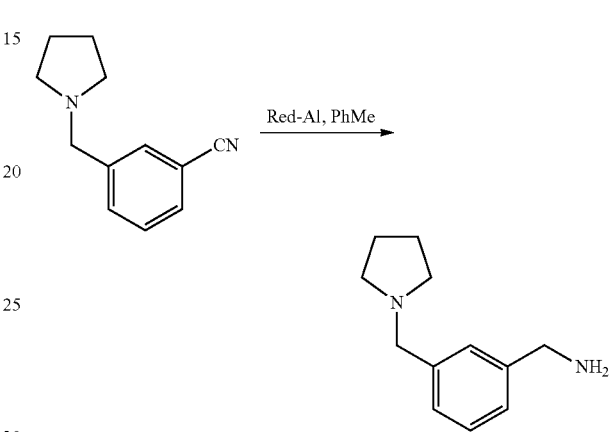

Red-Al (65 wt % in toluene, 6.8 kg, 55 equiv.) in toluene (3 L) solution was cooled to about 0° C. To this solution was added with a solution of 3-(pyrrolidin-1-ylmethyl)benzonitrile (810 g) in toluene (8 L) while maintaining an internal temperature of below about 5° C. Once the addition was complete, the solution was agitated at about 0° C. for about one hour and then warmed to about 20° C. and agitated for about 16 hours.

At the end of the agitation period, the reaction contents were added to a cooled (about 0° C.) aqueous potassium hydroxide solution (25 volumes, 20 L) at a rate to maintaining the internal temperature of less than about 5° C. Once the addition was complete, the contents were warmed to about 20° C. The phases were separated and the aqueous phase was extracted with toluene (8 L). The combined organics were concentrated under reduced pressure to provide to provide (3-(pyrrolidin-1-ylmethyl)phenyl)methanamine. A purified sample of (3-(pyrrolidin-1-ylmethyl)phenyl)methanamine has the following spectrum: $^1$H NMR (400 MHz, CDCl$_3$) δ 7.19-7.28 (m, 4H), 3.85 (s, 2H), 3.61 (s, 2H), 2.51 (s, 4H), 1.78 (s, 4H), 1.65 (br s, 2H).

Preparation of ethyl
N-[3-pyrrolidin-1-ylmethyl)benzyl]glycinate

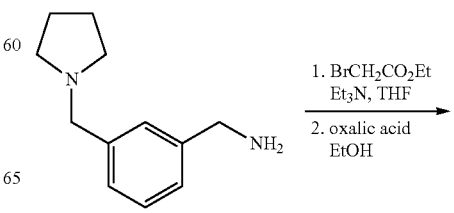

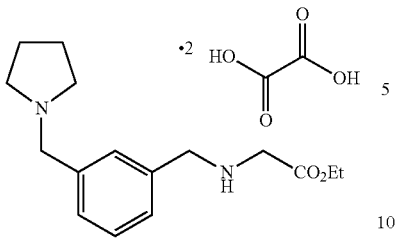

Tetrahydrofuran (130 kg) at about 20° C. was combined with (3-(pyrrolidin-1-ylmethyl)phenyl)methanamine (15.1 kg) and triethylamine (10.5 kg). Ethyl bromoacetate (13.9 kg) was then charged to the reaction contents over about 2 hours and the resulting mixture was agitated at about 20° C. until the reaction was deemed complete. Water (520 kg) was charged to the reaction mixture followed by ethyl acetate (135 kg). The phases were separated and the aqueous phase was extracted twice with ethyl acetate (135 kg). The combined organic phases were washed with water (75 kg). The organic phase was concentrated under reduced pressure. The resulting oil was reconstituted in methy-tert-butylether and treated with silica gel (4 kg). The slurry was filtered and washed methy-tert-butylether (30 kg).

The filtrate was concentrated and the resulting foam was reconstituted in ethanol (312 L) and water (16 L). The mixture was heated to about 70° C. A solution of oxalic acid (11.4 kg) dissolved in ethanol (40 kg) was slowly added. The resultant slurry was heated to about 60° C. and agitated for about 2 hours. The slurry was slowly cooled to about −5° C. over about 4 hours. The slurry was filtered and the solids were washed with ethanol (50 kg). The solids were dried in a vacuum oven to provide ethyl N-(3-pyrrolidin-1-ylmethyl) benzyl glycinate bis-oxalate. A purified sample of ethyl N-(3-pyrrolidin-1-ylmethyl)benzyl glycinate bis-oxalate has the following spectrum: $^1$H NMR (400 MHz, CDCl$_3$) δ 7.43-7.56 (m, 4H), 4.27 (s, 2H), 4.23 (s, 2H), 4.13 (q, J=7.2 Hz, 2H), 3.88 (s, 2H), 3.35-3.45 (m, 2H), 2.98-3.16 (m, 2H), 1.98-2.06 (m, 2H), 1.79-1.95 (m, 2H), 1.13 (t, J=7.2 Hz, 3H).

Example 3

Preparation of ethyl
N-(3-pyrrolidin-1-ylmethyl)benzyl glycinate
bis-oxalate

Preparation of ethyl N-(3-pyrrolidin-1-ylmethyl)benzyl glycinate bis-oxalate is described.

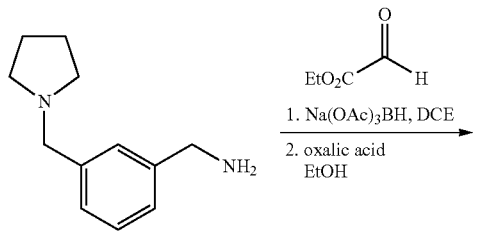

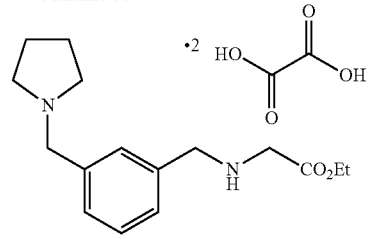

(3-(Pyrrolidin-1-ylmethyl)phenyl)methanamine (500 mg, 2.6 mmol) was dissolved in dichloroethane (7.5 mL). Ethyl glyoxalate (540 mg, 2.9 moles, ~50 weight % solution in toluene) was added followed by the addition of sodium acetoxy borohydride (840 mg, 3.9 mmol). Once deemed complete, the reaction was quenched with a saturated sodium bicarbonate solution (5 mL). The phases were separated and the organic phase was concentrated. The oxalate salt was prepared in a similar manner as previously described. A purified sample of ethyl N-(3-pyrrolidin-1-ylmethyl)benzyl glycinate bis-oxalate has the same $^1$H NMR as previously described.

Example 4

Preparation of ethyl
N-(3-pyrrolidin-1-ylmethyl)benzyl glycinate
bis-oxalate

Preparation of ethyl N-(3-pyrrolidin-1-ylmethyl)benzyl glycinate bis-oxalate is described.

Preparation of 1-(3-bromobenzyl)pyrrolidine

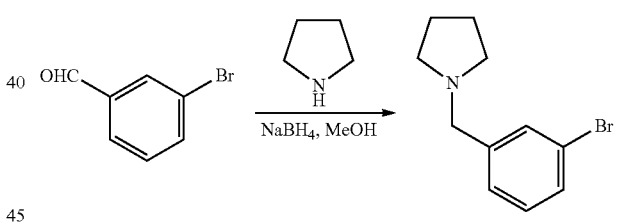

A solution of 3-bromobenzaldehyde (350 g, 1.83 mol) in ethanol (1.9 L) was cooled to about 15° C. and pyrrolidine (135 g, 1.90 mol) was added while maintaining the reaction content temperature below about 25° C. After the addition was complete, the reaction mixture was stirred at room temperature for about 2 hours. The reaction mixture was then concentrated and diluted with ethanol (1.4 L).

To a separate round bottom flask was charged ethanol (960 mL). Sodium borohydride (96 g, 2.5 mol) was charged portionwise over about 30 minutes maintaining the temperature to about 15° C. The ethanolic solution initially prepared was added to the second ethanolic solution via an addition funnel over 30 minutes keeping the temperature below about 35° C. Once the addition was complete, the mixture was stirred at room temperature until the reaction was deemed complete. The reaction mixture was cooled to about 0° C. and quenched by adding water (800 mL) over 30 minutes keeping the temperature below about 25° C. Aqueous HCl (1.5 L) was added over 30 minutes keeping the temperature below about 35° C. The mixture was vigorously stirred at room temperature for about 10 minutes after the addition.

The mixture was extracted with methyl-tert-butylether (2 L) and the acidic aqueous layer was then basified by adding aqueous NaOH (780 mL). The resulting aqueous layer was extracted with methyl-tert-butylether (4 L×2). The combined organic layers were concentrated and co-evaporated with toluene. The solution was treated with potassium carbonate (80 g, 325 mesh) and the slurry was filtered and the cake was rinsed with toluene (300 mL) and concentrated to provide 1-(3-bromobenzyl)pyrrolidine. A purified sample of (1-(3-bromobenzyl)pyrrolidine) has the following spectrum: $^1$H NMR (300 MHz, CDCl$_3$) δ 7.1-7.5 (m, 4H), 3.6 (s, 2H), 2.4-2.6 (m, 4H), 1.7-1.9 (m, 4H).

Preparation of 3-(pyrrolidin-1-ylmethyl)benzaldehyde

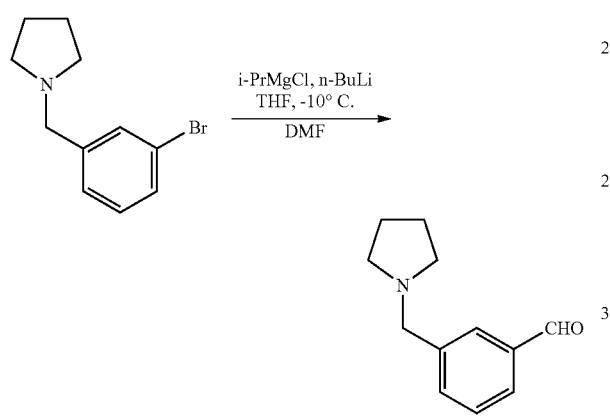

Tetrahydrofuran (1.5 L) was charged to a round bottom flask and cooled to about 5° C. Isopropylmagnesium chloride (1.9M in THF, 215 mL, 406 mmol) was added over about 10 minutes, maintaining the temperature below about 15° C. After the addition was complete, the solution was cooled to about −10° C. and n-butyllithium (1.5M in hexanes, 542 mL, 812 mmol) was added over about 30 minutes. The resulting solution was stirred at about 0° C. for about 45 minutes and then cooled to about −10° C. A solution of 1-(3-bromobenzyl)pyrrolidine (167 g, 88 weight %, 611 mmol) in dry tetrahydrofuran (750 mL) was added over 25 minutes while keeping the temperature at about −10° C. to −15° C. Once the addition was complete, the mixture was stirred at about −10° C. to −15° C. until the reaction was deemed complete.

A solution of N,N-dimethylformamide (145 mL, 1.88 mol) in tetrahydrofuran (150 mL) was added to the reaction mixture at about −10° C. to −15° C. over about 20 minutes. The mixture was stirred at about −5° C. to 0° C. for about one hour. Once the reaction was deemed complete, the mixture was cooled to about −10° C., and the reaction was quenched by adding water (1 L) slowly over 20 minutes with vigorous stirring, keeping the temperature below about 0° C. to 10° C. The mixture was warmed to room temperature and the bottom aqueous layer was discarded. The organic layer was extracted twice with 2M H$_3$PO$_4$ (650 mL×1 and 150 mL×1). These aqueous layers were combined and charged to methyl-tert-butylether (500 mL). The mixture was cooled to about 10° C. with agitation. The aqueous layer was basified by adding 3N NaOH (~550 mL) slowly keeping the temperature below about 25° C. The mixture was filtered and the solids were washed with methyl-tert-butylether (250 mL). The filtrate was transferred to a separatory funnel, and the layers were separated. The organic layer was washed with water (400 mL). The resulting organic layer (~960 mL) was concentrated and co-evaporated with toluene to provide the product, 3-(pyrrolidin-1-ylmethyl)benzaldehyde. A purified sample of 3-(pyrrolidin-1-ylmethyl)benzaldehyde has the following spectrum: $^1$H NMR (300 MHz, CDCl$_3$) δ 10.0 (s, 1H), 7.85 (s, 1H), 7.75 (d, J=7.5 Hz, 1H), 7.63 (d, J=7.5 Hz, 1H), 7.48 (dd, J=7.5, 7.5 Hz, 1H), 3.7 (s, 2H), 2.4-2.6 (m, 4H), 1.7-1.9 (m, 4H).

Preparation of ethyl N-(3-pyrrolidin-1-ylmethyl)benzyl glycinate bis-oxalate

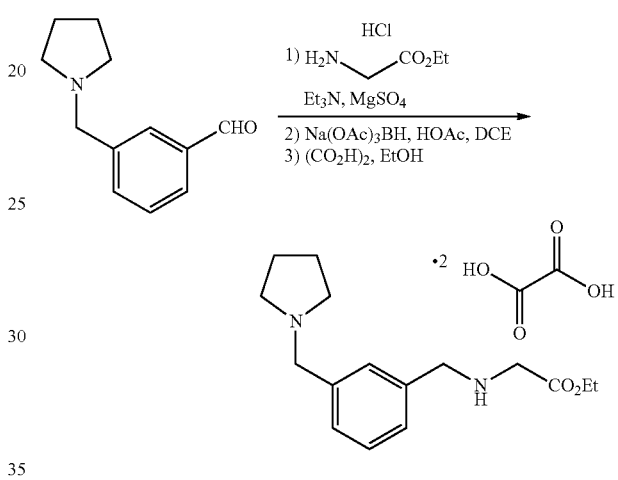

A round bottom flask was charged with dichloroethane (1.2 L), 3-(pyrrolidin-1-ylmethyl)benzaldehyde (118 g, ~70 weight %, 423 mmol) and glycine ethyl ester hydrochloride (118 g, 845 mmol). The mixture was agitated at room temperature for about 10 minutes and then triethylamine (118 mL, 845 mmol) and magnesium sulfate (anhydrous powder, 320 g) were added. The reaction mixture was stirred at about 35° C. for about 2 hours.

The mixture was filtered through a funnel which contained anhydrous magnesium sulfate (100 g). The filter cake was rinsed with dichloroethane (200 mL×2). The combined filtrates were concentrated to approximately 200 mL, diluted with dichloroethane (1 L). The resulting solution was cooled to about 10° C. Sodium(triacetoxy)borohydride (116 g, 550 mmol) was added in five portions over 20 minutes. The temperature was adjusted to about −10° C. and acetic acid (120 mL, 2.1 mol) was added to the reaction mixture over about 20 minutes keeping the temperature below about 0° C. After the addition was complete the reaction mixture was warmed to the room temperature over about 1 hour until the reaction was deemed complete. The mixture was cooled to about −10° C. and quenched by adding water (200 mL) slowly over 15 minutes with vigorous stirring, keeping the temperature below about 10° C. Once the addition was complete, the mixture was warmed to room temperature. Aqueous HCl (300 mL) was added to the mixture until a pH of about 3 is achieved. The layers were separated and the dichloroethane layer was extracted with 0.3N HCl (100 mL). The combined acidic aqueous layers were combined with methyl-tert-butylether (600 mL) and cooled to about 10° C. A 50% w/w NaOH solution (~250 mL) was added over about 20 minutes with vigorous stirring keeping the temperature below about 25° C. until the pH was 9 to 10. The phases were separated and the organic layer was washed with water (250 mL). The combined aqueous layers were extracted with methyl-tert-butylether (250 mL). The combined organic layers were concentrated and the residue was dissolved in ethanol (1.8 L). A solution of oxalic acid (66 g, 730 mmol, 2.1 equiv.) in ethanol (500 mL) was slowly added over about 1 hour with stirring at room temperature. The resultant slurry was heated to about 60° C. and agitated for about 2 hours. The slurry was slowly cooled to about −5° C. over about 4 hours. The slurry was filtered and the solids were washed with ethanol (500 mL). The solids were dried in a vacuum oven to provide the product. A purified sample of ethyl N-(3-pyrrolidin-1-ylmethyl)benzyl glycinate bis-oxalate has the following spectrum: $^1$H NMR (400 MHz, CDCl$_3$) δ 7.43-7.56 (m, 4H), 4.27 (s, 2H), 4.23 (s, 2H), 4.13 (q, J=7.2 Hz, 2H), 3.88 (s, 2H), 3.35-3.45 (m, 2H), 2.98-3.16 (m, 2H), 1.98-2.06 (m, 2H), 1.79-1.95 (m, 2H), 1.13 (t, J=7.2 Hz, 3H).

Example 5

Preparation of ethyl N-(3-pyrrolidin-1-ylmethyl)benzyl glycinate bis-oxalate

Preparation of ethyl N-(3-pyrrolidin-1-ylmethyl)benzyl glycinate bis-oxalate is described.

Preparation of 3-(pyrrolidin-1-ylmethyl)benzaldehyde

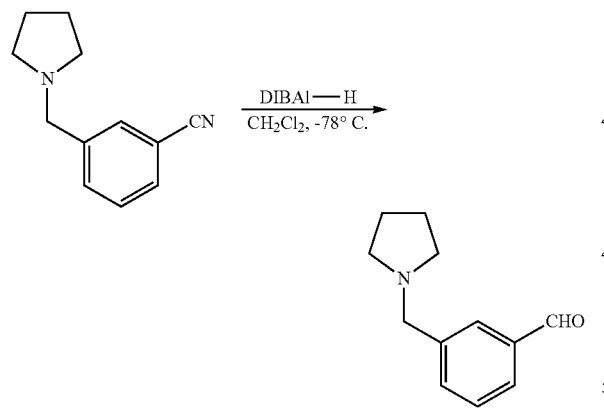

3-(Pyrrolidin-1-ylmethyl)benzonitrile (200 mg, 1.2 mmol) was charged to a flask and dissolved in dichloromethane (1.5 mL). The solution was cooled to about −78° C. and di-isobutylaluminum hydride (1.5 mL, 1M in toluene) was slowly added. The reaction was stirred at about −78° C. for one hour and then warmed to room temperature and stirred overnight. The reaction was quenched with a saturated sodium sulfate solution and extracted into dichloromethane. The organic layer was concentrated and then chromatographed on silica gel eluting with dichloromethane and methanol to provide the desired aldehyde. A purified sample has the following spectrum: $^1$H NMR (300 MHz, CDCl$_3$) δ 10.0 (s, 1H), 7.85 (s, 1H), 7.75 (d, J=7.5 Hz, 1H), 7.63 (d, J=7.5 Hz, 1H), 7.48 (dd, J=7.5, 7.5 Hz, 1H), 3.7 (s, 2H), 2.4-2.6 (m, 4H), 1.7-1.9 (m, 4H).

Preparation of ethyl N-(3-pyrrolidin-1-ylmethyl)benzyl glycinate bis-oxalate

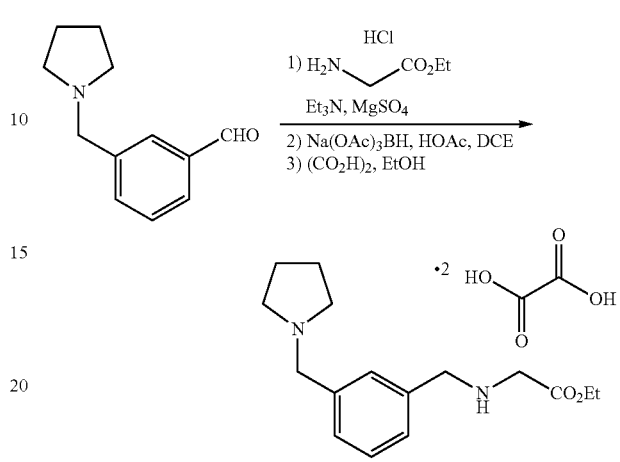

The title compound was prepared as previously described.

Example 6

Preparation of 4-amino-2-butoxy-8-(3-(pyrrolidin-1-ylmethyl)benzyl)-7,8-dihydropteridin-6(5H)-one Preparation of 4-amino-2-butoxy-8-(3-(pyrrolidin-1-ylmethyl)benzyl)-7,8-dihydropteridin-6(5H)-one is described.

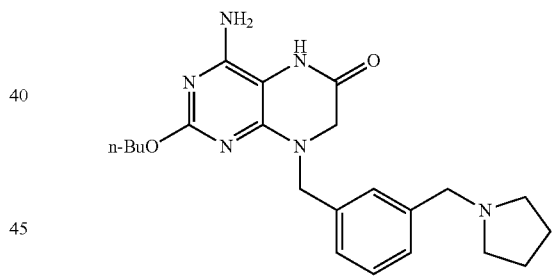

Preparation of ethyl 2-((6-amino-2-butoxy-5-nitropyrimidin-4-yl)(3-(pyrrolidin-1-ylmethyl)benzyl)amino)acetate hydrochloride

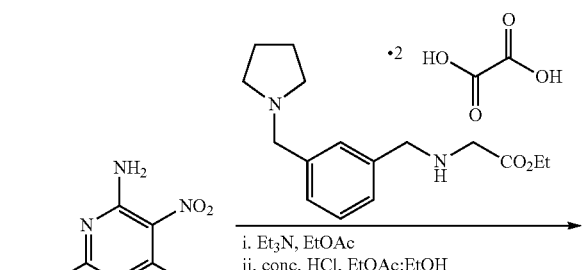

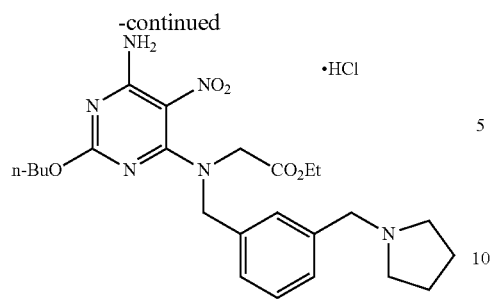

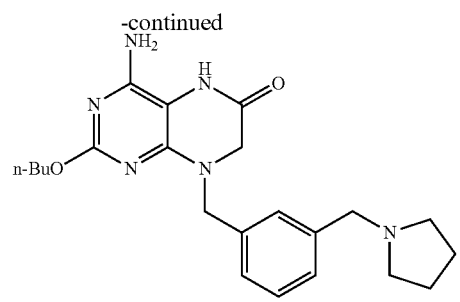

A flask was charged with 2-butoxy-6-chloro-5-nitropyrimidin-4-amine (300 g, 1.0 equiv.), ethyl N-(3-pyrrolidin-1-ylmethyl)benzyl glycinate bis-oxalate (555 g, 1.0 equiv.) and ethyl acetate (6 L). The mixture was agitated and cooled to about 0° C. Triethylamine (616 g, 5.0 equiv.) was slowly added maintaining the internal temperature at about 0° C. The mixture was warmed to room temperature and agitated until the reaction was deemed complete. The reaction was then quenched with an aqueous potassium carbonate solution (10 w/w %, 6 L). The phases were separated and the aqueous phase was extracted with ethyl acetate (6 L). The combined organic layers were concentrated and reconstituted in ethyl acetate (6 L). Ethanol (600 mL) was added and the resultant solution was agitated at room temperature. Concentrated HCl (102 mL, 1.0 equiv.) was slowly added to the reaction mixture. The resultant slurry was agitated at about 20° C. for about 16 hours. The solids were collected by filtration and washed with ethyl acetate/ethanol (600 mL, 9/1 v/v). The product was dried under vacuum to provide ethyl 2-((6-amino-2-butoxy-5-nitropyrimidin-4-yl)(3-(pyrrolidin-1-ylmethyl)benzyl)amino)acetate hydrochloride (504 g, 79% yield). A purified sample of ethyl 2-((6-amino-2-butoxy-5-nitropyrimidin-4-yl)(3-(pyrrolidin-1-ylmethyl)benzyl)amino)acetate hydrochloride has the following spectrum: $^1$H NMR (400 MHz, CDCl$_3$) δ 12.71 (br s, 1H), 7.63-7.69 (m, 1H), 7.57 (s, 1H), 7.30-7.43 (m, 2H), 4.77 (s, 2H), 4.05-4.25 (m, 8H), 3.50-3.66 (m, 2H), 2.71-2.94 (m, 2H), 2.10-2.31 (m, 2H), 1.90-2.10 (m, 2H), 1.62-1.69 (m, 2H), 1.32-1.46 (m, 2H), 1.21-1.29 (m, 3H), 0.85-0.98 (m, 3H).

Preparation of 4-amino-2-butoxy-8-(3-(pyrrolidin-1-ylmethyl)benzyl)-7,8-dihydropteridin-6(5H)-one

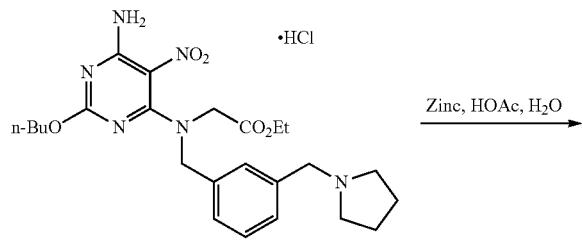

A flask was charged with ethyl 2-((6-amino-2-butoxy-5-nitropyrimidin-4-yl)(3-(pyrrolidin-1-ylmethyl)benzyl)amino)acetate hydrochloride (451 g, 1.0 equiv.), acetic acid (900 mL, 18 equiv.) and water (1.7 L). The solution was agitated at about 20° C. for about 15 minutes. Zinc (196 g, 3.5 equiv.) was charged in portions while maintaining the internal temperature less than about 40° C. After the zinc addition was complete, the mixture was stirred at about 20° C. for about 16 hours. Once the reaction was deemed complete, the mixture was filtered and the solids were washed with water (550 mL). The filtrate was slowly transferred to a flask that contained an aqueous sodium carbonate solution (11 L, 20% w/w) and the resultant slurry was agitated at room temperature for about 2 hours. The solids were collected by filtration and washed with water (10 L) and methanol (2.5 L). The solids were transferred to a flask and dissolved in a methanol and dichloromethane solution (13 L, 1/2 v/v). The solution was purified by silica gel chromatography and triturated with methanol to provide 4-amino-2-butoxy-8-(3-(pyrrolidin-1-ylmethyl)benzyl)-7,8-dihydropteridin-6(5H)-one. A purified sample of the product has the following spectrum:

$^1$H NMR (400 MHz, 99:1, CD$_3$OD:CD$_3$CO$_2$D) δ 7.51-7.40 (m, 4H), 4.82 (s, 2H), 4.34 (s, 2H), 4.19 (t, J=6.6 Hz, 2H), 3.93 (s, 2H), 3.24-3.34 (m, 4H), 2.06 (tt, J=3.5, 3.5 Hz, 4H), 1.67 (tt, J=7.1, 7.3 Hz, 2H), 1.42 (tq, J=7.5, 7.5 Hz, 2H), 0.93 (t, J=7.4, 3H).

Example 7

Preparation of 6-amino-2-butoxy-5-nitropyrimidin-4-ol

Preparation of 6-amino-2-butoxy-5-nitropyrimidin-4-ol is described.

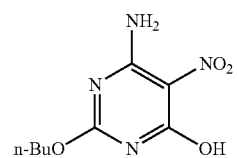

Preparation of 6-amino-2-butoxypyrimidin-4-ol

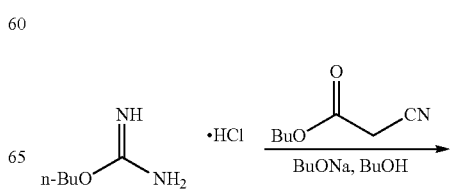

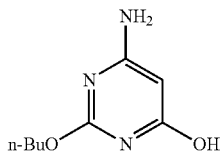

A reactor was charged with 20% n-BuONa in n-BuOH (19.2 g, 40 mmol, 2 equiv.) n-Butyl carbamidate hydrochloride (3.05 g, 20 mmol, 1 equiv.) was added followed by n-butyl cyanoacetate (2.82 g, 20 mmol, 1 equiv.) and the mixture heated to about 80° C. After about 3 hours, an additional charge of 20% n-BuONa in n-BuOH (9.5 g, 20 mmol, 1 equiv.) was added and the reaction stirred for about 9 hours at about 80° C. The reaction was cooled to about 20° C. and quenched with AcOH (2 equiv., 2.4 g) and partitioned between water and MeTHF. The organic layer was dried over MgSO$_4$ and concentrated to an orange solid. Purification on silica gel (95/5 v/v DCM/MeOH) provided 6-amino-2-butoxy-5-nitropyrimidin-4-ol. $^1$H NMR (400 MHz, DMSO-d$_6$) δ 11.30 (s, 2H), 6.29 (s, 2H), 4.67 (s, 1H), 4.16 (t, J=6.7 Hz, 2H), 1.87 (s, 1H), 1.58 (tt, J=6.7, 6.7 Hz, 2H), 1.32 (dq, J=7.4, 6.7 Hz, 2H), 0.86 (t, J=7.4 Hz, 3H).

Preparation of
6-amino-2-butoxy-5-nitrosopyrimidin-4-ol

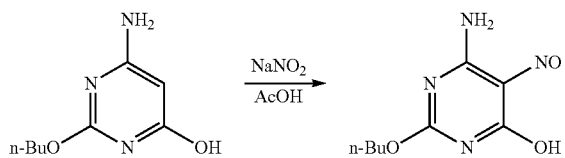

A flask was charged with 6-amino-2-butoxypyrimidin-4-ol (0.42 g, 2.3 mmol) and AcOH (4 mL). The resulting suspension was stirred at about 22° C. and solid sodium nitrite (0.16 g, 2.3 mmol, 1 equiv.) was added, turning the reaction mixture purple and giving a slight exotherm to about 26° C. over 2 minutes. After about 1 hour, the reaction mixture was concentrated and partitioned between MeTHF and water. The aqueous layer was acidified to about pH 1 with 1M NaHSO$_4$ and the layers separated. The aqueous layer was extracted twice with MeTHF, the organics combined and concentrated. $^1$H NMR (400 MHz, CD$_3$OD) δ 5.23 (d, J=6.6 Hz, 2H), 4.38 (t, J=6.6 Hz, 2H), 1.68 (tt, J=7.4, 6.6 Hz, 2H), 1.47-1.28 (m, 2H), 0.91 (t, J=7.4 Hz, 3H).

Alternative preparation of
6-amino-2-butoxy-5-nitrosopyrimidin-4-ol

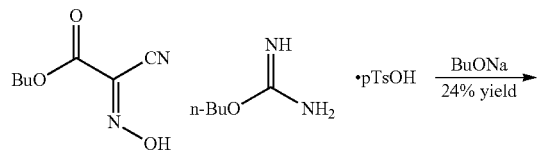

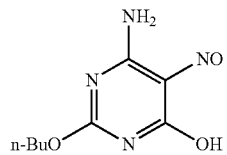

A jacketed reactor was charged with 20% n-BuONa in n-BuOH (14.4 g, 30 mmol, 3 equiv.) O-(n-butyl)isouronuim tosylate (2.9 g, 10 mmol, 1 equiv.) was added followed by ethyl cyanoglyoxylate 2-oxime (1.4 g, 10 mmol, 1 equiv.) and the mixture heated to about 40° C. for about 22 hours. The reaction was quenched with AcOH (2 equiv.) and partitioned between EtOAc and dilute brine. The organic layer was washed four times with water, dried over Na$_2$SO$_4$, and concentrated and purified on silica gel (95/5 v/v DCM/MeOH) to provide 6-amino-2-butoxy-5-nitrosopyrimidin-4-ol. $^1$H NMR (400 MHz, CD$_3$OD) δ 5.23 (d, J=6.6 Hz, 2H), 4.38 (t, J=6.6 Hz, 2H), 1.68 (tt, J=7.4, 6.6 Hz, 2H), 1.47-1.28 (m, 2H), 0.91 (t, J=7.4 Hz, 3H).

Preparation of
6-amino-2-butoxy-5-nitropyrimidin-4-ol

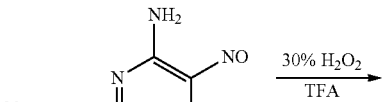

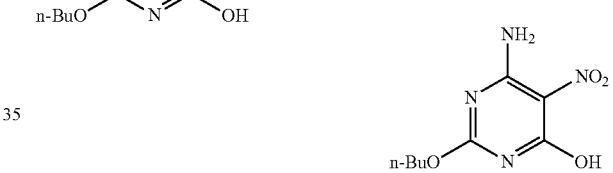

6-amino-2-butoxy-5-nitrosopyrimidin-4-ol (400 mg 1.88 mmol) and trifluoroacetic acid (4 mL) were combined and cooled to about 5° C. 30% hydrogen peroxide (0.42 mL, 3.77 mmol, 2 equiv.) was added dropwise and then stirred for about 1 hour. The reaction was deemed incomplete by conventional methods and an additional charge of 30% hydrogen peroxide (0.25 mL) was added and the reaction stirred for about 30 min. The reaction mixture was concentrated, partitioned between MeTHF and 1M NaOAc. Purification on silica gel (95/5 v/v DCM/MeOH) provided 6-amino-2-butoxy-5-nitropyrimidin-4-ol. $^1$H NMR (400 MHz, DMSO-d$_6$) δ 12.04 (s, 1H), 8.74-8.80 (m, 2H), 4.33 (t, J=6.6 Hz, 2H), 1.66 (tt, J=7.1, 7.2 Hz, 2H), 1.37 (tq, J=7.4, 7.4 Hz, 2H), 0.91 (t, J=7.4 Hz, 3H).

Example 8

Preparation of ethyl 2-((6-amino-2-butoxy-5-nitropyrimidin-4-yl)(3-(pyrrolidin-1-ylmethyl)benzyl)amino)acetate

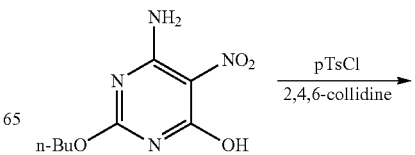

-continued

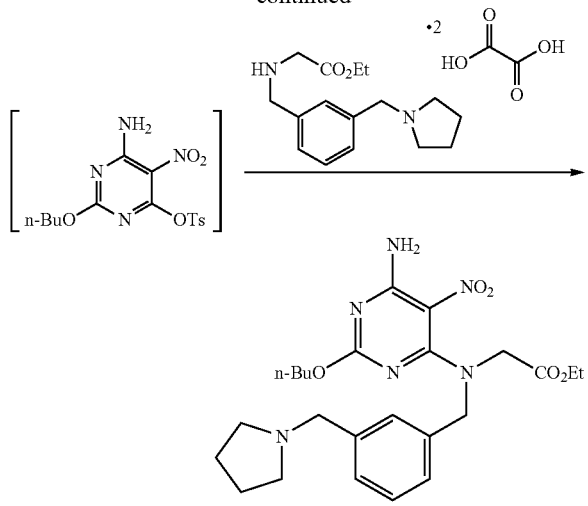

A flask was charged with 6-amino-2-butoxy-5-nitropyrimidin-4-ol (0.28 g, 1.22 mmol, 1 equiv.) and acetonitrile (4 mL). 2,4,6-Collidine (0.65 mL, 4 equiv.) was added followed by p-toluenesulfonyl chloride (0.23 g, 1 equiv.) The reaction mixture was stirred at about 60° C. for about 6 hours followed by an additional charge of p-toluenesulfonyl chloride (0.06 g, 0.25 equiv.) After one more hour at about 60° C., ethyl N-(3-pyrrolidin-1-ylmethyl)benzyl glycinate bis-oxalate salt (0.56 g, 1 equiv.) was added and the reaction mixture allowed to cool to ambient temperature and stirred for about 15 hours. The reaction mixture was diluted with MeTHF, washed with saturated aqueous potassium carbonate, saturated aqueous sodium chloride and concentrated in vacuo. The residue was purified on silica gel (95/5 v/v DCM/MeOH) providing the product. The NMR matches that described previously in WO 2010/077613.

Example 9

Preparation of ethyl 2-((6-amino-2-butoxy-5-nitro-pyrimidin-4-yl)(4-(pyrrolidin-1-ylmethyl)benzyl)amino)acetate

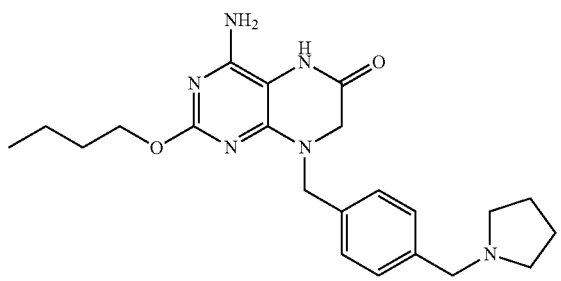 [SMILES: CCCCOc1nc(N)c2c(n1)N(Cc1ccc(CN3CCCC3)cc1)CC(=O)N2]

Figure 8:
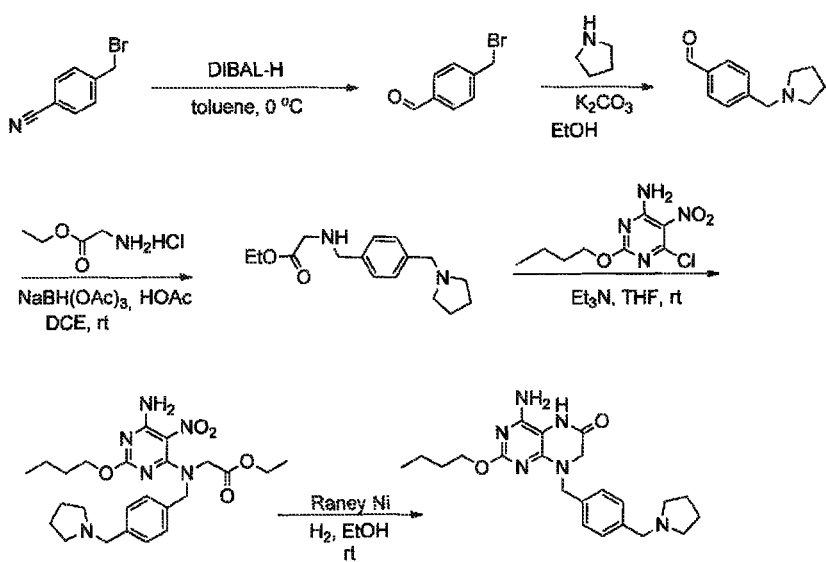
FIG. 8 shows the preparation of the compound of Formula I by coupling the compound of Formula II having a chloro leaving group, with the compound of Formula III, followed by ring closure using Raney/Ni. Preparation of the compound of Formula III is also shown.

The compound was prepared according to scheme shown in FIG. 8.

Preparation of 4-(bromomethyl)-benzaldehyde. To a solution of 4-(bromomethyl)-benzonitrile (18.50 g, 94.4 mmol, 1 equiv.) in toluene (185 mL) at 0° C. was added Dibal-H (1.5 M in toluene, 78.7 mL, 118 mmol, 1.25 equiv.) over about 90 min. Once addition was complete, the reaction was allowed to stir an additional 90 min. Then 1.0 M aq HCl (462.5 mL, 462.5 mmol) was added carefully, and the reaction was allowed to stir for 15 min. The organic phase was collected, and the aqueous phase was extracted with ethyl acetate (2×250 mL). All organic extracts were combined, dried over $Na_2SO_4$, filtered, and concentrated to give 4-(bromomethyl)-benzaldehyde which was used directly to the next step.

Preparation of 4-(pyrrolidin-1-ylmethyl)benzaldehyde. A suspension of $K_2CO_3$ (35.4 g, 257 mmol, 3 equiv.) in absolute ethanol (150 mL) was treated with pyrrolidine (6.12 g, 85 mmol, 1 equiv.). To the mixture was added 4-(bromomethyl)-benzaldehyde (17 g, 85 mmol, 1 equiv.), and the reaction was heated at about 65° C. for about 1 h. The reaction was cooled and filtered. The cake was washed with ethanol. The filtrate was concentrated to give a residue, which was partitioned between DCM (500 mL) and 2% w/v aq $NaHCO_3$ (500 mL). The organic phase was collected, and the aqueous layer was extracted with DCM (2×300 mL). The organic layers were combined, dried over $Na_2SO_4$, filtered, and concentrated, and purified with silica gel column chromatography giving 4-(pyrrolidin-1-ylmethyl)-benzaldehyde.

Preparation of ethyl N-(4-pyrrolidin-1-ylmethyl)benzyl glycinate. Glycine ethyl ester hydrochloride (270 mg, 1.94 mmol, 3 equiv.), 4-(pyrrolidin-1-ylmethyl) benzaldehyde (122 mg, 0.65 mmol, 1 equiv.), and 1,2-dichloroethane (5 mL) was treated portionwise with $NaBH(OAc)_3$ (274 mg, 1.67 mmol, 2.6 equiv.) at ambient temperature. After about 5 min, glacial AcOH (77 mg, 1.3 mmol) was added dropwise over about 5 min at ambient temperature. Upon reaction completion, the mixture was quenched with saturated aq. $NaHCO_3$ to pH of about 8.0. The quenched reaction was warmed to ambient temperature and stirred for about 30 min. The biphasic system was extracted with DCM (3×20 mL). The organic layers were combined, dried ($Na_2SO_4$), filtered, and concentrated to afford the title compound.

Preparation of [(6-Amino-2-butoxy-5-nitro-pyrimidin-4-yl)-(4-pyrrolidin-1-ylmethyl-benzyl)-amino]-acetic acid ethyl ester. To a solution of 2-butoxy-6-chloro-5-nitro-pyrimidin-4-ylamine (0.25 g, 1.02 mmol, 1 equiv.) in THF (5 mL) at about 0° C. was added $Et_3N$ (0.31 mL, 2.25 mmol, 2.2 equiv.) and the mixture was allowed to stir for about 15-20 minutes. To this mixture was added the ethyl N-(4-pyrrolidin-1-ylmethyl)benzyl glycinate (0.3 g, 1.1 mmol, 1.1 equiv.) in THF (3 mL) over about 5 min. The reaction mixture was stirred at ambient temperature until reaction is completed. The reaction mixture was filtered and the filter cake was washed with EtOAc. The filtrate was concentrated and purified with silica gel column chromatography to give the title compound.

Preparation of 4-amino-2-butoxy-8-(4-(pyrrolidin-1-ylmethyl-benzyl)-7,8-dihydro-5H-peridin-6-one. To a solution of [(6-Amino-2-butoxy-5-nitro-pyrimidin-4-yl)-(4-pyrrolidin-1-ylmethyl-benzyl)-amino]-acetic acid ethyl ester (0.25 g, 0.49 mmol, 1 equiv.) in MeOH (10 mL) was added Raney-Ni (100 mg, wet). The mixture was degassed and filled with hydrogen (3×). The mixture was stirred under a hydrogen atmosphere at ambient temperature overnight, filtered and concentrated to give the crude product, which was washed with MeOH/Ethyl acetate (1:10 v/v), and dried to give the title compound. LC-MS: 410, found 411 (M+1). The NMR matches that described previously in WO 2010/077613.

Example 10

Preparation of 4-amino-2-butoxy-8-(3-(pyrrolidin-1-ylmethyl)benzyl)-7,8-dihydropteridin-6(5H)-one Preparation of 4-amino-2-butoxy-8-(3-(pyrrolidin-1-ylmethyl)benzyl)-7,8-dihydropteridin-6(5H)-one is described.

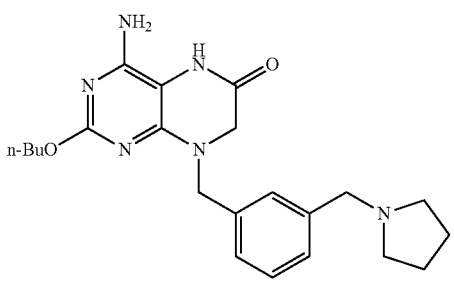

Preparation of ethyl 2-((6-amino-2-butoxy-5-nitro-pyrimidin-4-yl)(3-(pyrrolidin-1-ylmethyl)benzyl)amino)acetate hydrochloride

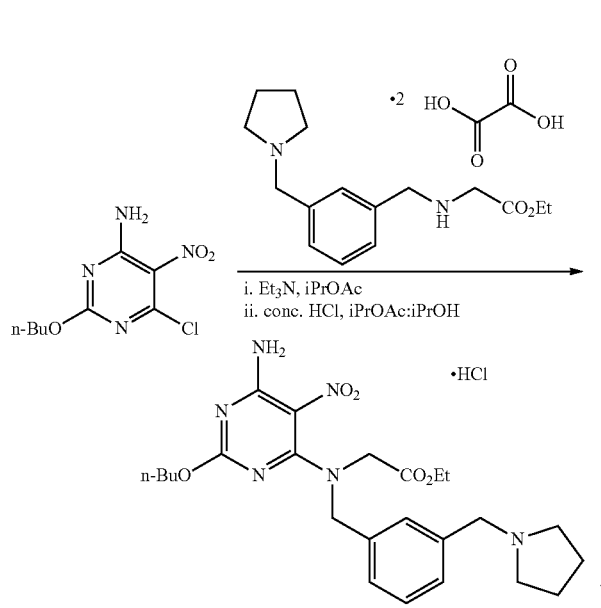

A flask was charged with 2-butoxy-6-chloro-5-nitropyrimidin-4-amine (125 g, 1.0 equiv.), ethyl N-(3-pyrrolidin-1-ylmethyl)benzyl glycinate bis-oxalate (231 g, 1.25 equiv.) and isopropyl acetate (2.5 L). The mixture was agitated and cooled to about 5° C. Triethylamine (256 g, 5.0 equiv.) was slowly added maintaining the internal temperature at about 10° C. The mixture was warmed to room temperature and agitated until the reaction was deemed complete. The reaction was then quenched with brine (1.5 w/w %, 1.5 L), NH$_4$OH (125 g) and water (0.75 L). The phases were separated and the organic phase was washed with water (1 L). The combined aqueous phases were extracted with isopropyl acetate (1.25 L). The combined organic layers were concentrated to about 2.5 L in volume. Fresh isopropyl acetate (1.5 L) was added and the resultant solution was concentrated to about 3.2 L in volume. Isopropyl alcohol (250 mL) was added at 20° C. Ethyl 2-((6-amino-2-butoxy-5-nitropyrimidin-4-yl)(3-(pyrrolidin-1-ylmethyl)benzyl)amino)acetate hydrochloride seeds (3.75 g) were added followed by concentrated HCl (43 mL, 1.0 equiv.) added slowly to the reaction mixture. The resultant slurry was agitated at about 20° C. for about 16 hours. The solids were collected by filtration and washed with isopropyl acetate/isopropanol (625 mL, 9/1 v/v). The product was dried under vacuum to provide ethyl 2-((6-amino-2-butoxy-5-nitropyrimidin-4-yl)(3-(pyrrolidin-1-ylmethyl)benzyl)amino)acetate hydrochloride (239 g, 90% yield). A purified sample of ethyl 2-((6-amino-2-butoxy-5-nitropyrimidin-4-yl)(3-(pyrrolidin-1-ylmethyl)benzyl)amino)acetate hydrochloride has the following spectrum: $^1$H NMR (400 MHz, CDCl$_3$) δ 12.71 (br s, 1H), 7.63-7.69 (m, 1H), 7.57 (s, 1H), 7.30-7.43 (m, 2H), 4.77 (s, 2H), 4.05-4.25 (m, 8H), 3.50-3.66 (m, 2H), 2.71-2.94 (m, 2H), 2.10-2.31 (m, 2H), 1.90-2.10 (m, 2H), 1.62-1.69 (m, 2H), 1.32-1.46 (m, 2H), 1.21-1.29 (m, 3H), 0.85-0.98 (m, 3H).

Preparation of 4-amino-2-butoxy-8-(3-(pyrrolidin-1-ylmethyl)benzyl)-7,8-dihydropteridin-6(5H)-one

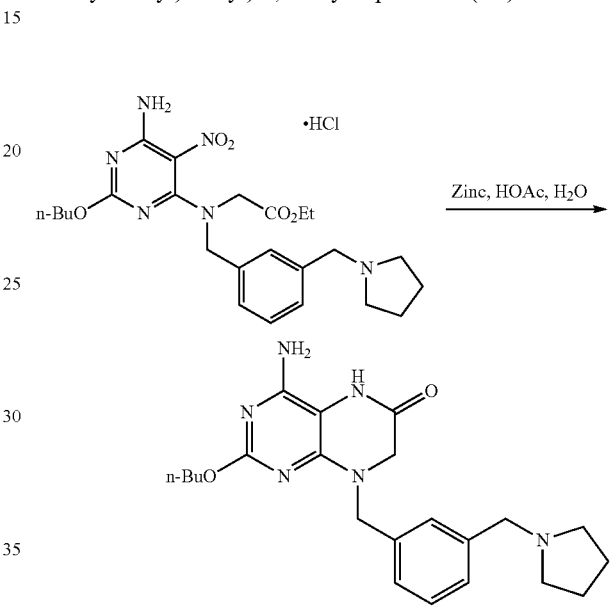

A flask was charged with ethyl 2-((6-amino-2-butoxy-5-nitropyrimidin-4-yl)(3-(pyrrolidin-1-ylmethyl)benzyl)amino), acetate hydrochloride (200 g, 1.0 eq), water (740 mL) and acetic acid (382 mL, 17.5 equiv.). The solution was agitated at about 20° C. for about 15 minutes. In a separate flask, zinc (87.5 g, 4 equiv.) and water (400 mL) was mixed, and the solution from the first flask was added slowly to the internal temperature below about 40° C. After the addition was complete, the first flask was rinsed with 250 mL water and added to the reaction and the mixture was stirred at about 20° C. for about 1 h. Once the reaction was deemed complete, the mixture was filtered and the solids were washed with water (400 mL). Ammonium hydroxide (770 mL) was slowly added to the filtrate and the resulting slurry was stirred at about 20° C. for about 2 h. The solids were collected by filtration and washed with with water (2×1 L) methanol (1 L) and isopropyl acetate (1 L). The solids were transferred to a flask and dissolved in a methanol and dichloromethane solution (4.2 L, 1/2.2 v/v). The solution was purified by silica gel chromatography. The purified solution was concentrated to about 1.3 L. Methanol (2.5 L) was added and the mixture was concentrated to about 1.3 L. An additional portion of methanol (2.5 L) was added and the mixture was concentrated to about 1.3 L. The resulting slurry was stirred at about 20° C. for 3 h. The solids were collected by filtration and washed with methanol (260 mL) and isopropyl acetate (260 mL). The product was dried under vacuum to provide 4-amino-2-butoxy-8-(3-(pyrrolidin-1-ylmethyl)benzyl)-7,8-dihydropteridin-6(5H)-one (111 g, 85%). A purified sample of the product has the following spectrum: $^1$H NMR (400 MHz, 99:1, CD$_3$OD:CD$_3$CO$_2$D) δ 7.51-7.40 (m, 4H), 4.82 (s, 2H), 4.34 (s, 2H), 4.19 (t, J=6.6 Hz, 2H), 3.93 (s, 2H), 3.24-3.34 (m, 4H), 2.06 (tt, J=3.5, 3.5 Hz, 4H), 1.67 (tt, J=7.1, 7.3 Hz, 2H), 1.42 (tq, J=7.5, 7.5 Hz, 2H), 0.93 (t, J=7.4, 3H).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of making a compound of Formula Ia:

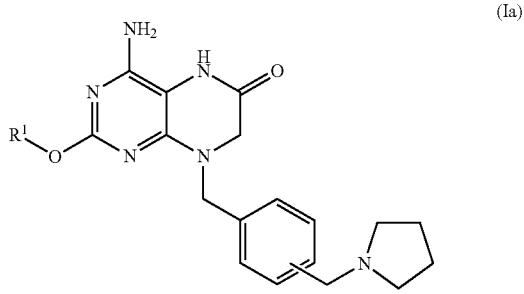

(Ia)

comprising:
(a) forming a first reaction mixture comprising a compound of Formula IIa:

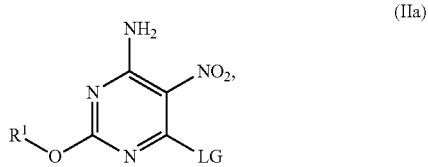

(IIa)

a non nucleophilic base, a first solvent, and a compound of Formula IIIa:

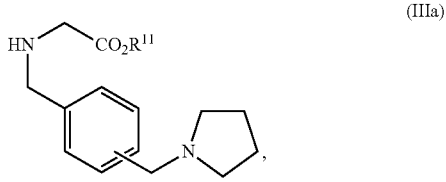

(IIIa)

under conditions suitable to form a compound of Formula IVa:

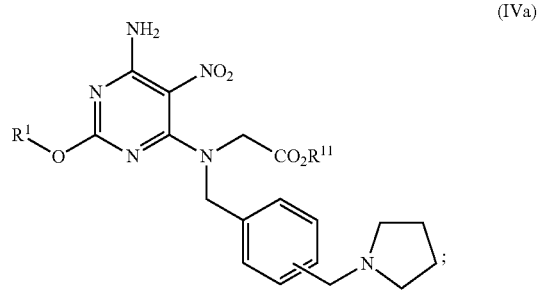

(IVa)

and
(b) forming a second reaction mixture comprising the compound of Formula IVa, a second solvent and a reducing agent under conditions suitable to prepare the compound of Formula I,
wherein
R$^1$ and R$^{11}$ are each independently C$_1$-C$_6$ alkyl; and
LG is selected from the group consisting of halogen, —OH, and —OSO$_2$R$^{13}$, wherein R$^{13}$ is selected from the group consisting of C$_1$-C$_6$ alkyl, C$_1$-C$_6$ haloalkyl and aryl, wherein the aryl group is substituted with 1 to 3 R$^{13a}$ groups each independently selected from the group consisting of C$_1$-C$_6$ alkyl, halogen, and NO$_2$.

2. The method of claim 1, wherein the non-nucleophilic base is selected from the group consisting of triethylamine, diisopropylethyl amine, N,N-diethylaniline, pyridine, 2,6-lutidine, 2,4,6-collidine, 4-dimethylaminopyridine, and quinuclidine.

3. The method of claim 1, wherein the non-nucleophilic base is triethylamine.

4. The method of claim 1, wherein the non-nucleophilic base is 2,4,6-collidine.

5. The method of claim 1, wherein the first solvent is selected from the group consisting of ethyl acetate, isopropyl acetate, tetrahydrofuran, acetonitrile, and combinations thereof.

6. The method of claim 1, wherein the first solvent comprises ethyl acetate.

7. The method of claim 1, wherein the first solvent comprises isopropyl acetate.

8. The method of claim 1, wherein the first solvent comprises acetonitrile.

9. The method of claim 1, wherein the compound of Formula IIIa is the bis-oxalate salt of Formula IIIa.

10. The method of claim 1, further comprising prior to step (b):
(a1) forming a reaction mixture comprising the compound of Formula IVa and hydrochloric acid to form a monohydrochloride form of the compound of Formula IVa.

11. The method of claim 1, wherein the reducing agent is selected from the group consisting of zinc, iron, Raney nickel, sodium sulfide, sodium dithionite, ammonium sulfide, palladium on carbon, lithium aluminum hydride, and sodium borohydride.

12. The method of claim 1, wherein the reducing agent is zinc.

13. The method of claim 1, wherein the reducing agent is Raney nickel.

14. The method of claim 1, wherein the second solvent is selected from the group consisting of acetic acid, water, methanol, ethanol, isopropanol, tetrahydrofitran, and combinations thereof.

15. The method of claim 1, wherein the second solvent comprises acetic acid and water.

16. The method of claim 1, wherein the second reaction mixture is maintained at a temperature of from about 10° C. to about 30° C.

17. The method of claim 1, wherein $R^1$ is selected from the group consisting of methyl, ethyl, n-propyl, iso-propyl, n-butyl, iso-butyl, sec-butyl, t-butyl, n-pentyl, tert-pentyl, neopentyl, iso-pentyl, sec-pentyl, 3-pentyl, hexyl, and 2-ethyl-butyl.

18. The method of claim 1, wherein the leaving group LG is selected from the group consisting of chloro, —OH, and —O—tosyl.

19. The method of claim 1, wherein the compound of Formula Ia has the structure:

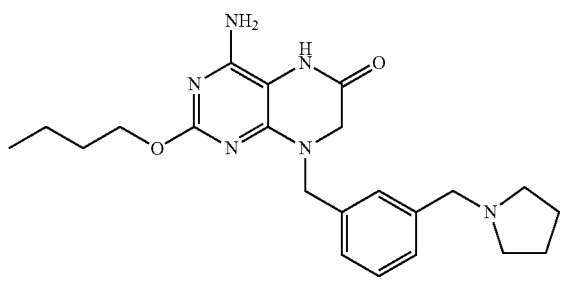 [SMILES: CCCCOc1nc(N)c2c(n1)N(Cc1cccc(CN3CCCC3)c1)CC(=O)N2]

and the method comprises:
(a) forming the first reaction mixture comprising the compound of Formula IIa having the structure:

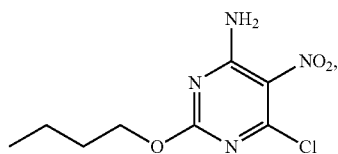 [SMILES: CCCCOc1nc(N)c([N+](=O)[O-])c(Cl)n1]

triethylamine, ethyl acetate, and the bisoxalate salt of the compound of Formula IIIa having the structure:

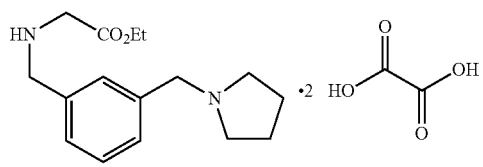 [SMILES: CCOC(=O)CNCc1cccc(CN2CCCC2)c1 ; O=C(O)C(=O)O]

under conditions suitable to form the compound of Formula IVa having the structure:

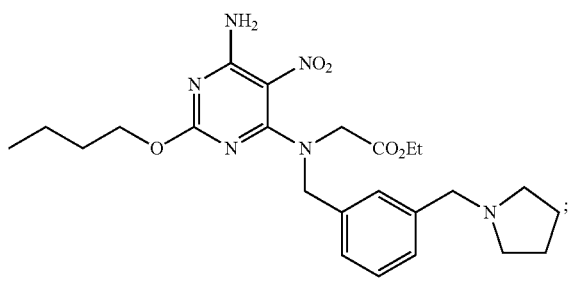 [SMILES: CCCCOc1nc(N)c([N+](=O)[O-])c(N(CC(=O)OCC)Cc2cccc(CN3CCCC3)c2)n1]

(a1) forming a reaction mixture comprising the compound of Formula IVa and hydrochloric acid to form a monohydrochloride form of the compound of Formula IVa; and (b) forming the second reaction mixture comprising the monohydrochloride firm of the compound of Formula IVa, zinc, and acetic acid, under conditions suitable to prepare the compound of Formula Ia.

20. The method of claim 1, wherein the compound of Formula Ia has the structure:

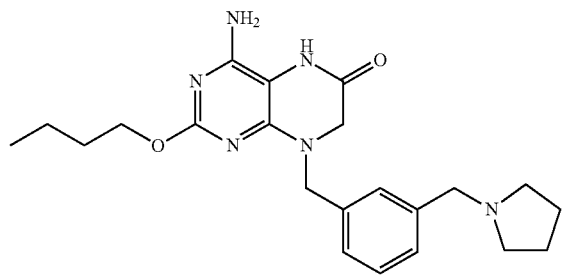 [SMILES: CCCCOc1nc(N)c2c(n1)N(Cc1cccc(CN3CCCC3)c1)CC(=O)N2]

and the method comprises:
(a) forming the first reaction mixture comprising the compound of Formula IIa having the structure:

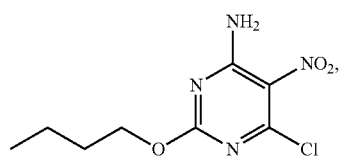

triethylamine, isopropyl acetate, and the bisoxalate salt of the compound of Formula IIIa having the structure:

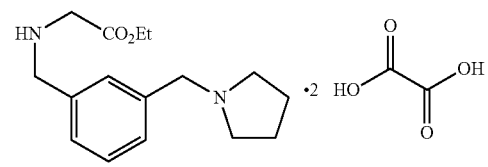 [SMILES: CCOC(=O)CNCc1cccc(CN2CCCC2)c1 ; O=C(O)C(=O)O]

under conditions suitable to form the compound of Formula IVa having the structure:

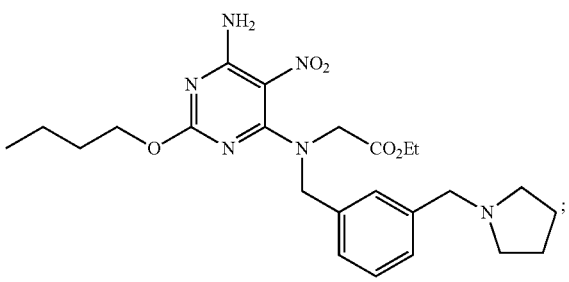 [SMILES: CCCCOc1nc(N)c([N+](=O)[O-])c(N(CC(=O)OCC)Cc2cccc(CN3CCCC3)c2)n1]

(a1) forming a reaction mixture comprising the compound of Formula IVa and hydrochloric acid to form a monohydrochloride form of the compound of Formula IVa; and (b) forming the second reaction mixture comprising the monohydrochloride form of the compound of Formula IVa, zinc, and acetic acid, under conditions suitable to prepare the compound of Formula Ia.

21. The method of claim 1, wherein the compound of Formula Ia has the structure:

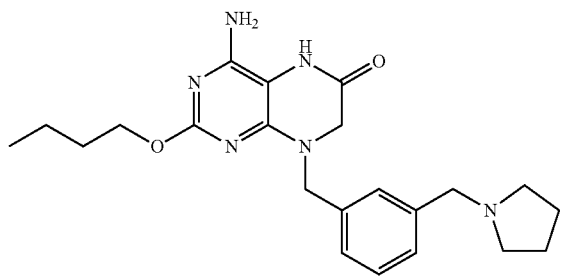 [SMILES: CCCCOc1nc(N)c2c(n1)N(Cc1cccc(CN3CCCC3)c1)CC(=O)N2]

and the method comprises:

(a) forming the first reaction mixture comprising the compound of Formula IIa having the structure:

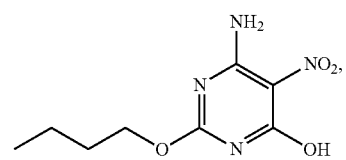 [SMILES: CCCCOc1nc(N)c([N+](=O)[O-])c(O)n1]

2,4,6-collidine, acetonitrile, and tosyl-Cl, under conditions suitable to form the compound of Formula IIa having the structure:

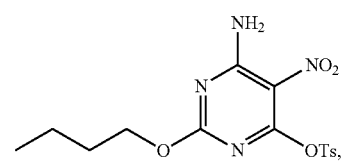 [SMILES: CCCCOc1nc(N)c([N+](=O)[O-])c(OS(=O)(=O)c2ccc(C)cc2)n1]

and adding to the reaction mixture the bisoxalate salt of the compound of Formula IIIa having the structure:

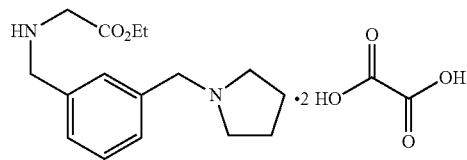

under conditions suitable to form the compound of Formula IVa having the structure:

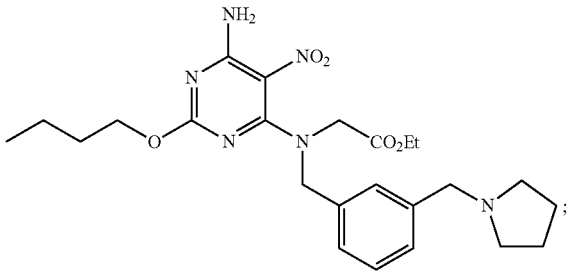 [SMILES: CCCCOc1nc(N)c([N+](=O)[O-])c(N(CC(=O)OCC)Cc2cccc(CN3CCCC3)c2)n1]

and (b) forming the second reaction mixture comprising the compound of Formula IV, Raney nickel, hydrogen and methanol, under conditions suitable to prepare the compound of Formula Ia.

22. The method of claim 1, wherein the compound of Formula Ia has the structure:

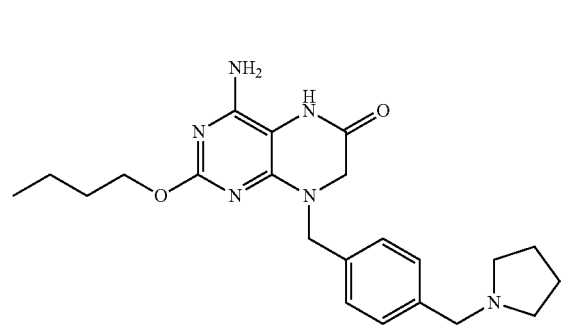 [SMILES: CCCCOc1nc(N)c2c(n1)N(Cc1ccc(CN3CCCC3)cc1)CC(=O)N2]

and the method comprises:

(a) forming the first reaction mixture comprising the compound of Formula IIa having the structure:

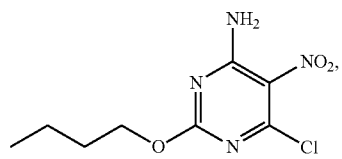

triethylamine, tetrahydrofuran, and the compound of Formula IIIa having the structure:

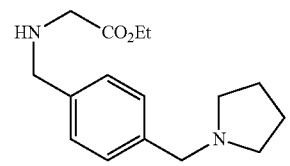

under conditions suitable to form the compound of Formula IVa having the structure:

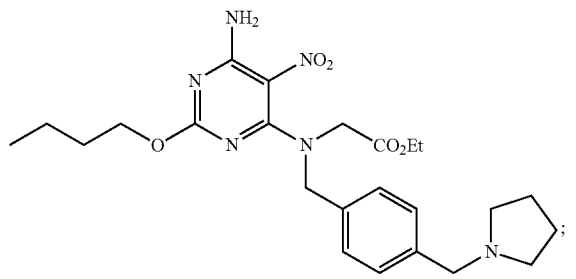 [SMILES: CCCCOc1nc(N)c([N+](=O)[O-])c(N(CC(=O)OCC)Cc2ccc(CN3CCCC3)cc2)n1]

and (b) forming the second reaction mixture comprising the compound of Formula IVa, Raney nickel, hydrogen and ethanol, under conditions suitable to prepare the compound of Formula Ia.

23. A method of preparing a compound of Formula IIIa:

(IIIa)

comprising forming a first reaction mixture comprising Br—$CH_2$—$CO_2R^{11}$, a non-nucleophilic base, and a compound of Formula Va:

(Va)

under conditions suitable to form the compound of Formula IIIa, wherein the compound of Formula IIIa is present at the kilogram scale, wherein $R^{11}$ is $C_1$-$C_6$ alkyl.

24. The method of claim 23, wherein the non-nucleophilic base is selected from the group consisting of triethylamine, diisopropylethyl amine, N,N-diethylaniline, pyridine, 2,6-lutidine, 2,4,6-collidine, 4-dimethylaminopyridine, and quinuclidine.

25. The method of claim 23, wherein the non-nucleophilic base comprises triethylamine.

26. The method of claim 23, wherein the method comprises forming the first reaction mixture comprising BrCH$_2$CO$_2$Et, NEt$_3$, and the compound of Formula Va having the structure:

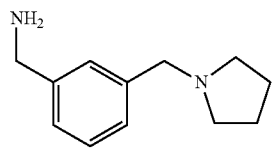

under conditions suitable to form the compound of Formula IIIa having the structure:

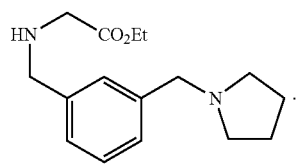 [SMILES: CCOC(=O)CNCc1cccc(CN2CCCC2)c1]

27. A method of preparing a compound of Formula IIIa:

(IIIa)

comprising forming a first reaction mixture comprising OHC—$CO_2R^{11}$, a reducing agent, and a compound of Formula Va:

(Va)

under conditions suitable to form a compound of Formula IIIa, wherein $R^{11}$ is $C_1$-$C_6$ alkyl.

28. The method of claim 27, wherein the reducing agent is selected from the group consisting of Na(OAc)$_3$BH, NaBH$_3$CN, NaBH$_4$, Zn/HCl, and BH$_3$-pyridine.

29. The method of claim 27, wherein the reducing agent is Na(OAc)$_3$BH.

30. The method of claim 27, wherein the method comprises forming the first reaction mixture comprising OHC—CO$_2$Et, Na(OAc)$_3$BH, and the compound of Formula Va having the structure:

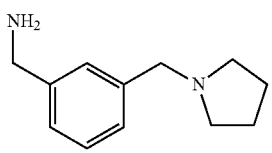 [SMILES: NCc1cccc(CN2CCCC2)c1]

under conditions suitable to form the compound of Formula IIIa having the structure:

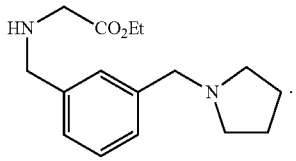 [SMILES: CCOC(=O)CNCc1cccc(CN2CCCC2)c1]

31. A method of preparing a compound of Formula IIIa:

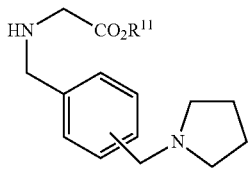
(IIIa)

comprising
(a) forming a first reaction mixture comprising H$_2$N—CH$_2$—CO$_2$R$^{11}$, a non-nucleophilic base, and a compound of Formula VIa:

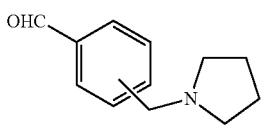
(VIa)

under conditions suitable to form an intermediate compound, and
(b) forming a second reaction mixture comprising the intermediate compound and a reducing agent, under conditions suitable to form the compound of Formula IIIa,
wherein
R$^{11}$ is C$_1$-C$_6$ alkyl.

32. The method of claim 31, wherein
the non-nucleophilic base is selected from the group consisting of triethylamine, diisopropylethyl amine, N,N-diethylaniline, pyridine, 2,6-lutidine, 2,4,6-collidine, 4-dimethylaminopyridine, and quinuclidine; and
the reducing agent is selected from the group consisting of Na(OAc)$_3$BH, NaBH$_3$CN, NaBH$_4$, Zn/HCl, and BH$_3$-pyridine.

33. The method of claim 31, wherein
the non-nucleophilic base is triethylamine; and
the reducing agent is Na(OAc)$_3$BH.

34. The method of claim 31, wherein the first reaction mixture further comprises a sulfate salt selected from the group consisting of sodium sulfate and magnesium sulfate.

35. The method of claim 31, wherein the method comprises
(a) forming the first reaction mixture comprising H$_2$N—CH$_2$—CO$_2$Et, NEt$_3$, MgSO$_4$, and the compound of Formula VIa having the structure:

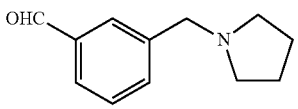 [SMILES: O=Cc1cccc(CN2CCCC2)c1]

under conditions suitable to form the intermediate compound; and
(b) forming the second reaction mixture comprising the intermediate compound, Na(OAc)$_3$BH, and acetic acid, under conditions suitable to form the compound of Formula IIIa having the structure:

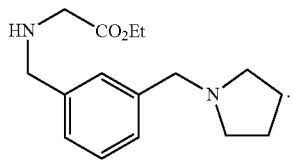 [SMILES: CCOC(=O)CNCc1cccc(CN2CCCC2)c1]

36. A compound having the structure:

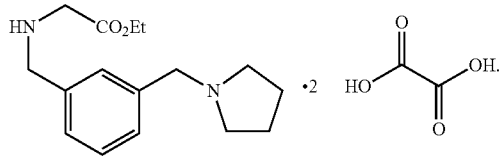 [SMILES: CCOC(=O)CNCc1cccc(CN2CCCC2)c1 ; O=C(O)C(=O)O]

37. A method of preparing the compound of claim 36 comprising forming a reaction mixture comprising oxalic acid and a compound having the structure:

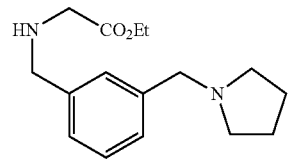 [SMILES: CCOC(=O)CNCc1cccc(CN2CCCC2)c1]

under conditions suitable to prepare the salt.

38. A method of preparing a compound of Formula IIa:

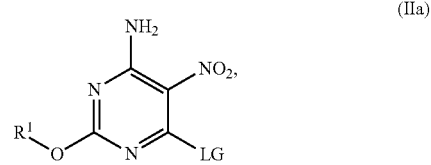
(IIa)

comprising
forming a first reaction mixture comprising ammonia, a first non-nucleophilic base, and a compound of Formula IIb having the structure:

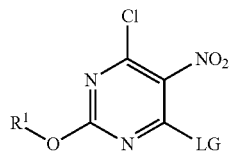

under conditions suitable to form the compound of Formula IIa,
wherein
R¹ is $C_1$-$C_6$ alkyl; and
LG is a leaving group selected from the group consisting of halogen, —OH and —$OSO_2R^{13}$, wherein $R^{13}$ is selected from the group consisting of $C_1$-$C_6$ alkyl, $C_1$-$C_6$ haloalkyl and aryl, wherein the aryl group is substituted with 1 to 3 $R^{13a}$ groups each independently selected from the group consisting of $C_1$-$C_6$ alkyl, halogen, and $NO_2$.

39. The method of claim 38, wherein the first non-nucleophille base is selected from the group consisting of triethylamine, diisopropylethyl amine, N,N-diethylaniline, pyridine, 2,6-lutidine, 2,4,6-collidine, 4-dimethylaminopyridine, and quinuclidine.

40. The method of claim 38, wherein the first non-nucleophilic base is triethylamine.

41. The method of claim 38, further comprising, prior to the step of forming the first reaction mixture, the steps of:
(a) forming a reaction mixture comprising a nitration agent, and a compound of Formula IIc:

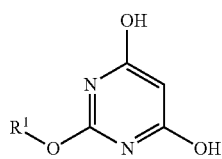

(IIc)

under conditions suitable to form the compound of Formula IId:

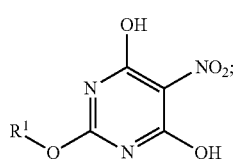

(IId)

and
(b) forming a reaction mixture comprising a chlorination agent, a second non-nucleophilic base and the compound of Formula IId, under conditions suitable to form the compound of Formula IIb having the structure:

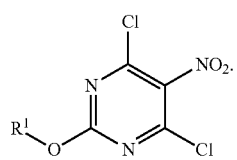

42. The method of claim 41, wherein
the chlorination agent is selected from the group consisting of phosphorous oxychloride, thionyl chloride, oxalyl chloride and sulfuryl chloride; and
the second non-nucleophilic base is selected from the group consisting of triethylamine, diisopropylethyl amine, N,N-climethylaniline, N,N-diethylaniline, pyridine, 2,6-lutidine, 2,4,6-collidine, 4-dimethylaminopyridine, and quinuclidine.

43. The method of claim 41, wherein
the first non-nucleophilic base is triethylamine;
the nitration agent is nitric acid;
the chlorination agent is phosphorous oxychloride; and
the second non-nucleophilic base is N,N-diethylaniline.

44. The method of claim 41, comprising
(a) forming the reaction mixture comprising nitric acid, acetic acid, and a compound of Formula IIc:

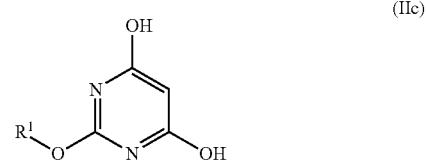

under conditions suitable to form the compound of Formula IId:

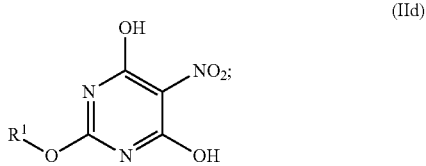

(b) forming the reaction mixture comprising phosphorous oxychfolide, N,N-dimethylaniline, and the compound of Formula IId, under conditions suitable to form the compound of Formula IIb:

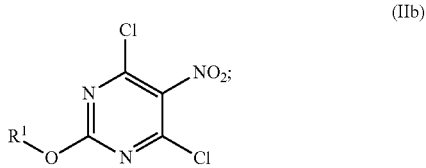

and
(c) forming the first reaction mixture comprising ammonia, triethylamine, and the compound of Formula IIb, under conditions suitable to form the compound of Formula IIa.

45. A compound of Formula IIe having the structure:

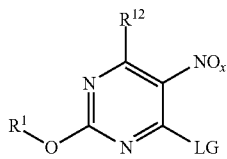

(IIe)

wherein $R^1$ is $C_1$-$C_6$ alkyl;

LG is a leaving group selected from the group consisting of halogen, —OH and —OSO$_2$R$^{13}$, wherein $R^{13}$ is selected from the group consisting of $C_1$-$C_6$ alkyl, $C_1$-$C_6$ haloalkyl and aryl, wherein the aryl group is substituted with 1 to 3 $R^{13a}$ groups each independently selected from the group consisting of $C_1$-$C_6$ alkyl, halogen, and NO$_2$;

$R^{12}$ is selected from the group consisting of halogen, —OH and —NH$_2$; and subscript x is 1 or 2, such that when $R^{12}$ is —NH$_2$ and subscript x is 2, then LG is a halogen.

46. The compound of claim 45, wherein subscript x is 1.

47. The compound of claim 45, wherein subscript x is 2.

48. The compound of claim 45, wherein $R^1$ is n-butyl;

$R^{12}$ is selected from the group consisting of chloro, —OH and —NH$_2$; and

LG is selected from the group consisting of chloro and —OH.

49. The compound of claim 45, wherein the compound of Formula IIe is selected from the group consisting of:

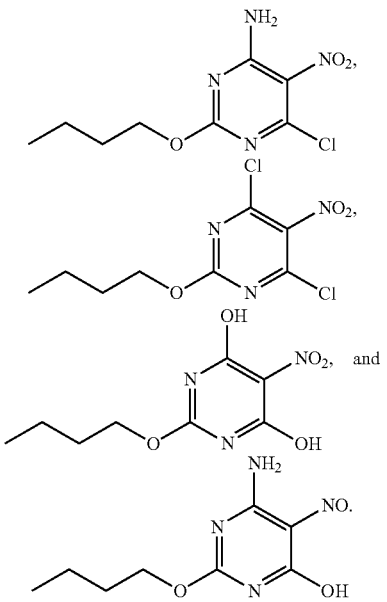

* * * * *